United States Patent
Makriyannis et al.

(10) Patent No.: US 10,570,146 B2
(45) Date of Patent: Feb. 25, 2020

(54) UREA/CARBAMATES FAAH MAGL OR DUAL FAAH/MAGL INHIBITORS AND USES THEREOF

(71) Applicant: Northeastern University, Boston, MA (US)

(72) Inventors: Alexandros Makriyannis, Watertown, MA (US); Vidyanand G Shukla, Boston, MA (US); Shakiru O Alapafuja, Willimantic, CT (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 15/328,428

(22) PCT Filed: Jul. 24, 2015

(86) PCT No.: PCT/US2015/042055
§ 371 (c)(1),
(2) Date: Jan. 23, 2017

(87) PCT Pub. No.: WO2016/014975
PCT Pub. Date: Jan. 28, 2016

(65) Prior Publication Data
US 2017/0247387 A1 Aug. 31, 2017

Related U.S. Application Data

(60) Provisional application No. 62/029,006, filed on Jul. 25, 2014.

(51) Int. Cl.
| | |
|---|---|
| C07D 205/04 | (2006.01) |
| C07D 401/12 | (2006.01) |
| C07D 401/14 | (2006.01) |
| C07D 403/04 | (2006.01) |
| A61K 31/397 | (2006.01) |
| A61K 31/4427 | (2006.01) |
| A61K 31/4523 | (2006.01) |
| C07D 295/26 | (2006.01) |
| C07D 295/195 | (2006.01) |
| C07D 487/08 | (2006.01) |
| C07D 491/107 | (2006.01) |
| C07D 213/74 | (2006.01) |
| C07D 401/06 | (2006.01) |
| C07D 403/06 | (2006.01) |
| C07D 405/06 | (2006.01) |
| C07D 213/64 | (2006.01) |
| C07D 211/16 | (2006.01) |
| C07D 211/46 | (2006.01) |
| C07D 211/54 | (2006.01) |
| C07D 213/84 | (2006.01) |
| C07D 213/85 | (2006.01) |
| C07D 215/12 | (2006.01) |
| C07D 233/61 | (2006.01) |
| C07D 241/04 | (2006.01) |
| C07D 257/04 | (2006.01) |
| C07D 279/34 | (2006.01) |
| C07D 417/12 | (2006.01) |

(52) U.S. Cl.
CPC ....... *C07D 491/107* (2013.01); *C07D 205/04* (2013.01); *C07D 211/16* (2013.01); *C07D 211/46* (2013.01); *C07D 211/54* (2013.01); *C07D 213/64* (2013.01); *C07D 213/74* (2013.01); *C07D 213/84* (2013.01); *C07D 213/85* (2013.01); *C07D 215/12* (2013.01); *C07D 233/61* (2013.01); *C07D 241/04* (2013.01); *C07D 257/04* (2013.01); *C07D 295/195* (2013.01); *C07D 295/26* (2013.01); *C07D 401/06* (2013.01); *C07D 401/12* (2013.01); *C07D 401/14* (2013.01); *C07D 403/06* (2013.01); *C07D 405/06* (2013.01); *C07D 487/08* (2013.01)

(58) Field of Classification Search
CPC .. C07D 205/04; C07D 401/12; C07D 401/14; C07D 403/04
See application file for complete search history.

(56) References Cited

U.S. PATENT DOCUMENTS

| | | | | |
|---|---|---|---|---|
| 5,068,231 A | * | 11/1991 | Taylor, Jr. ............ | A61K 31/395 514/210.17 |
| 7,557,131 B2 | * | 7/2009 | Brown ................. | C07D 401/14 514/340 |

(Continued)

OTHER PUBLICATIONS

CA registry No. 1189941-49-8, entered into CA registry File on Oct. 25, 2009, supplied by Aurora Fine Chemicals.*

(Continued)

*Primary Examiner* — Emily A Bernhardt
(74) *Attorney, Agent, or Firm* — Hamilton, Brook, Smith & Reynolds, P.C.

(57) ABSTRACT

Disclosed are compounds that may be used to inhibit the action of fatty acid amide hydrolase (FAAH), monoacylglycerol lipase (MAGL) or dual FAAH/MAGL. More particularly, compounds of formula II

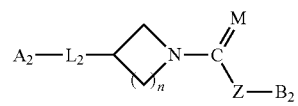

have utility in a variety of therapeutic uses such as treatment of pain, inflammation, neuropathy, or appetite disorder.

10 Claims, No Drawings

(56) References Cited

U.S. PATENT DOCUMENTS

| | | | | |
|---|---|---|---|---|
| 8,450,346 | B2* | 5/2013 | Roughley | C07D 205/04 514/210.17 |
| 2007/0135402 | A1* | 6/2007 | Habashita | A61K 31/437 514/210.01 |
| 2009/0062294 | A1 | 3/2009 | Apodaca et al. | |
| 2009/0082435 | A1 | 3/2009 | Piomelli et al. | |
| 2011/0039874 | A1 | 2/2011 | Makriyannis et al. | |
| 2013/0150346 | A1 | 6/2013 | Pearson et al. | |
| 2014/0066412 | A1 | 3/2014 | Breitenbucher et al. | |

OTHER PUBLICATIONS

CA registry No. 1185169-95-2, entered into CA registry File on Sep. 16, 2009, supplied by Aurora Fine Chemicals.*

CA registry No. 1185021-90-2, entered into CA registry File on Sep. 16, 2009, supplied by Aurora Fine Chemicals.*

Aurora Fine Chemicals Product Guide.1 page, retrieved from the Internet at http://www.aurorafinechemicals.com/abouthtml on Apr. 28, 2015.*

CA Registry No. 1422927-40-9 entered into CA Registry File on Mar. 11, 2013, supplied by ChemBridge Corporation.*

International Search Report; PCTUS2015042055; dated Jan. 8, 2016.

Written Opinion; PCTUS2015042055; dated Jan. 8, 2016.

Saario, SM et al. "Fatty Acid Amide Hydrolase Inhibitors from Virtual Screening of the Endocannabinoid System", vol. 49, 2006, pp. 4650-4656; abstract; p. 4652, tables 1-2.

Notification Concerning Transmittal of International Preliminary Report on Patentability for International Application No. PCT/US2015/042055 "Urea/Carbamates FAAH MAGL or Dual FAAH/MAGL Inhibitors And Uses Thereof", dated Feb. 9, 2017.

* cited by examiner

UREA/CARBAMATES FAAH MAGL OR DUAL FAAH/MAGL INHIBITORS AND USES THEREOF

CROSS REFERENCE TO RELATED APPLICATIONS

This application is a national stage filing under 35 U.S.C. § 371 of international PCT application PCT/US2015/042055, filed on Jul. 24, 2015, which claims the benefit of U.S. Provisional Application No. 62/029,006, filed Jul. 25, 2014, the contents of which are hereby incorporated herein by reference.

STATEMENT REGARDING FEDERALLY SPONSORED RESEARCH OR DEVELOPMENT

This invention was made with government support under Grant Number DA007215 awarded by the National Institutes of Health, and Grant Number DE-FG02-00ER45852 awarded by the Department of Energy. The government has certain rights in the invention.

FIELD OF THE INVENTION

The present disclosure relates generally to ureas and carbamates that inhibit FAAG, MAGL or dual FAAH/MAGL, and to the manufacture thereof and uses thereof. For example, the compounds can be used for treating pain, inflammation, neuropathy, neurodegenerative disease, anxiety disorder, motor function disorder, fertility disorder, appetite disorder, THC-dependence, metabolic disorder, movement disorder, and chemotherapy induced nausea and vomiting (CINV) and cancer.

BACKGROUND

Presently, two $G_{i/o}$, protein coupled cannabinoid receptors have been characterized in mammals and other organisms (Devane et al, *Brain Mol. Pharmacol.* (1988) 34: 605-613, Matsuda et at, *Nature* (1990) 346: 561-564). Cannabinoid receptor 1 (CB1) is a central receptor found in the mammalian brain and a number of other sites in peripheral tissues; and CB2, a peripheral receptor found principally in cells related to the immune system. Cannabinergic ligands can bind to the CB1 and/or CB2 receptors in an individual or animal. In vitro methods for assaying the ability of a compound to bind to CB1 and/or CB2 receptors are known (Devane et al, *Brain Mol. Pharmacol.* (1988) 34: 605-613). Results from the in vitro assay correlate with and predict the in vivo ability of that compound to bind to CB1 and/or CB2 receptors and modulate their function(s).

When introduced in an individual or animal some of these cannabinergic ligands can bind to and directly modulate (activate or deactivate) the CB1 and/or CB2 receptors. Many physiological effects have been associated with direct modulation of the CB1 and/or CB2 receptors in an individual or animal (Jonsson et al. *Basic and Clinical Pharmacol. Toxic.* (2006) 98: 124-134), Examples of cannabinergic ligands include (−)-Δ⁹-tetrahydrocannabinol ((−)-Δ⁹-THC), the principal bioactive constituent of *cannabis* and exogenous ligand for the cannabinoid CB1 and CB2 receptors) and other synthetic cannabinergic analogs. The major endogenous ligands for the CB receptors are N-arachidonoyl ethanolamine (anandamide, AEA) and 2-arachidonoylglycerol (2-AG) (Devane et al, *Science* (1992) 258: 1946-1949, Mechoulam et al *Biochem. Pharmacol.* (1995) 50: 83-90).

The magnitude and duration of in vivo CB1 and/or CB2 receptor modulation by endocannabinoids AEA and 2-AG is relatively short, presumably due to rapid inactivation process involving endocannabinoid deactivating proteins. Anandamide for example, is inactivated via fatty acid amide hydrolase (FAAH) mediated hydrolysis (Deutsch et al. *Biochem. Pharmacol.* 1993, 46, 791-796). FAAH belongs to the amidase signature (AS) super family of serine hydrolases and in contrast to the classical serine-histidine-aspartate triad found in most serine hydrolases, the catalytic machinery of this enzyme is a serine-serine-lysine catalytic triad. FAAH has been isolated, molecularly cloned and its 2.8 Å crystal structure was recently reported. 2-arachidonoylglycerol (2-AG), 1-arachidonoylglycerol, arachidonamide and the corresponding simple ester methyl arachidonate are also substrates for FAAH.

Moreover, studies have demonstrated that this enzyme not only can hydrolyze anandamide into arachidonic acid and ethanolamine it can also catalyze reverse synthesis from the two hydrolysis components. Also notable is FAAH's ability to hydrolyze several bioactive fatty acid amides not belonging to the endocannabinoid family, for example, the sleep inducing lipid oleamide, the appetite-suppressing agent oleoylethanolamine, the related. 1-oleoylglycerol, and the peripheral analgesic and anti-inflammatory mediator palmitoylethanolamine. Despite the fact that a range of fatty acid amides, ethanolamides and esters are hydrolyzed by FAAH, this enzyme appears to work most effectively on arachidonoyl and oleoyl substrates.

Although FAAH has been shown to also catalyze hydrolysis of 2-arachidonoylglycerol in vitro, a distinct enzyme, monoacylglycerol lipase (MAGL) plays the predominant role in catalyzing 2-AG (the most abundant endocannabinoid) hydrolysis in vivo (Karlsson et al *J. Biol. Chem.* (1997) 272: 27218-27223). Monoacylglycerol lipase, also known as MAGL, MAG lipase or MAGL is a serine hydrolase that is also notable for its ability to hydrolyze several bioactive fatty acid glyceryl esters not belonging to the endocannabinoid family, for example, 2-oleoylglycerol and 2-palmitoyl glycerol. MAGL plays dual roles in physiologic processes, encompassing regulating endocannabinoid tone as well as lipogenesis (Dinh et al *Proceedings of the National Academy of Sciences of the United States of America* (2002) 99: 10819; Schlosburg et al *Nature neuroscience* (2010) 13: 1113. Site-directed mutagenesis studies (Zvonok et at *Chemistry & biology* (2008) 15: 854; Zvonok et at *Journal of Proteome Research* (2008) 7: 2158) as well as X-ray crystal structure of a complex with its ligand have identified the enzyme's catalytic triad as Ser$^{122}$-Asp$^{239}$-His$^{269}$ (Labar et at *Chembiochem: a European journal of chemical biology* (2010) 11: 218; Schalk-Hihi et at *Protein science: a publication of the Protein Society* (2011) 20: 670.

Some compounds can inhibit the inactivation of cannabinergic ligands by FAAH, by MAGL, or by dual FAAH/MAGL. These compounds may not bind to, or may have lesser affinity for, the cannabinoid receptors. Thus, the physiological action for such compounds is inhibition of fatty acid amide hydrolase (FAAH) and not direct modulation of the CB' and/or CB2 receptors. The inactivation of endocannabinoids by FAAH, MAGL, or dual FAAH/MAGL can be inhibited. These inhibitors may not bind to, or may have lesser affinity for, the cannabinoid receptors. Thus, the physiological action for such compounds is inhibition of FAAH and or MAGL and not direct modulation of the CB1 and/or CB2 receptors. Inhibition of FAAH, MAGL, or dual FAAH/MAGL in an individual or animal will slow the normal degradation and inactivation of endogenous cannabinoid ligands by FAAH or MAGL hydrolysis and allow higher levels of those endogenous cannabinergic ligands to remain present in that individual or animal. These higher levels of endocannabinoid induce increased stimulation of the cannabinoid CB1 and CB2 receptors and produce physiological effects related to the activation of the cannabinoid receptors. They will also enhance the effects of other exogenous cannabinergic ligands and allow them to produce their effects at lower concentrations as compared to systems in which FAAH, MAGL, or dual FAAH/MAGL action is not inhibited. Thus, a compound that inhibits the inactivation of endogenous cannabinoid ligands by FAAH, MAGL, or dual FAAH/MAGL may increase the levels of endocannabinoids and, thus, enhance the activation of cannabinoid receptors. The compound may not directly modulate the cannabinoid receptors but has the effect of indirectly stimulating the cannabinoid receptors by increasing the in vivo levels of endocannabinoid ligands. It may also enhance the effects and duration of action of other exogenous cannabinergic ligands that are administered in order to elicit a cannabinergic response.

Marijuana-like cannabinoids, in addition to acting at cannabinoid receptors also affect cellular membranes, thereby producing undesirable side effects such as drowsiness, impairment of monoamide oxidase function and impairment of non-receptor mediated brain function. The addictive and psychotropic properties of some cannabinoids also limit their therapeutic value. Compounds that inhibit FAAH, MAGL, or dual FAAH/MAGL activity may indirectly provide desirable pharmacological properties while avoiding the disadvantages incurred by use of cannabinergic ligands that directly activate the cannabinoid receptors. Compounds that inhibit FAAH and or MAGL activity provide an alternative mechanism for indirectly stimulating cannabinoid receptors and may provide desirable pharmacological properties without the addictive and psychotropic properties as well as other undesirable properties associated with exogenous cannabinergic ligands.

FAAH, MAGL, or dual FAAH/MAGL inhibitory compounds comprise two pharmacophoric subunits responsible for enzyme recognition and inactivation. The "inhibition" subunit typically comprises an activated carbonyl group and the "binding" subunit, which is linked to the inhibition subunit, enhances the inhibitory action of the molecule.

Conditions that may be treated by modulation of the CB1/CB2 cannabinoid receptors include for example: high blood pressure disease or hypertension; peripheral vascular diseases; coronary artery disease; abnormal heart rate; pulmonary hypertension; ocular hypertension or glaucoma; tumor growth; to prevent or reduce inflammation; to provide neuroprotection; to treat epilepsy; to treat nausea, such as associated with cancer chemotherapy; AIDS wasting syndrome as well as other ailments in which cannabinoid system is implicated.

SUMMARY OF THE INVENTION

The present disclosure relates to compounds of general formulas I-III to inhibit FAAH, MAGL or dual FAAH/MAGL, their methods of preparation and uses thereof. In some embodiments the compounds are FAAH inhibitors. In other embodiments the compounds comprise MAGL inhibitors and in further embodiments the compounds comprise dual FAAH/MAGL inhibitors. Some aspects of the present disclosure provide use of compounds of general formulas I-III to inhibit FAAH, MAGL or dual FAAH/MAGL.

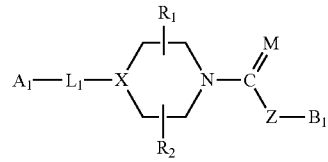

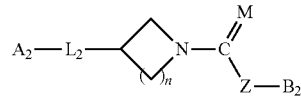

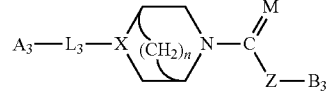

The disclosures of the present application include methods for indirect modulation of cannabinoid receptors, and methods for treating various disorders in a subject. One aspect of the application is directed to a method of modulating cannabinoid receptors in a biological sample. In this method, the level of a cannabinergic ligand in the biological sample is measured. Then, the biological sample is contacted with compounds of formulas I-III. The level of the cannabinergic ligand in the contacted sample is then measured, to determine if the level of the cannabinergic ligand in the contacted sample is the same or greater than the level of the cannabinergic ligand in the uncontacted sample.

In a particular embodiment, the enzyme inhibited by compounds of formulas I-III is FAAH and the cannabinergic ligand is anadamide. In another embodiment, the enzyme inhibited is MAGL and the cannabinergic ligand is 2-arachidonoylglycerol (2-AG). In a further certain embodiment, the enzymes inhibited are dual FAAH and MAGL and the cannabinergic ligands are anadamide and 2-AG. In some embodiments, effects of modulating CB1/CB2 receptors are assessed.

Inhibition of FAAH, MAGL or dual FAAH/MAGL will slow the normal degradation and inactivation of endogenous cannabinoid ligands by FAAH, MAGL or dual FAAH/MAGL hydrolysis and allow higher levels of endogenous anadamide and 2-arachidonoylglycerol to remain present. These higher levels of endocannabinoid ligands provide increased stimulation of the cannabinoid CB1 and CB2 receptors and produce physiological effects related to the activation of the cannabinoid receptors. Compounds of formulas I-III will also enhance the effects of other exogenous cannabinergic ligands (e.g. $\Delta^9$-THC) and allow them to produce effects at lower concentrations as compared to systems in which FAAH, MAGL or dual FAAH/MAGL action is not inhibited. The compound may not directly modulate the cannabinoid receptors but has the effect of indirectly stimulating the cannabinoid receptors by increasing the levels of endocannabinoid ligands. FAAH, MAGL or dual FAAH/MAGL inhibition induces CB1, CB2 or dual CB1/CB2-dependent beneficial effects that may be used to prevent or reduce inflammation; to provide neuroprotection; treat THC-dependence; to treat cancer; to treat chemotherapy induced nausea and vomiting (CINV) associated with cancer chemotherapy; to treat AIDS wasting syndrome as well as other ailments in which cannabinoid system is implicated.

A further aspect of the invention is directed to treating certain disorders in a subject e.g., neuropathic pain. The method comprises administering a therapeutically effective amount of a compound of formula I, II or III to the subject. The administration of the compound treats the neuropathy of the subject. In some embodiments the neuropathy is neuropathic pain, diabetic neuropathy, neuropathy caused by chemotherapeutic agents, central pain, peripheral pain, pellargic neuropathy, alcoholic neuropathy, beriberi neuropathy, burning pain syndrome. In yet other embodiments, the neuropathy is a neurodegenerative disease. In particular embodiments, the neurodegenerative disease is multiple sclerosis, Parkinson's disease, Huntington's chorea, Alzheimer's disease, amyotrophic lateral sclerosis, In particular embodiments, the invention is directed to treating mood disorder, sleep disorder, gastrointestinal motility disorder, irritable bowel syndrome, diarrhea, cardiovascular disease, hypertension, osteoporosis, osteoarthritis, emesis, epilepsy, a mental disorder, schizophrenia, depression, glaucoma, cachexia, insomnia, traumatic brain injury, spinal cord injury, seizures, excitotoxin exposure, ischemia, or AIDS wasting syndrome.

An additional aspect of the application is directed to a method of treating a motor function disorder in a subject. In particular embodiment the motor function disorder is Tourette's syndrome. The method comprises administering to the subject a therapeutically effective amount of a compound of formula I, II or III. The administration of the compound treats the motor function disorder of the subject. An additional aspect of the disclosure is directed to a method of treating a fertility disorder in a subject. The method comprises administering to the subject a therapeutically effective amount of a compound of formula I, II or III. The administration of the compound treats the fertility disorder of the subject.

Another aspect of the application is directed to a method of treating an anxiety disorder in a subject. The method comprises administering to the subject a therapeutically effective amount of a compound of formula I, II or III. The administration of the compound treats the anxiety disorder of the subject. In certain embodiments, the anxiety disorder is panic disorder, acute stress disorder, post-traumatic stress disorder, substance-induced anxiety disorder, obsessive compulsive disorder, agoraphobia, specific phobia, or social phobia.

In yet another aspect, the disclosure is directed to a method of treating an appetite disorder in a subject. The method comprises administering to the subject a therapeutically effective amount of a compound of formula I, II or III. The administration of the compound treats the appetite disorder of the subject.

In another embodiment administration of the compound treats the metabolic disorder in a subject. The method comprises administering to the subject a therapeutically effective amount of a compound of formula I, II or III. The administration of the compound treats the metabolic disorder of the subject.

In still another aspect, the disclosure is directed to a method of treating movement disorder in a subject. The method comprises administering to the subject a therapeutically effective amount of a compound of formula I, II or III. The administration of the compound treats the movement disorder of the subject. Another aspect of the disclosure is directed to a method of treating cancer in a subject. The method comprises administering to the subject a therapeutically effective amount of a compound of formula I, II or III. The administration of the compound treats the cancer of the subject. A further aspect of the invention is directed to treating nausea induced by chemotherapy The method comprises administering to the subject a therapeutically effective amount of a compound of formula I, II or III. The administration of the compound treats nausea induced by chemotherapy of the subject.

Compounds of formula I-III can affect endocannabinoid levels in the CNS by inhibiting FAAH and or MAGL activities. In addition to these central mechanisms, peripheral FAAH and or MAGL can also be inhibited. Administration of compounds that are restricted to the peripheral tissues can selectively inhibit FAAH and or MAGL in these tissues. Some of the compounds in this disclosure can selectively inhibit FAAH and or MAGL in peripheral system.

DETAILED DESCRIPTION

Compounds
This invention relates to compounds of Formulas

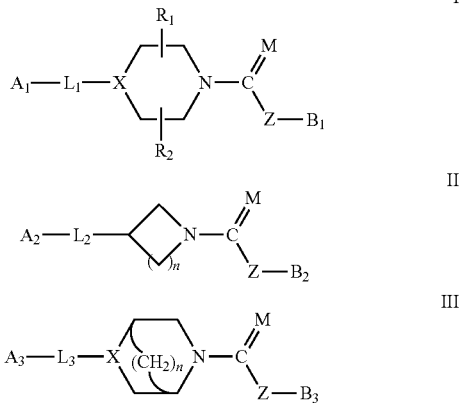

In a particular embodiment this invention relates to compounds of Formula I wherein
X=CH, N;
M=O, S;
Z=O, NH, or none, when Z is none B1 is directly attached to C=M;
R1=—H, -alkyl;
R2=—H, -alkyl, where alkyl is saturated C1-10 hydrocarbon, which may be straight or branched chain;
L1 is selected from —(CH2)n-, —O(CH2)n-, —O—, —SO2-, —C(=O)—, when X is N, or —(CH2)n-, —(CH2)nO—, —O—, —CH=CH—, —CONH—, —S—, —S(=O)—, —SO2-, —NH—, —NR1- when X is CH, where n=0-6;
A1 is selected from aryl, heteroaryl, benzhydryl, fluorenyl, aryl(aryl)methyl, aryl(phenyl)methyl, aryl(alkyl)methyl, aryl(cycloalkyl)methyl and each aryl, heteroaryl or fluorenyl group may be unsubstituted, mono or di-substituted with following moieties; —NO2, —CN, —OH, -alkyl, —O-alkyl, -halogen, —CF3, —OCF3, —S-alkyl, —OPh, -Ph, —S(O)— alkyl, —SO2-alkyl, —CO2-alkyl, —COOH, —NHR3, —NR3R4, —NR3SO2R4, —NO2, —CN, —CONR3R4; morpholino; thiomorpholino, 1,1-dioxothiomorpholine, oxothiomorpholino, R3 and R4 are independently selected from —H or -alkyl, cycloalkyl;

$B_1$ can be selected from aryl, heteroaryl, and each aryl or heteroaryl group may be unsubstituted or substituted at a carbon ring member with one or two moieties as defined below;

halogen —NO$_2$, —CN, —OH, —NH$_2$, —CONH$_2$, —O-aryl, —CF$_3$, —OCF$_3$, —OCF$_2$H, —SCF$_3$, —OPh;

where n, m=1-3;
$Q_1$ is selected from CO, —CH(OH), O, S, S(O), SO$_2$;
$R_5$ is selected from H, OH, halogen,
$R_6$ is selected from H, —CN, —OH, —OMe, —CF$_3$, —OCF$_3$, —OBn, —CONH$_2$, —SO$_2$NH$_2$, —COOH;
B1 also encompasses:

where Ar can be aryl or heteroaryl containing 1 to 3 heteroatoms;
W1 is either CH or N;
W2 is —CH2, —CH—Ar or —N—Ar;
R7 is selected from monocyclic heteroaryl ring containing 1 to 3 heteroatoms and each aryl or heteroaryl ring can be substituted with one or two groups as defined below:
halogen —NO$_2$, —CN, —OH, —NH$_2$, —CONH$_2$, —O-aryl, —CF$_3$, —OCF$_3$, —OCF$_2$H, —SCF$_3$, —OPh; R$_8$ is selected from —H, —OH, -halogen.

Particularly useful compounds of Formula I include those compounds wherein: $L_1$ is selected from —(CH$_2$)$_n$—, —O(CH$_2$)$_n$—, —(CH$_2$)$_n$O—, —SO$_2$—, —C(=O)—, when X is N, or —(CH$_2$)$_n$—, (CH$_2$)$_n$O—, —O—, —CH=CH—, —CONH—, —S—, —S(=O)—, —SO$_2$—, —NH—, —NR$_1$— when X is CH, where n=0-3; more particularly where n=0-2;

The following compounds of Formula I are also particularly useful, wherein:
M=O;
$L_1$ is selected from —(CH$_2$)$_n$—, —SO$_2$, —C(=O)—, when X is N, or —(CH$_2$)$_n$O—, O, S, —S(O)—, SO$_2$, when X is CH, where n=0-2;
$A_1$ is selected from aryl, heteroaryl, benzhydryl, fluorenyl, aryl(aryl)methyl, aryl(phenyl)methyl, aryl(alkyl)methyl, aryl(cycloalkyl)methyl and each aryl, heteroaryl or fluorenyl group may be unsubstituted, mono or di-substituted with following moieties;
-alkyl, —O-alkyl, -halogen, —CF$_3$, —OPh, -Ph, morpholino; thiomorpholino, 1,1-dioxothiomorpholine;
$B_1$ can be selected from aryl, heteroaryl, and each aryl or heteroaryl group may be unsubstituted or substituted at a carbon ring member with one or two moieties as defined below;
—H, -halogen —CN, —OH, —OMe, —CONH2, —CF3;

Where n, m=2; and Q1 is SO2;
R6 is selected from —H, -halogen —CN, —OH, —OMe, —CONH2, —CF3;
$B_1$ also encompasses:

and the other substituents are the same as set forth above.
In accordance with another aspect, the present invention relates to compounds of formula IA (IA)

wherein
X=CH, N;
$R_1$=—H, -alkyl;
$R_2$=—H, -alkyl, where alkyl is saturated $C_{1-10}$ hydrocarbon, which may be straight or branched chain;
n=0-3;
$A_1$ is selected from aryl, heteroaryl, benzhydryl, fluorenyl, aryl(aryl)methyl, aryl(phenyl)methyl, aryl(alkyl)methyl, aryl(cycloalkyl)methyl and each aryl, heteroaryl or fluorenyl group may be unsubstituted, mono or di-substituted with following moieties:

—$NO_2$, —CN, —OH, -alkyl, —O-alkyl, -halogen, —$CF_3$, —$OCF_3$, —S-alkyl, —OPh, -Ph, —S(O)-alkyl, —$SO_2$-alkyl, —$CO_2$-alkyl, —COOH, —$NHR_3$, —$NR_3R_4$, —$NR_3SO_2R_4$, —$NO_2$, —CN, —$CONR_3R_4$; morpholino; thiomorpholino, 1,1-dioxothiomorpholine, oxothiomorpholino, $R_3$ and $R_4$ are independently selected from —H or -alkyl, cycloalkyl; and $R_6$ is selected from H, —CN, —OH, —OMe, —$CF_3$, —$OCF_3$, —OBn, —$CONH_2$, —$SO_2NH_2$, —COOH.

In accordance with particular embodiments, the compounds of Formula IA are those in which X=N and n=0-1. In accordance with certain embodiments, $R_6$ is selected from —H, —CN, —$CONH_2$, —$CF_3$. In accordance with particularly useful embodiments, $A_1$ is selected from the group consisting of: phenoxyphenyl, quinolinyl, phenyl, fluorenyl, pyridinyl, and biphenyl.

In accordance with another aspect, the present invention relates to compounds of formula IB

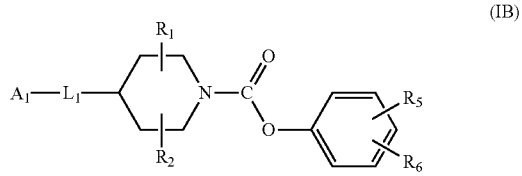

(IB)

wherein $R_1$=—H, -alkyl;

$R_2$=—H, -alkyl, where alkyl is saturated $C_{1-10}$ hydrocarbon, which may be straight or branched chain;

$L_1$ is selected from a double bond, —$(CH_2)_n$—, —O—, —CH=CH—, —CONH—, —S—, —S(=O)—, —$SO_2$—, —NH—, —$NR_1$—, where n=0-6;

$A_1$ is selected from aryl, heteroaryl, benzhydryl, fluorenyl, aryl(aryl)methyl, aryl(phenyl)methyl, aryl(alkyl)methyl, aryl(cycloalkyl)methyl and each aryl, heteroaryl or fluorenyl group may be unsubstituted, mono or di-substituted with following moieties; —$NO_2$, —CN, —OH, -alkyl, —O-alkyl, -halogen, —$CF_3$, —$OCF_3$, —S-alkyl, —OPh, -Ph-S(O)-alkyl, —$SO_2$-alkyl, —$CO_2$-alkyl, —COOH, —$NHR_3$, —$NR_3R_4$, —$NR_3SO_2R_4$, —$NO_2$, —CN, —$CONR_3R_4$;

morpholino; thiomorpholino, 1,1-dioxothiomorpholine, oxothiomorpholino, $R_3$ and $R_4$ are independently selected from —H or -alkyl, -cycloalkyl;

$R_5$ is selected from —H, —OH, halogen, $R_6$ is selected from —H, —CN, —OH, —OMe, —$CF_3$, —$OCF_3$, —OBn, —$CONH_2$, —$SO_2NH_2$, —COOH.

In certain embodiments, $L_1$ is selected from a double bond and —$(CH_2)_n$— and n=0-1. In accordance with some embodiments, $R_5$ is selected from —H, halogen; and $R_6$ is selected from —H, —CN, —$CONH_2$, —$CF_3$. In accordance with particularly useful compounds, $A_1$ is selected from the group consisting of: phenyl, benzyl and benzhydryl.

Examples of certain useful compounds of Formula I include:

Example 1: (S)—N-(3'-carbamoyl-[1,1'-biphenyl]-3-yl)-3-methyl-4-(quinolin-2-ylmethyl) piperazine-1-carboxamide Example 2: (R)—N-(3'-carbamoyl-[1,1'-biphenyl]-3-yl)-3-methyl-4-(quinolin-2-ylmethyl)piperazine-1-carboxamide Example 3: (S)—N-(3'-cyano-[1,1'-biphenyl]-3-yl)-2-methyl-4-(3-phenoxybenzyl)piperazine-1-carboxamide Example 4: (S)—N-(3'-carbamoyl-[1,1'-biphenyl]-3-yl)-2-methyl-4-(3-phenoxybenzyl)piperazine-1-carboxamide Example 5: (S)—N-(5-(3-cyanophenyl)pyridin-3-yl)-2-methyl-4-(3-phenoxybenzyl)piperazine-1-carboxamide Example 6: N-(3'-carbamoyl-[1,1'-biphenyl]-3-yl)-4-(quinolin-3-ylmethyl)piperazine-1-carboxamide Example 7: N-(3'-carbamoyl-[1,1'-biphenyl]-3-yl)-4-phenylpiperidine-1-carboxamide Example 8: N-(3'-carbamoyl-[1,1'-biphenyl]-3-yl)-4-(9H-fluoren-9-yl)piperazine-1-carboxamide Example 9: N-(3'-carbamoyl-[1,1'-biphenyl]-3-yl)-4-(pyridin-2-yl)piperazine-1-carboxamide Example 10: 4-([1,1'-biphenyl]-4-ylmethyl)-N-(3'-carbamoyl-[1,1'-biphenyl]-3-yl)piperazine-1-carboxamide Example 11: N-(3'-carbamoyl-[1,1'-biphenyl]-3-yl)-4-phenylpiperazine-1-carboxamide Example 12: N-(3'-carbamoyl-[1,1'-biphenyl]-3-yl)-4-(quinolin-2-ylmethyl)piperazine-1-carboxamide Example 13: N-(3'-cyano-[1,1'-biphenyl]-3-yl)-4-(quinolin-2-ylmethyl)piperazine-1-carboxamide Example 14: N-(3-phenoxyphenyl)-4-(quinolin-2-ylmethyl)piperazine-1-carboxamide Example 15: N-(3'-cyano-[1,1'-biphenyl]-3-yl)-4-phenylpiperidine-1-carboxamide Example 16: N-(5-(3-cyanophenyl)pyridin-3-yl)-4-phenylpiperidine-1-carboxamide Example 17: 4-([1,1'-biphenyl]-3-ylmethyl)-N-(3'-cyano-[1,1'-biphenyl]-3-yl)piperazine-1-carboxamide Example 18: N-(3'-carbamoyl-[1,1'-biphenyl]-3-yl)-4-(3-phenoxybenzyl)piperazine-1-carboxamide Example 19: (S)—N-(3'-cyano-[1,1'-biphenyl]-3-yl)-3-methyl-4-(quinolin-2-ylmethyl)piperazine-1-carboxamide Example 20: N-(3'-cyano-[1,1'-biphenyl]-3-yl)-4-oxospiro[chromane-2,4'-piperidine]-1-carboxamide Example 21: (S)-(4-([1,1'-biphenyl]-3-ylmethyl)-3-methylpiperazin-1-yl)(4-phenyl-1H-imidazol-1-yl)methanone Example 22: (S)-(4-bromo-1H-imidazol-1-yl)(2-methyl-4-(3-phenoxybenzyl)piperazin-1-yl)methanone Example 23: (2-methyl-4-phenylpiperazin-1-yl)(4-phenyl-1H-imidazol-1-yl)methanone Example 24: (3-methyl-4-phenylpiperazin-1-yl)(4-phenyl-1H-imidazol-1-yl)methanone Example 25: (3-methyl-4-(p-tolyl)piperazin-1-yl)(4-phenyl-1H-imidazol-1-yl)methanone Example 26: (4-(3-(benzyloxy)phenyl)-3-methylpiperazin-1-yl)(4-phenyl-1H-imidazol-1-yl)methanone Example 27: (4-(3-hydroxyphenyl)-3-methylpiperazin-1-yl)(4-phenyl-1H-imidazol-1-yl)methanone Example 28: (4-(bis(4-fluorophenyl)methyl)piperazin-1-yl)(4-bromo-1H-imidazol-1-yl)methanone Example 29: (4-(bis(4-fluorophenyl)methyl)piperazin-1-yl)(4-phenyl-1H-imidazol-1-yl)methanone Example 30: (4-benzhydrylpiperazin-1-yl)(4-phenyl-1H-imidazol-1-yl)methanone Example 31: (4-benzhydrylpiperazin-1-yl)(5-benzyl-1H-tetrazol-1-yl)methanone Example 32: (5-benzyl-1H-tetrazol-1-yl)(4-(bis(4-fluorophenyl)methyl)piperazin-1-yl)methanone Example 33: (3-(Carbomethoxy)-1H-1,2,4-triazol-1-yl)(4-(bis(4-fluorophenyl)methyoxy)piperidin-1yl)methanone Example 34: 4'-(4-bromo-1H-imidazole-1-carbonyl)spiro[chromane-2,1'-cyclohexan]-4-one Example 35: 3-Cyanophenyl 4-(2-methyl-1-phenylpropyl)piperazine-1-carboxylate
Example 36: 3-cyanophenyl 4-(1-phenylethyl)piperazine-1-carboxylate
Example 37: 3-cyanophenyl 4-(cyclopentyl(phenyl)methyl)piperazine-1-carboxylate
Example 38: 3-cyano-5-hydroxyphenyl 4-benzhydrylpiperazine-1-carboxylate
Example 39: 6-chloropyridin-2-yl 4-benzhydrylpiperazine-1-carboxylate
Example 40: 3-cyanophenyl 4-(bis(4-fluorophenyl)methyl)piperazine-1-carboxylate
Example 41: 3-cyanophenyl 4-(9H-fluoren-9-yl)piperazine-1-carboxylate
Example 42: 4-cyanopyridin-2-yl 4-(9H-fluoren-9-yl)piperazine-1-carboxylate
Example 43: 3-cyanopyridin-2-yl 4-(9H-fluoren-9-yl)piperazine-1-carboxylate
Example 44: 3-Cyanophenyl 4-benzhydrylpiperazine-1-carboxylate
Example 45: 5-Cyano-2-fluorophenyl 4-benzylpiperidine-1-carboxylate
Example 46: 3-Cyanophenyl 4-benzhydrylpiperidine-1-carboxylate
Example 47: 3-cyanophenyl 4-(diphenylmethylene)piperidine-1-carboxylate
Example 48: 3-(methoxycarbonyl)phenyl 4-(diphenylmethylene)piperidine-1-carboxylate
Example 49: 5-cyano-2-fluorophenyl 4-benzhydrylpiperidine-1-carboxylate
Example 50: 3-cyano-5-hydroxyphenyl 4-benzhydrylpiperidine-1-carboxylate
Example 51: 6-Chloropyridin-2-yl 4-(benzhydryl)piperidine-1-carboxylate
Example 52: 3-cyanophenyl 4-benzylpiperidine-1-carboxylate
Example 53: 3-cyanophenyl 4-(4-chlorophenyl)(2-chloropyridin-3-yl)methoxy)piperidine-1-carboxylate
Example 54 6-Chloropyridin-2-yl 4-(benzhydryl)piperidine-1-carboxylate
Example 55: 3-(methoxycarbonyl)phenyl 4-(benzhydryloxy)piperidine-1-carboxylate
Example 56: 5-cyano-2-fluorophenyl 4-(benzhydryloxy)piperidine-1-carboxylate
Example 57: 6-chloropyridin-2-yl 4-(benzhydryloxy)piperidine-1-carboxylate
Example 58: 3-cyanophenyl 4-(benzhydryloxy)piperidine-1-carboxylate
Example 59: 3-Cyanophenyl 4-(4-bromophenylsulfonyl)piperidine-1-carboxylate
Example 60: 5-Cyano-2-fluorophenyl 4-(4-bromophenylsulfonyl)piperidine-1-carboxylate
Example 61: 5-Cyano-2-methylphenyl 4-(4-bromophenylsulfonyl)piperidine-1-carboxylate
Example 62: 5-Cyano-2-methoxyphenyl 4-(4-bromophenylsulfonyl)piperidine-1-carboxylate
Example 63: 2,6-Difluorophenyl 4-(4-bromophenylsulfonyl)piperidine-1-carboxylate
Example 64: 4-bromophenyl 4-tosylpiperazine-1-carboxylate
Example 65: 2,6-difluorophenyl 4-tosylpiperazine-1-carboxylate
Example 66: 4'-fluoro-3-hydroxy-[1,1'-biphenyl]-4-yl 4-tosylpiperazine-1-carboxylate
Example 67: N-(3-(1,1-dioxidothiomorpholino)phenyl)-4-phenylpiperazine-1-carboxamide
Example 68: N-(3-(1,1-dioxidothiomorpholino)phenyl)-4-phenylpiperidine-1-carboxamide
Example 69: 3-(1,1-dioxidothiomorpholino)phenyl 4-phenylpiperazine-1-carboxylate
Example 70: 3-(1,1-Dioxothiomorpholin-4-yl)phenyl 4-phenylpiperidine-1-carboxylate
Example 71: 3-(1,1-dioxidothiomorpholino)phenyl 4-(3-phenoxybenzyl)piperazine-1-carboxylate
Example 72: 3-(1,1-dioxidothiomorpholino)phenyl 4-(quinolin-2-ylmethyl)piperazine-1-carboxylate
Example 73: 3-(1,1-dioxidothiomorpholino)phenyl 2-methyl-4-phenylpiperazine-1-carboxylate In another embodiment, this invention relates to compounds of Formula II

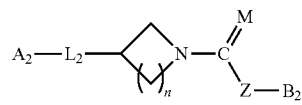

Wherein
M=O, S;
Z=O, NH, or none; when Z=none $B_2$ is directly attaches to C=M;
n=1-2
$L_2$ is selected from

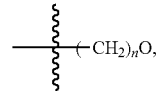

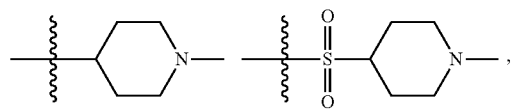

—S—, —S(O)—, $SO_2$, —NH—, n=0-2, more particularly n=0-1;

$A_2$ is selected from aryl, heteroaryl, fluoren-9-yl, aryl(alkyl)methyl, aryl(cycloalkyl)methyl, heteroaryl(alkyl)methyl, or heteroaryl(cycloalkyl)methyl and each aryl, heteroaryl or fluore-9-nyl group may be unsubstituted, or substituted with one or two moieties as defined below;

—OH, -alkyl, —O-alkyl, -halogen, —$CF_3$, —$OCF_3$, —S-alkyl, —OPh, -Ph-S(O)-alkyl, —$SO_2$-alkyl, —$CO_2$-alkyl, —COOH, —NHR, —$NR_3R_4$, —$NR_3SO_2R_4$, —$NO_2$, —CN, —$CONR_3R_4$, -alkynyl, morpholino, thiomorpholino, 1,1-dioxothiomorpholine, 1-oxothiomorpholino;

$R_3$ and $R_4$ are independently selected from —H or -alkyl, cycloalkyl;

$B_2$ can be selected from aryl or heteroaryl groups, and each aryl or heteroaryl group may be unsubstituted or substituted with one or two moieties as defined below:

-halogen —$NO_2$, —CN, —OH, —$NH_2$, —$CONH_2$, —O-aryl, —$CF_3$, —$OCF_3$, —$OCF_2H$, —$SCF_3$;

B$_2$ is also encompassing

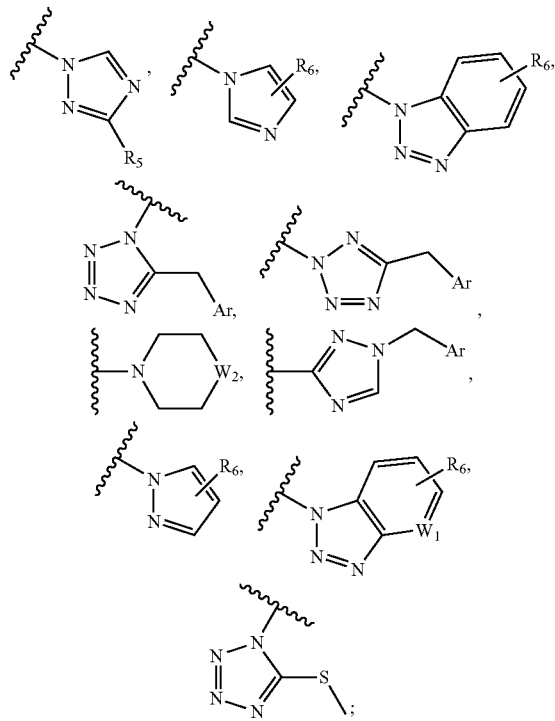

wherein W$_1$ is either CH or N;
W$_2$ is selected from CH$_2$, O, SO$_2$, CHAr, or NAr;
Ar can be aryl or heteroaryl containing 1 to 3 heteroatoms;
R$_5$ is selected from —H, -halogen —NO$_2$, —CN, —OH, -Ph, —COOMe; —NH$_2$, —CONH$_2$, —O-aryl, —CF$_3$, —OCF$_3$, —OCF$_2$H, —SCF$_3$;
R$_6$ is selected from monocyclic heteroaryl ring containing 1 to 3 heteroatoms, and the heteroaryl ring can be substituted with one or two groups, as defined below: —CN, —OH, —OMe, —CF$_3$, —OCF$_3$, —OBn, —CONH$_2$, —SO$_2$NH$_2$, —COOH -halogen, or
wherein M can be selected from O or S,

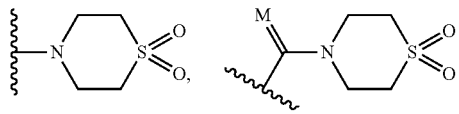

Particularly useful compounds of Formula II include those compounds wherein
Z=O, NH, or none; when Z=none B$_3$ is directly attaches to C=M;
n=1-2; and the remaining substituents are as described above.
Still more particularly useful compounds of Formula II include those compounds wherein

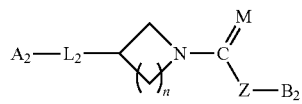

M=O;
L$_2$ is selected A$_2$-(CH$_2$)—O—, —O—, —S—, —S(O)—, SO$_2$, —NH—, n=0-1;

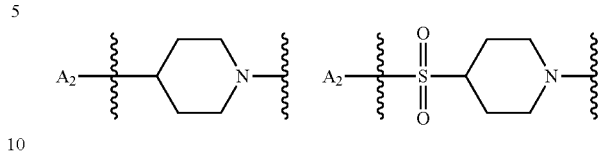

A$_2$ is selected from aryl, heteroaryl, and each aryl, heteroaryl group may be unsubstituted, or substituted with one or two moieties as defined below:
-halogen;
B$_2$ can be selected from aryl or heteroaryl groups, and each aryl or heteroaryl group may be unsubstituted or substituted with one or two moieties as defined below:
-halogen —CN, —CONH$_2$, —CF$_3$;
B$_2$ also encompasses:

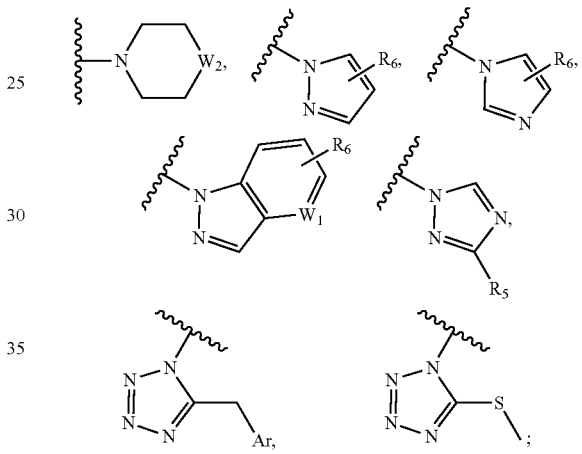

R$_5$ is selected from —H, -Ph, —COOMe;
R$_6$ is selected from monocyclic heteroaryl ring containing 1 to 3 heteroatoms, and the heteroaryl ring can be substituted with one or two groups, as defined below:
halogen.
Examples of particularly useful compounds of Formula II include:
Example 74 3-Cyanophenyl 3-(4-chlorobenzyloxy)azetidine-1-carboxylate
Example 75: 3-(Trifluoromethyl)phenyl 3-(4-chlorobenzyloxy)azetidine-1-carboxylate
Example 76: 3-Bromophenyl 3-(4-chlorobenzyloxy)azetidine-1-carboxylate
Example 77: 3-Carbamoylphenyl 3-(4-chlorobenzyloxy) azetidine-1-carboxylate
Example 78: 3-Methoxyphenyl 3-(4-Bromobenzyloxy)azetidine-1-carboxylate
Example 79: 2,4-Dichlorophenyl 3-(4-chlorobenzyloxy) azetidine-1-carboxylate
Example 80: 3-(Pyridin-3-yl)phenyl 3-(4-chlorobenzyloxy) azetidine-1-carboxylate
Example 81 3-(4-Chlorobenzyloxy)-N-phenylazetidine-1-carboxamide
Example 82: 3-(4-Bromobenzyloxy)-N-(pyridin-3-yl)azetidine-1-carboxamide
Example 83 (1H-Benzo[d]imidazol-1-yl)(3-(4-phenylpiperidin-1-yl)azetidin-1-yl)methanone Example 84 (3-(4-Benzylpiperidine)azetidin-1-yl)(4-phenyl[1H] imizadol-1-yl)methanone
Example 85 (4-Phenyl-1H-imidazol-1-yl)(3-(4-phenylpiperidin-1-yl)azetidin-1-yl)methanone
Example 86 (3-(4-Bromobenzyloxy)azetidin-1-yl)(4-phenyl-1H-imidazol-1-yl)methanone
Example 87 (1H-Benzo[d]imidazol-1-yl)(3-(4-Bromobenzyloxy)azetidin-1-yl)methanone
Example 88 3-(4-Bromobenzyloxy)azetidin-1-yl](piperidin-1-yl)methanone
Example 89 (3-(4-Phenylpiperidin-1-yl)azetidin-1-yl)(1H-pyrazol-1-yl)methanone
Example 90 3-(4-Phenylpiperidin-1-yl)azetidin-1-yl)(1H-1,2,4-triazol-1-yl)methanone
Example 91 3-(4-Bromophenylthio)azetidin-1-yl)(1H-1,2,4-triazol-1-yl)methanone.

In a another embodiment, this invention relates to compounds of Formula III

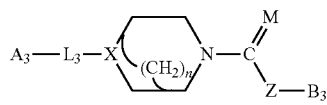

Wherein
X=CH, N;
M=O, S;
Z=O, NH, or none; when Z=none, B₃ directly attaches to C=M;
n=1-3
L₃ is selected from —(CH₂)ₙ,

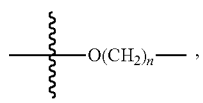

—C(=O)— when X is N, or from —(CH₂)ₙO—, —O—, —CH=CH—, —CONH—, —NH—, —NR₁ when X is CH, where n=0-3;

A₃ is selected from aryl, heteroaryl, fluoren-9-yl, and each aryl, heteroaryl or fluoren-9-yl group may be unsubstituted, or substituted with one or two moieties as defined below;
-halogen —NO₂, —CN, —OH, —NH₂, —CONH₂, —CO₂Me; -alkyl, —Oalkyl, -halogen, —CF₃, —OCF₃, —Salkyl, —OCH₂Ph, -Ph, —S(O)-alkyl, —SO₂-alkyl, —CO₂-alkyl, —COOH, —NHR₃, —NR₃R₄, —NR₃SO₂R₄, —NO₂, —CN, —CONR₃R₄; morpholino; thiomorpholino, 1,1-dioxothiomorpholine, oxothiomorpholino;
R2 and R₄ are independently selected from —H or -alkyl, cycloalkyl;
B₃ can be selected from aryl or heteroaryl groups, and each aryl or heteroaryl group may be unsubstituted or substituted with one or two moieties as defined below:
—H, -halogen, —CN, —OH, —NH₂, —CO₂Me, —CONH₂, —OMe;

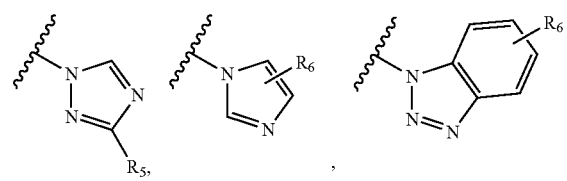

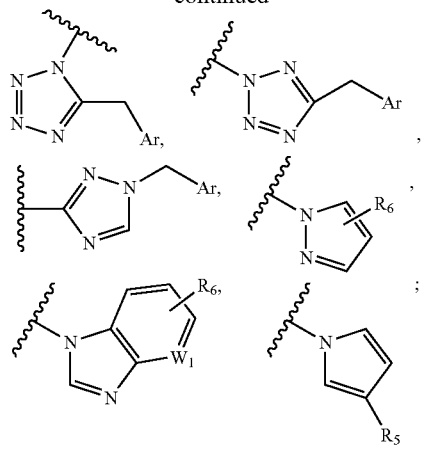

B₃ is also encompassing
Wherein W₁ is either CH or N;
Ar can be aryl or heteroaryl containing 1 to 3 heteroatoms;
R₅ is selected from —H, -halogen, —CN, —OH, —NH₂, —CO₂Me, —CONH₂, —OMe;
R₆ is selected from monocyclic heteroaryl ring containing 1 to 3 heteroatoms, and the heteroaryl ring can be substituted with one or two groups as defined below,
—CN, —OH, —OMe, —CF₃, —OCF₃, —OCH₂Ph, —CONH₂, —SO₂NH₂, —COOH, halogen or

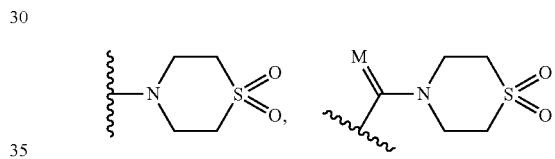

Wherein M can be selected from O or S,
Particularly useful compounds of Formula III include those compounds wherein L₃ is selected from —(CH₂)ₙ, or —C(=O)— when X is N, or L₃ is selected from —(CH₂)— O—, —O—, —CH=CH—, —CONH—, —NH—,

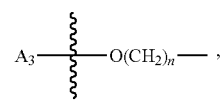

—NR₁ when X is CH, where n=0-2;
B₃ can be selected from aryl or heteroaryl groups, and each aryl or heteroaryl group may be unsubstituted or substituted with one or two moieties as defined below:
-halogen, —CN, —OH, —CO₂Me, —CONH₂;

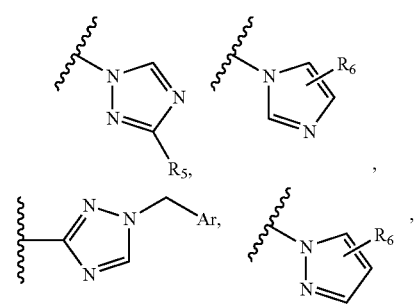

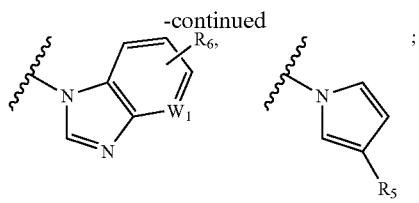

B₃ is also encompassing and the remaining substituents are as described above.

More particularly useful compounds of Formula III are those compounds wherein
X=N;
M=O;
Z=O, NH or none; when Z=none B₃ is directly attaches to C=M;
n=1
L₃ is selected from is selected from —(CH₂)ₙ where n is 0 or 1;
A₃ is selected from aryl, heteroaryl, fluorenyl, and each aryl, heteroaryl group may be unsubstituted, substituted with one or two moieties as defined below;
-halogen, —OCH₂Ph, -Ph;
B₃ can be selected from aryl or heteroaryl groups, and each aryl or heteroaryl group may be unsubstituted or substituted with moieties as defined below:
—CN, —CO₂Me, —CONH₂;
B₃ can be

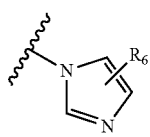

R₆ is selected from H, halogen, or Phenyl and the remaining substituents are as set forth above.

Examples of compounds of Formula III include:
Example 92: (1S,4S)—N-(3'-carbamoyl-[1,1'-biphenyl]-3-yl)-5-(quinolin-2-ylmethyl)-2,5-diazabicyclo[2.2.1]heptane-2-carboxamide
Example 93: (1S,4S)—N-(3'-cyano-[1,1'-biphenyl]-3-yl)-5-(quinolin-2-ylmethyl)-2,5-diazabicyclo[2.2.1]heptane-2-carboxamide
Example 94: (1S,4S)-5-([1,1'-biphenyl]-3-ylmethyl)-N-(3'-cyano-[1,1'-biphenyl]-3-yl)-2,5-diazabicyclo[2.2.1]heptane-2-carboxamide
Example 95: (1S,4S)—N-(3-bromophenyl)-5-(quinolin-2-ylmethyl)-2,5-diazabicyclo[2.2.1] heptane-2-carboxamide
Example 96: (4-phenyl-1H-imidazol-1-yl)((1S,4S)-5-(pyridin-2-yl)-2,5-diazabicyclo[2.2.1] heptan-2-yl)methanone
Example 97: ((1S,4S)-5-(3-fluorophenyl)-2,5-diazabicyclo[2.2.1]heptan-2-yl)(4-phenyl-1H-imidazol-1-yl)methanone
Example 98: ((1S,4S)-5-(3-(benzyloxy)phenyl)-2,5-diazabicyclo[2.2.1]heptan-2-yl)(4-phenyl-1H-imidazol-1-yl)methanone
Example 99: ((1S,4S)-5-([1,1'-biphenyl]-3-ylmethyl)-2,5-diazabicyclo[2.2.1]heptan-2-yl)(4-phenyl-1H-imidazol-1-yl)methanone
Example 100: ((1S,4S)-5-([1,1'-biphenyl]-3-ylmethyl)-2,5-diazabicyclo[2.2.1]heptan-2-yl)(4-bromo-1H-imidazol-1-yl)methanone
Example 101: phenyl (1 S,4S)-5-([1,1'-biphenyl]-3-ylmethyl)-2,5-diazabicyclo[2.2.1]heptane-2-carboxylate Definitions The compounds of this disclosure include any and all possible isomers, stereoisomers, enantiomers, diastereomers, tautomers, pharmaceutically-acceptable salts, and solvates thereof. Thus, the terms "compound" and "compounds" as used in this disclosure refer to the compounds of this disclosure and any and all possible isomers, stereoisomers, enantiomers, diastereomers, tantomers, pharmaceutically-acceptable salts, and solvates thereof. In general, the compositions of the disclosure can be alternately formulated to comprise, consist of, or consist essentially of, any appropriate components disclosed in this application. The compositions of the disclosure can additionally, or alternatively, be formulated so as to be devoid, or substantially free, of any components, materials, ingredients, adjuvants or species used in the prior art compositions or that are otherwise not necessary to the achievement of the function and/or objectives of the present disclosure. Reference to compounds of Formula I-III includes subsets thereof (e.g. Formula IA).

For convenience, certain terms employed in the specification, examples and claims are collected here. Unless defined otherwise, all technical and scientific terms used in this disclosure have the same meanings as commonly understood by one of ordinary skill in the art to which this disclosure belongs. The initial definition provided for a group or term provided in this disclosure applies to that group or term throughout the present disclosure individually or as part of another group, unless otherwise indicated.

The articles "a" and "an" are used in this disclosure to refer to one or more than one (i.e., to at least one) of the grammatical object of the article. By way of example, "an element" means one element or more than one element.

The term "or" is used in this disclosure to mean, and is used interchangeably with, the term "and/or," unless indicated otherwise.

The term "about" is used in this disclosure to mean a value − or +20% of a given numerical value. Thus, "about 60%" means a value between 60-20% of 60 and 60+20% of 60 (i.e., between 48% and 72%).

Unless otherwise specifically defined, "alcohol" refers to the general formula alkyl-OH and includes primary, secondary and tertiary variations.

Unless otherwise specifically defined, the term "alkyl" refers to optionally substituted or substituted straight or branched chain hydrocarbon radical containing from 1 to 10 carbon atoms. Examples of such groups include, but are not limited to methyl, ethyl, n-propyl, i-propyl, n-butyl, sec-butyl, tert-butyl etc.

Unless otherwise specifically defined, the ter "cycloalkyl" refers to a fully saturated cyclic hydrocarbon group containing from 3-10 carbon atoms in a cycloalkyl ring.

Examples of such groups include, but are not limited to cyclopropyl, cyclobutyl, cyclopentyl, cyclohexyl, cycloheptyl, adamantyl, etc. Unless otherwise specifically defined, the term "adamantyl" includes, but is not limited to, 1-adamantyl, 2-adamantyl, and 3-adamantyl, etc.

Unless otherwise specifically defined, the term "alkenyl" refers to a straight or branched chain hydrocarbon radical containing from 2 to 15 carbon atoms and at least one carbon-carbon double bond. Exemplary such groups include, but are not limited to, ethenyl (also called "vinyl"), allyl, propenyl, crotyl, 2-isopentenyl, allenyl, butenyl, butadienyl, pentenyl, pentadienyl, 3(1,4-pentadienyl), hexenyl and hexadienyl. The alkenyl group may be optionally substituted with one or more substituents, e.g., 1 to 5 substituents, at any available point of attachment. Exemplary substituents include, but are not limited to, alkyl or substituted alkyl, as well as those groups recited above as exemplary alkyl substituents. The exemplary substituents can themselves be optionally substituted.

Unless otherwise specifically defined, the term "alkynyl" refers to a straight or branched chain hydrocarbon radical containing from 2 to 15 carbon atoms and at least one carbon-carbon triple bond. Exemplary such groups include, but are not limited to, ethynyl, propynyl and butynyl. The alkynyl group may be optionally substituted with one or more substituents, e.g., 1 to 5 substituents, at any available point of attachment. Exemplary substituents include, but are not limited to, alkyl or substituted alkyl, as well as those groups recited above as exemplary alkyl substituents. The exemplary substituents can themselves be optionally substituted.

Unless otherwise specifically defined, "aryl" refers to aryl groups (or rings) that contain only carbon atoms. Aryl group (or aryl ring) include phenyl, naphthyl, anthracene, phenathrene etc.

Unless otherwise specifically defined, "heteroaryl" refers to aryl groups (or rings) that contain one or more heteroatoms selected from oxygen, nitrogen and/or sulfur as ring atoms. Heteroaryl groups (or rings) also include fused polycyclic systems in which one or more monocyclic aryl or monocyclic heteroaryl group is fused to another heteroaryl group, "Heteroaryl" can include "divalent radicals", the term "divalent heteroaryl radicals" unless otherwise specifically defined refers to the general formula: -heteroaryl-. Examples of heteroaryl groups include but are not limited to, furanyl, thienyl, pyrrolyl, oxazolyl, thiazolyl, isoxazolyl, pyrazolyl, imidazolyl, oxadiazolyl, pyridinyl, pyrimidinyl, purinyl, benzoxazolyl, benzothiazolyl, benzimidazolyl, benzofuranyl, indolyl, quinolinyl, quinoxalinyl.

Unless otherwise specifically defined, "halogen" refers to an atom selected from fluorine, chlorine, bromine and iodine.

The phrase "pharmaceutically acceptable" is employed in this disclosure to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "salt(s)", as employed in this disclosure, denotes acidic and/or basic salts formed with inorganic and/or organic acids and bases.

The term "treating" with regard to a subject, refers to improving at least one symptom of the subject's disorder. Treating can be curing, improving, or at least partially ameliorating the disorder.

The term "disorder" is used in this disclosure to mean, and is used interchangeably with, the terms disease, condition, or illness, unless otherwise indicated.

The terms "effective amount" and "therapeutically effective amount" as used in this disclosure refer to an amount of a compound that, when administered to a subject, is capable of reducing a symptom of a disorder in a subject. The actual amount which comprises the "effective amount" or "therapeutically effective amount" will vary depending on a number of conditions including, but not limited to, the particular disorder being treated, the severity of the disorder, the size and health of the patient, and the route of administration. A skilled medical practitioner can readily determine the appropriate amount using methods known in the medical arts.

As used in this disclosure, the term "subject" includes, without limitation, a human or an animal Exemplary animals include, but are not limited to, mammals such as mouse, rat, guinea pig, dog, cat, horse, cow, pig, monkey, chimpanzee, baboon, or rhesus monkey.

The term "administer", "administering", or "administration" as used in this disclosure refers to either directly administering a compound or pharmaceutically acceptable salt of the compound or a composition to a subject, or administering a pro-drug derivative or analog of the compound or pharmaceutically acceptable salt of the compound or composition to the subject, which can form an equivalent amount of active compound within the subject's body. The compounds of the present invention may be converted to salts in particular pharmaceutically acceptable salts using art recognized procedures.

Compounds of the invention may be prepared employing conventional methods that utilize readily available reagents and starting materials. The inhibitory compounds need not be made exclusively from the illustrative syntheses. A person of skill in the art understands that additional methods of making the inhibitory compounds exist. A person of skill in the art also understands that general synthetic schemes for the compounds disclosed herein can be understood from the illustrative schemes below.

Methods of Inhibition and Modulation

This disclosure is also directed to a method of assessing the modulating effect on cannabinoid receptors in a biological sample by using the compounds of Formulas I-III and their pharmaceutically acceptable salts thereof. The method comprises (a) measuring the level of a cannabinergic ligand in the biological sample, (b) contacting the sample with a compound of Formula I, II, or III, thereby inhibiting an enzyme that hydrolyzes the cannabinergic ligand, and (c) measuring the level of the cannabinergic ligand in the contacted sample, the cannabinoid receptors being modulated if the level of the cannabinergic ligand in the contacted sample is the same or greater than the level of the cannabinergic ligand in the uncontacted sample.

In some instances, the enzyme inhibited is FAAH and in other examples MAGL is inactivated. In further examples testing of some compounds of Formulas shows inhibition of FAAH/MAGL in both in vitro and in vivo systems. Inhibition of FAAH, MAGL, or dual FAAH/MAGL has the effect of preventing the degradation of endocannabinoid ligands and increasing or maintaining the level of endocannabinoid ligands in a system. Thus, the disclosed compounds, when administered in a therapeutically effective amount, increase or maintain the in vivo concentration of endogenous cannabinergic ligands in a subject, thereby enhancing or maintaining activation of cannabinoid receptors. In other instances, the inhibitor also inhibits FAAH in addition to MAGL. The joint inactivation of both enzymes leads to enhanced therapeutic benefits because cannabinoid receptors can be modulated by additional cannabinergic ligands.

Methods of Treating Disorders Using FAAH and or MAGL Inhibitory Compounds

Some of the physiological effects provided by modulation of the cannabinoid receptors by cannabinergic ligands are useful to treat a disorder in a subject. Such treatable physiological effects include, but are not limited to, neuroprotection; reduction of inflammation; reduction of pain; reduction of central pain; reduction of peripheral pain; modulation of memory; sleep inducement; modulation of the immune system; hypotension; reduction of emesis; effects on gastrointestinal motility; effects on motor function; effects on intestinal transit and colonic propulsion; modulation of appetite; and modulation of fertility. Inhibition of FAAH and or MAGL activity increases or maintains the concentration of existing levels of endogenous cannabinergic ligands and thereby increases or maintains the magnitude and duration of the physiological effect provided by those cannabinergic ligands. Therefore, the disclosed compounds, and therapeutic formulations containing such compounds, enhance or maintain the magnitude and duration of the physiological effects produced by a cannabinergic ligand in a subject when administered in therapeutically effective amounts.

Disorders that can be treated by inhibition of MAGL and/or MAGL and FAAH and indirect stimulation of the cannabinoid receptors include, for example: appetite disorders, metabolic disorders, movement disorders, inflammation, pain, neuropathic pain (e.g., neuropathic low back pain, complex regional pain syndrome, post trigeminal neuralgia, causalgia, toxic neuropathy, reflex sympathetic dystrophy, diabetic neuropathy, chronic neuropathy caused by chemotherapeutic agents), central pain, peripheral pain, neuropathy (e.g., diabetic neuropathy, pellagric neuropathy, alcoholic neuropathy, Beriberi neuropathy, burning feet syndrome), neurodegenerative diseases including multiple sclerosis, Parkinson's disease, Huntington's chorea, Alzheimer's disease, amyotrophic lateral sclerosis; memory disorders, mood disorders, sleep disorders, gastrointestinal motility disorders such as irritable bowel syndrome and diarrhea; cardiovascular disease, hypertension, osteoporosis, osteoarthritis, emesis, epilepsy, mental disorders such as schizophrenia and depression; glaucoma, cachexia, insomnia, traumatic brain injury, spinal cord injury, seizures, excitotoxin exposure, ischemia, AIDS wasting syndrome, psychological disorders including anxiety disorders (e.g., panic disorder, acute stress disorder, post-traumatic stress disorder, substance-induced anxiety disorders, obsessive-compulsive disorder, agoraphobia, specific phobia, social phobia), to modulate the immune system; to regulate fertility; to prevent or reduce diseases associated with motor function such as Tourette's syndrome; to provide neuroprotection, to produce peripheral vasodilation; to slow down intestinal transit and colonic propulsion; to treat several types of cancer, as well as other ailments in which a growing family of bioactive lipid mediators is implicated.

The disclosed inhibitory compounds and pharmaceutical formulations can also be used in combination with one or more agents treating and/or targeting the disorder or the endogenous cannabinergic system. Such agents include, but are not limited to, CB1 cannabinoid receptor agonists, CB2 cannabinoid receptor agonists, analgesics, FAAH inhibitors, anadamide transport inhibitors, COX-2 enzyme inhibitors, anxiolytics, antidepressants, and opioids. For example, these compounds and pharmaceutical formulations can be used in conjunction with other cannabinergic ligands that act directly on the CB1 and CB2 receptors.

In certain instances, the cannabinergic ligand is 2-arachidonoylglycerol. The disclosed compounds have high potential to be used as research tools to probe MAGL and related lipase mechanisms of catalysis, and to uncover the biological roles of lipid mediators such as 2-arachidonoylglycerol. For example, the disclosed compounds can be used as in vivo imaging agents; to maintain the level of 2-arachidonoylglycerol in vitro to study the effect of 2-arachidonoylglycerol in cells and to enhance the levels of 2-arachidonoylglycerol in vivo in order to study the effect of 2-arachidonoylglycerol on humans and animals. The disclosed compounds can be used to characterize cells, for example, to determine if a cell type has cannabimimetic or lipase activity. For example, the disclosed compounds can be used to determine if a cell population expresses MAGL by contacting the cells with a disclosed compound and then determining if there is an increase in the concentration of 2-arachidonoylglycerol. The inhibitors disclosed in this application can also be used as an aid in drug design, for example as a control in assays for testing other compounds for their ability to inhibit MAGL and to determine the structure activity requirements of MAGL inhibitors.

The disclosed compounds can also be used to prepare prodrugs. Prodrugs are known to those skilled in the art of pharmaceutical chemistry, and provide benefits such as increased adsorption and half-life. Those skilled in the art of drug delivery will readily appreciate that the pharmacokinetic properties of Formula (I) can be controlled by an appropriate choice of moieties to produce prodrug derivatives.

Formulation

This disclosure is also directed to a pharmaceutical formulation comprising at least one compound of Formula I, II or III, and a pharmaceutically-acceptable carrier. Such formulations are suitable for administration to a subject. The pharmaceutical formulation can be used for treating a disorder described above.

Any suitable pharmaceutically acceptable carrier known in the art can be used as long as it does not affect the inhibitory activity of a compound of Formula I, II or ill. Carriers may be used that efficiently solubilize the agents. Carriers include, but are not limited to, a solid, liquid, or a mixture of a solid and a liquid. The carriers can take the form of capsules, tablets, pills, powders, lozenges, suspensions, emulsions, or syrups. The carriers can include substances that act as flavoring agents, lubricants, solubilizers, suspending agents, binders, stabilizers, tablet disintegrating agents, and encapsulating materials. Other examples of suitable physiologically acceptable carriers are described in *Remington's Pharmaceutical Sciences* (21st ed. 2005), incorporated into this disclosure by reference.

Non-limiting examples of materials which can serve as pharmaceutically-acceptable carriers include: (1) sugars, such as lactose, glucose, and sucrose; (2) starches, such as corn starch and potato starch; (3) cellulose and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline, (18) Ringer's solution, (19) ethyl alcohol; (20) phosphate buffer solutions; and (21) other non-toxic compatible substances employed in pharmaceutical formulations.

The formulations can conveniently be presented in unit dosage form and can be prepared by any methods known in the art of pharmacy. The amount of compound of Formula (I) which can be combined with a carrier material to produce a single-dosage form will vary depending upon the subject being treated, the particular mode of administration, the particular condition being treated, among others. The amount of active ingredient that can be combined with a carrier material to produce a single-dosage form will generally be that amount of the compound that produces a therapeutic effect. Generally, out of one hundred percent, this amount will range from about 1 percent to about ninety-nine percent of active ingredient, in some instances from about 5 percent to about 70 percent, in other instances from about 10 percent to about 30 percent.

Methods of preparing these formulations or compositions include the step of bringing into association a compound disclosed in this application with a carrier and, optionally, one or more accessory ingredients. In general, the formulations are prepared by uniformly and intimately bringing into association a compound of Formula (I-III) with liquid carriers, or timely divided solid carriers, or both, and then, if necessary, shaping the product.

In solid dosage forms of the disclosed compounds for oral administration (e.g., capsules, tablets, pills, dragees, powders, granules, and the like), the active ingredient is mixed with one or more additional ingredients, such as sodium citrate or dicalcium phosphate, and/or any of the following: (1) fillers or extenders, such as, but not limited to, starches, lactose, sucrose, glucose, mannitol, and/or silicic acid; (2) binders, such as, but not limited to, carboxymethylcellulose, alginates, gelatin, polyvinyl pyrrolidone, sucrose, and/or acacia; (3) humectants, such as, but not limited to, glycerol; (4) disintegrating agents, such as, but not limited to, agar, calcium carbonate, potato or tapioca starch, alginic acid, certain silicates, and sodium carbonate; (5) solution retarding agents, such as, but not limited to, paraffin; (6) absorption accelerators, such as, but not limited to, quaternary ammonium compounds; (7) wetting agents, such as, but not limited to, cetyl alcohol and glycerol monostearate; (8) absorbents, such as, but not limited to, kaolin and bentonite clay; (9) lubricants, such as, but not limited to, talc, calcium stearate, magnesium stearate, solid polyethylene glycols, sodium lauryl sulfate, and mixtures thereof; and (10) coloring agents. In the case of capsules, tablets, and pills, the pharmaceutical compositions can also comprise buffering agents. Solid compositions of a similar type can also be employed as fillers in soft and hard-filled gelatin capsules using such excipients as lactose or milk sugars, as well as high molecular weight polyethylene glycols, and the like.

In powders, the carrier is a finely-divided solid, which is mixed with an effective amount of a finely-divided agent. Powders and sprays can contain, in addition to a compound of Formula (I-III), excipients, such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Tablets for systemic oral administration can include one or more excipients as known in the art, such as, for example, calcium carbonate, sodium carbonate, sugars (e.g., lactose, sucrose, mannitol, sorbitol), celluloses (e.g., methyl cellulose, sodium carboxymethyl cellulose), gums (e.g., arabic, tragacanth), together with one or more disintegrating agents (e.g., maize, starch, or alginic acid, binding agents, such as, for example, gelatin, collagen, or acacia), lubricating agents (e.g., magnesium stearate, stearic acid, or talc), inert diluents, preservatives, disintegrants (e.g., sodium starch glycolate), surface-active and/or dispersing agent, A tablet can be made by compression or molding, optionally with one or more accessory ingredients.

In solutions, suspensions, emulsions or syrups, an effective amount of a disclosed compound is dissolved or suspended in a carrier, such as sterile water or an organic solvent, such as aqueous propylene glycol. Other compositions can be made by dispersing the agent in an aqueous starch or sodium carboxymethyl cellulose solution or suitable oil known to the art. The liquid dosage forms can contain inert diluents commonly used in the art, such as, for example, water or other solvents, solubilizing agents and emulsifiers, such as, but not limited to, ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols, and fatty acid esters of sorbitan, and mixtures thereof.

Besides inert diluents, the oral compositions can also include adjuvants, such as wetting agents, emulsifying and suspending agents, sweetening, flavoring, coloring, perfuming, and preservative agents. Suspensions can contain, in addition to the active compound, suspending agents as, for example, ethoxylated isostearyl alcohols, polyoxyethylene sorbitol and sorbitan esters, microcrystalline cellulose, aluminum metahydroxide, bentonite, agar and tragacanth, and mixtures thereof.

Formulations of the pharmaceutical compositions for rectal or vaginal administration can be presented as a suppository, which can be prepared by mixing one or more compounds of this disclosure with one or more suitable non-irritating excipients or carriers comprising, for example, cocoa butter, polyethylene glycol, a suppository wax or a salicylate, and which is solid at RT but liquid at body temperature and, thus, will melt in the rectum or vaginal cavity and release the agents. Formulations suitable for vaginal administration also include, hut are not limited to, pessaries, tampons, creams, gels, pastes, foams, or spray formulations containing such carriers as are known in the art to be appropriate.

Dosage forms for the topical or transdermal administration of a compound of this disclosure include, but are not limited to, powders, sprays, ointments, pastes, creams, lotions, gels, solutions, patches, and inhalants. The active compound can be mixed under sterile conditions with a pharmaceutically-acceptable carrier, and with any preservatives, buffers, or propellants.

Ointments, pastes, creams, and gels can contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Transdermal patches have the added advantage of providing controlled delivery of a compound of Formula (I) to the body. Such dosage forms can be made by dissolving or dispersing the agents in the proper medium. Absorption enhancers can also be used to increase the flux of the agents across the skin. The rate of such flux can be controlled by either providing a rate controlling membrane or dispersing the compound in a polymer matrix or gel.

The compounds of Formulas I-III are administered in a therapeutically effective amount to a patient in need of such treatment. Such an amount is effective in treating a disorder of the patient. This amount can vary, depending on the activity of the agent utilized, the nature of the disorder, and the health of the patient. A skilled practitioner will appreciate that the therapeutically-effective amount of a compound of Formula I, II or III can be lowered or increased by fine-tuning and/or by administering more than one compound of Formulas or by administering a compound of Formula I, II or III together with a second agent (e.g., antibiotics, antifungals, antivirals, NSAIDS, DMARDS, steroids, etc.). Therapeutically-effective amounts can be easily determined, for example, empirically by starting at relatively low amounts and by step-wise increments with concurrent evaluation of beneficial effect (e.g., reduction in symptoms).

The actual effective amount will be established by dose/response assays using methods standard in the art (Johnson et al., *Diabetes.*, (1993) 42:1179). As is known to those in the art, the effective amount will depend ort bioavailability, bioactivity, and biodegradability of the compound of Formula I, II or III.

A therapeutically-effective amount is an amount that is capable of reducing a symptom of a disorder in a subject. Accordingly, the amount will vary with the subject being treated. Administration of the compound of Formula I, II or III can be hourly, daily, weekly, monthly, yearly, or a single event. For example, the effective amount of the compound can comprise from about 1 μg/kg body weight to about 100 mg/kg body weight. In one embodiment, the effective amount of the compound comprises from about 1 μg/kg body weight to about 50 mg/kg body weight. In a further embodiment, the effective amount of the compound comprises from about 10 μg/kg body weight to about 10 mg/kg body weight. When one or more compounds of Formulas I-III or agents are combined with a carrier, they can be present in an amount of about 1 weight percent to about 99 weight percent, the remainder being composed of the pharmaceutically-acceptable carrier.

Administration

Methods of administration of the therapeutic formulations comprising the compounds of Formulas I-III can be by any of a number of methods known in the art. These methods include, but are not limited to, local or systemic administration. Exemplary routes of administration include, but are not limited to, oral, parenteral, transdermal, intradermal, intramuscular, intraperitoneal, intravenous, subcutaneous, intranasal (e.g., nebulizer, inhaler, aerosol dispenser), colorectal, rectal, intravaginal, and any combinations thereof. In addition, it may be desirable to introduce pharmaceutical compositions of the disclosed compounds into the central nervous system by any suitable route, including intraventricular and intrathecal injection. Intraventricular injection can be facilitated by an intraventricular catheter, for example, attached to a reservoir, such as an Ommaya reservoir. Methods of introduction can be provided by rechargeable or biodegradable devices, e.g., depots. Furthermore, administration can occur by coating a device, implant, stent, or prosthetic. The compounds of Formulas I-III can also be used to coat catheters in any situation where catheters are inserted in the body.

The therapeutic formulations containing a compound of Formula I, II or III can also be administered as part of a combinatorial therapy with other agents. Combination therapy refers to any form of administration combining two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either simultaneously or sequentially. Thus, an individual who receives such treatment can have a combined (conjoint) effect of different therapeutic compounds.

In other instances, for example, in the case of inflammatory conditions, a therapeutic formulation containing a compound of Formula I, II or III can be administered in combination with one or more other agents useful in the treatment of inflammatory diseases or conditions. Agents useful in the treatment of inflammatory diseases or conditions include, but are not limited to, anti-inflammatory agents, or antiphlogistics. Exemplary antiphlogistics include, but are not limited to, glucocorticoids, such as cortisone, hydrocortisone, prednisone, prednisolone, fluorcortolone, triamcinolone, methylprednisolone, prednylidene, paramethasone, dexamethasone, betamethasone, beclomethasone, fluprednylidene, desoxymethasone, fluocinolone, flunethasone, diflucortolone, clocortolone, clobetasol and fluocortin butyl ester; immunosuppressive agents such as anti-TNF agents (e.g., etanercept, infliximab) and IL-1 inhibitors; penicillamine; non-steroidal anti-inflammatory drugs (NSAIDs) which encompass anti-inflammatory, analgesic, and antipyretic drugs such as salicyclic acid, celecoxib, difunisal and from substituted phenylacetic acid salts or 2-phenylpropionic acid salts, such as alclofenac, ibutenac, ibuprofen, clindanac, fenclorac, ketoprofen, fenoprofen, indoprofen, fenclofenac, diclofenac, flurbiprofen, piprofen, naproxen, benoxaprofen, carprofen and ciclopropfen; oxican derivatives, such as piroxican; anthranilic acid derivatives, such as mefenamic acid, flufenamic acid, tolfenamic acid and meclofenamic acid, anilino-substituted nicotinic acid derivatives, such as the fenamates miflumic acid, clonixin and flunixin; heteroarylacetic acids wherein heteroaryl is a 2-indol-3-yl or pyrrol-2-yl group, such as indomethacin, oxmetacin, intrazol, acemetazin, cinmetacin, zomepirac, tolmetin, colpirac and tiaprofenic acid; idenylacetic acid of the sulindac type; analgesically active heteroaryloxyacetic acids, such as benzadac; phenylbutazone; etodolac; nabunetone; and disease modifying antirheumatic drugs (DMARDs) such as methotrexate, gold salts, hydroxychloroquine, sulfasalazine, ciclosporin, azathioprine, and leflunomide. Other therapeutics useful in the treatment of inflammatory diseases or conditions include antioxidants. Antioxidants can be natural or synthetic. Antioxidants are, for example, superoxide dismutase (SOD), 21-aminosteroids/aminochromans, vitamin C or E, etc. Many other antioxidants are known to those of skill in the art. The compounds of Formula (I) can serve as part of a treatment regimen for an inflammatory condition, which may combine many different anti-inflammatory agents. For example, the subject compounds can be administered in combination with one or more of an NSAID, DMARD), or immunosuppressant. The subject compounds can also be administered in combination with methotrexate. The subject antibodies can also be administered in combination with a TNF-α inhibitor.

In the case of cardiovascular disease conditions, and particularly those arising from atherosclerotic plaques, which are thought to have a substantial inflammatory component, the therapeutic formulation including a compound of Formula (I) can be administered in combination with one or more other agents useful in the treatment of cardiovascular diseases. Agents useful in the treatment of cardiovascular diseases include, but are not limited to, β-blockers such as carvedilol, metoprolol, bucindolol, bisoprolol, atenolol, propranolol, nadolol, timolol, pindolol, and labetalol; antiplatelet agents such as aspirin and ticlopidine; inhibitors of angiotensin-converting enzyme (ACE) such as captopril, enalapril, lisinopril, benazopril, fosinopril, quinapril, ramipril, spirapril, and moexipril; and lipid-lowering agents such as mevastatin, lovastatin, simvastatin, pravastatin, fluvastatin, atorvastatin, and rosuvastatin.

In the case of cancer, the subject compounds can be administered in combination with one or more anti-angiogenic factors, chemotherapeutics, or as an adjuvant to radiotherapy. It is further envisioned that the administration of the subject compounds will serve as part of a cancer treatment regimen, which may combine many different cancer therapeutic agents.

The disclosure is further illustrated by the following examples, which are not to be construed as limiting this disclosure in scope or spirit to the specific procedures described in this disclosure. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the sprint of the present disclosure and/or scope of the appended claims.

FAAH Inhibitory Compounds

Certain chemical compounds have been found to inhibit the inactivation of endocannabinoids by FAAH. These compounds may not bind to, or may have lesser affinity for, the CB1 and/or CB2 cannabinoid receptors. Thus, the physiological action for such compounds and may not be the direct modulation of the CB1 and/or CB2 receptors. Inhibition of FAAH in a subject slows the normal degradation and inactivation of AEA and other fatty acid amides. This inhibition allows maintained or higher levels of those endogenous ligands to remain present in the subject. The maintained or higher levels of those ligands provide increased stimulation of the cannabinoid CB1 and CB2 receptors. The inhibition of FAAH also enhances the effects of exogenous cannabinergic ligands and allows them to stimulate cannabinoid receptors at lower concentrations as compared to systems in which FAAH action is not inhibited.

MAGL Inhibitory Compounds

Certain chemical compounds have been found to inhibit the inactivation of endocannabinoids by MAGL. These compounds may not bind to, or may have lesser affinity for, the CB1 and/or CB2 cannabinoid receptors. Thus, the physiological action for such compounds and may not be the direct modulation of the CB1 and/or CB2 receptors. Inhibition of MAGL in a subject slows the normal degradation and inactivation of 2-AG and other 2-monoacylglycerols (2-MAGs). This inhibition allows maintained or higher levels of those endogenous ligands to remain present in the subject. The maintained or higher levels of those ligands provide increased stimulation of the cannabinoid CB1 and CB2 receptors.

Dual FAAH/MAGL Inhibitory Compounds

Certain chemical compounds have been found to inhibit the inactivation of endocannabinoids by FAAH/MAGL. These compounds may not bind to, or may have lesser affinity for, the CB1 and/or CB2 cannabinoid receptors. Thus, the physiological action for such compounds and may not be the direct modulation of the CB1 and/or CB2 receptors. Inhibition of FAAH/MAGL in a subject slows the normal degradation and inactivation of anandamide and other fatty acid ethanolamines as well as 2-AG and other 2-monoacylglycerols (2-MAGs). This inhibition allows maintained or higher levels of those endogenous ligands to remain present in the subject. The maintained or higher levels of those ligands provide increased stimulation of the cannabinoid CB1 and CB2 receptors.

Example processes for synthesis of compounds of Formula I-III are provided below in Methods A-M:

The inhibitory compounds of Formula I-III can be synthesized by chemical means as described in methods A-M below. Novel compounds may be synthesized from commercially available starting material. The inhibitory compounds need not be made exclusively from the illustrative syntheses. A person of skill in the art understands that additional methods of making the inhibitory compounds exist. A person of skill in the art also understands that general synthetic schemes for the compounds disclosed herein can be understood from the illustrative schemes below Method A: Synthesis of N-Aryl urea derivatives 7

Referring to Scheme 1, N-Aryl urea derivatives 7 were synthesized by reaction of piperazine derivatives 3 with substituted biaryl phenyl carbamates 6, under microwave irradiation. Piperazine derivatives 3 were obtained by deprotection of N—BOC group 2 under acidic condition. Aryl piperazine derivatives 2 (n=0) were obtained by Buchwald coupling (Xie et al, *J. Org. Chem.*, (2006) 71: 6522-6529) of aryl bromides or iodides with substituted N—BOC piperazines 1. Aryl piperazine derivatives 2 (n=1) were produced by nucleophilic displacement of benzyl chlorides or benzyl bromides with commercially available substituted N—BOC piperazines 1 The common intermediate biaryl phenyl carbamates 6 were synthesized by Suzuki coupling (Bermejo et al, *J. Am. Chem. Soc.*, (2008) 130: 15798-15799) of aryl boronic acids 4 with m-bromoaniline to give biaryl amine derivatives 5, which were further treated with phenyl chloroformate to give phenyl carbamates 6, as shown in scheme I.

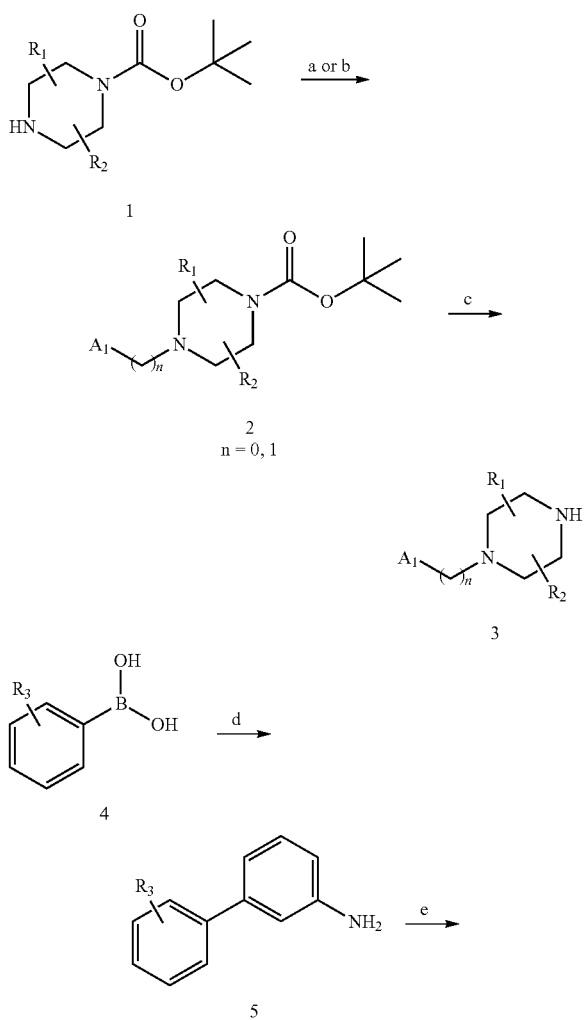

-continued

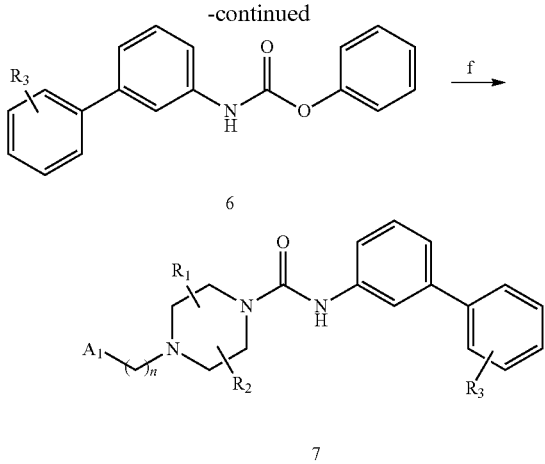

Reagents: (a) Ar—Br, Pd₂(dba)₃, BINAP, NaOtBu, DME, 80° C.; (b) ArCH₂Br, Et₃N, CH₃CN microwave, 100° C., 15 min.; (c) TFA/CH₂Cl₂, rt; (d) 3-Bromoaniline, Ba(OH)₂ x8H₂O, Pd(PPh₃)₄ DME/H₂O, microwave, 120° C.; (e) Phenyl chloroformate, Et₃N, CH₂Cl₂, rt.; (f) 3, CH₃CN, microwave, 110° C., 10 min.

The Following Examples were Prepared by Following Method A

Synthesis of Example 1

(S)—N-(3'-carbamoyl-[1,1'-biphenyl]-3-yl)-3-methyl-4-(quinolin-2-ylmethyl) piperazine-1-carboxamide (7; A₁=quinoline, n=1, R₁=3-Me, R₂=H, R₃=CONH₂)

Step a) Synthesis of tert-butyl (S)-3-methyl-4-(quinolin-2-ylmethyl)piperazine-1-carboxylate A solution of 2-(chloromethyl)quinoline hydrobromide (2.0 g, 7.74 mmol) in acetonitrile (20 mL) was added tert-butyl (S)-2-methylpiperazine-1-carboxylate 1, (1.86 g, 9.28 mmol) and triethylamine (1.61 mL, 11.61 mmol) and the resulting mixture was heated in a sealed tube under microwave irradiation at 100° C. for 15 min with stirring. The reaction mixture was cooled to room temperature. The solvent was removed in vacuo and the residue partitioned between dichloromethane and water. The aqueous layer was further extracted with dichloromethane and the combined organic extracts were washed with brine, and dried over MgSO₄. The solvent was removed in vacuo to give a crude product, which was purified by flash column chromatography to give 2.25 g of tert-butyl (S)-3-methyl-4-(quinolin-2-ylmethyl)piperazine-1-carboxylate.
¹H NMR (500 M Hz, CDCl₃) δ 8.13 (d, 1H, J=9 Hz); 8.06 (d, 1H, J=9.0 Hz); 7.81 (d, 1H, J=8.0 Hz); 7-71-7.66 (m, 2H); 7.51 (t, 1H, J=8.0 Hz); 8.13 (bd, 1H, J=9.0 Hz) 8.06 (bd, 1H, J=9.0 Hz); 4.25 (d, 1H, J=14 Hz); 3.84-3.65 (m, 3H); 3.15 (bs, 1H); 2.93 (bs, 1H); 2.70 (bs, 1H); 2.58 (bs, 1H); 0.96 (bs, 9H)

Step c) Synthesis of (S)-2-((2-methylpiperazin-1-yl)methyl)quinolone

To a solution of tert-butyl (S)-3-methyl-4-(quinolin-2-ylmethyl)piperazine-1-carboxylate 2 (2.0 g, 5.86 mmol) in methylene chloride (25 mL) was added trifluoroacetic acid (2.25 mL, 29.3 mmol). After stirring at room temperature for 16 h, the mixture was concentrated in vacuo, and diluted with ethyl acetate and aqueous sodium bicarbonate. The organic layer was washed with brine, dried over MgSO₄ and concentrated, to give product (S)-2-((2-methylpiperazin-1-yl)methyl)quinolone (1.27 g) which was further used at the next step without any purification.
¹H NMR (500 M Hz, CDCl₃) δ 8.13 (d, 1H, J=9 Hz); 8.06 (d, 1H, J=9.0 Hz); 7.81 (d, 1H, J=8.0 Hz); 7-71-7.66 (m, 2H); 7.51 (t, 1H, J=8.0 Hz); 8.13 (bd, 1H, J=9.0 Hz) 8.06 (bd, 1H, J=9.0 Hz); 4.25 (d, 1H, J=14 Hz); 3.84-3.65 (m, 3H); 3.15 (bs, 1H); 2.93 (bs, 1H); 2.70 (bs, 1H); 2.58 (bs, 1H Step d) Synthesis of 3'-amino-[1,1'-biphenyl]-3-carboxamide A mixture of 3-bromo aniline (1.0 g, 5.81 mmol), (3-carbamoylphenyl)boronic acid (1.25 g, 7.56 mmol) (4), Ba(OH)₂ (2.75 g, 8.72 mmol), and Pd(PPh₃)₄ (80 mg) in DME (3 mL)/water (2 mL) was flushed with argon, and heated in a sealed tube under microwave irradiation at 120° C. for 15 min with stirring. The reaction mixture was cooled to room temperature, diluted with EtOAc (20 mL) and aqueous NH₄Cl solution. the catalyst was removed by filtration through a celite pad. The organic layer was washed with water, brine, and dried over MgSO₄, and concentrated under vacuo. Purification by flash column chromatography gave 0.96 g of 3'-amino-[1,1'-biphenyl]-3-carboxamide, as white solid.
¹H NMR (500 M Hz, CDCl₃) δ 8.04 (d, 2H, J=7.5 Hz); 7.63-7.47 (m, 3H); 7.32 (d, 1H, J=6.0 Hz); 3.93 (s, 2H); 2.65 (t, 4H, J=5.5 Hz); 2.34 (t, 4H, J=5.5 Hz)

Step e) Synthesis of phenyl (3'-carbamoyl-[1,1'-biphenyl]-3-yl)carbamate

To a solution of 3'-amino-[1,1'-biphenyl]-3-carboxamide (2.0 g, 9.42 mmol) in dry THF (30 mL) at 0° C., was added phenyl chloroformate (1.63 g, 10.4 mmol) drop wise over 15 min period. The reaction mixture was allowed to warm to room temperature. After 12 h, the mixture was diluted with EtOAc (100 mL) and washed with aqueous NaHCO₃ solution (20 mL). The organic layer was dried over MgSO₄ and concentrated. The residue was chromatographed to give 2.72 g of phenyl (3'-carbamoyl-[1,1'-biphenyl]-3-yl)carbamates as a white solid.
¹H NMR (500 M Hz, CDCl₃) δ 9.29 (bs, 1H); 8.22 (s, 1H); 7.98 (s, 1H); 7.98 (d, 1H, J=8 Hz); 7.82 (d, 1H, J=8 Hz); 7.66 (d, 1H, J=8 Hz); 7.56 (t, 2H, J=8 Hz); 7.49-7.41 (m, 3H); 7.27-7.23 (m, 2H)

Step f) Synthesis of (S)—N-(3'-carbamoyl-[1,1'-biphenyl]-3-yl)-3-methyl-4-(quinolin-2-ylmethyl) piperazine-1-carboxamide ((7; A₁=quinoline, n=1, R₁=3-Me, R₂=H, R₃=CONH₂)

A solution of (S)-2-((2-methylpiperazin-1-yl)methyl)quinolone (0.6 g, 2.64 mmol) and biphenyl-3-yl-carbamic acid phenyl ester 6 (0.92 g, 2.77 mmol) in acetonitrile (10 mL) was heated in a sealed tube under microwave irradiation at 120° C. for 10 min with stirring. The reaction mixture was cooled to room temperature and solvent was removed under reduced pressure. The crude material was partitioned between dichloromethane and water. The aqueous phase was extracted with dichloromethane. The combined extracts were dried over MgSO₄ and concentrated. The residue was chromatographed to give 1.03 g of (S)—N-(3'-carbamoyl-[1,1'-biphenyl]-3-yl)-3-methyl-4-(quinolin-2-ylmethyl) piperazine-1-carboxamide, as a white solid.

¹H NMR (500 M Hz, CDCl₃) δ 8.16 (d, 1H, J=7 Hz); 8.02 (d, 1H, J=7 Hz); 8.01 (s, 1H); 7.81 (d, 1H, J=7 Hz); 7.68-7.73 (m, 3H); 7.65 (d, 1H, J=5 Hz); 7.58-7.52 (m, 2H); 7.41-7.46 (m, 2H); 7.32 (t, 1H, J=7.5 Hz); 7.21 (d, 1H, J=7.5 Hz); 6.99 (s, 1H); 6.45 (bs, 1H); 6.48 (bs, 1H); 4.24 (d, 1H, J=12 Hz); 3.86 (d, 1H, J=13 Hz); 3.74 (td, 1H, J=12.5 Hz); 3.63 (d, 1H, J=14 Hz); 3.24 (td, 1H, J=10 Hz, J=3 Hz); 3.03 (dd, 1H, J=13 Hz, J=9 Hz); 2.77 (dt, 1H, J=12 Hz, J=4.0 Hz); 2.64-2.59 (m, 1H); 2.36 (t, J=12.5 Hz, J=3.0 Hz); 1.19 (d, 3H, J=6.5 Hz)

Examples 2-20 were Prepared According to Method A

Example 2: (R)—N-(3'-carbamoyl-[1,1'-biphenyl]-3-yl)-3-methyl-4-(quinolin-2-ylmethyl)piperazine-1-carboxamide ¹H-NMR: CDCl3 δ: 8.12 (d, 1H, J=8 Hz), 8.06 (d, 1H, J=8 Hz), 7.92 (s, 1H), 7.82 (d, 2H, J=8 Hz), 7.71-7.69 (m, 2H), 7.67 (d, 1H, J=8.5 Hz), 7.61 (td, 1H), 7.55-7.49 (m, 2H), 7.37 (t, 1H, J=8 Hz), 7.30 (dd, 1H, J1=1.5 Hz, J2=8 Hz), 7.24 (td, 1H), 6.45 (s, 1H), 4.29 (d, 1H, J=14 Hz), 3.84 (td, 1H), 3.72 (t, 1H, J=8.5 Hz), 3.68 (d, 1H, J=14.5 Hz), 3.29 (td, 1H), 3.06 (dd, 1H, J=9 Hz, J2=13 Hz), 2.83 (td, 1H, J=8.5 Hz), 2.73-2.67 (m, 1H), 2.43 (td, 1H), 1.24 (d, 3H, J=6.5 Hz)

Example 3: (S)—N-(3'-cyano-[1,1'-biphenyl]-3-yl)-2-methyl-4-(3-phenoxybenzyl)piperazine-1-carboxamide ¹H-NMR: CDCl3 δ: 8.04 (d, 1H, J=8 Hz), 7.98 (d, 1H, J=8 Hz), 7.92 (s, 1H), 7.81 (d, 2H, J=8 Hz), 7.71-7.69 (m, 2H), 7.65 (d, 1H, J=8.5 Hz), 7.61 (td, 1H), 7.55-7.49 (m, 2H), 7.37 (t, 1H, J=8 Hz), 7.30 (dd, 1H, J1=1.5 Hz, J2=8 Hz), 7.24 (td, 1H), 6.45 (s, 1H), 4.29 (d, 1H, J=14 Hz), 3.84 (td, 1H), 3.72 (t, 1H, J=8.5 Hz), 3.68 (d, 1H, J=14.5 Hz), 3.29 (td, 1H), 3.06 (dd, 1H, J=9 Hz, J2=13 Hz), 2.83 (td, 1H, J=8.5 Hz), 2.72-2.67 (m, 1H), 2.43 (td, 1H), 1.22 (d, 3H, J=6.5 Hz)

Example 4: (S)—N-(3'-carbamoyl-[1,1'-biphenyl]-3-yl)-2-methyl-4-(3-phenoxybenzyl) piperazine-1-carboxamide ¹H-NMR: CDCl3 δ: 8.15 (d, 1H, J=8 Hz), 8.09 (d, 1H, J=8 Hz), 7.93 (s, 1H), 7.82 (d, 2H, J=8 Hz), 7.71-7.67 (m, 4H), 7.66 (d, 1H, J=8.5 Hz), 7.61 (td, 1H), 7.55-7.49 (m, 2H), 7.37 (t, 1H, J=8 Hz), 7.30 (dd, 1H, J1=1.5 Hz, J2=8 Hz), 7.24 (td, 1H), 6.45 (s, 1H), 4.29 (d, 1H, J=14 Hz), 3.84 (td, 1H), 3.72 (t, 1H, J=8.5 Hz), 3.68 (d, 1H, J=14.5 Hz), 3.29 (td, 1H), 3.06 (dd, 1H, J=9 Hz, J2=13 Hz), 2.83 (td, 1H, J=8.5 Hz), 2.73-2.67 (m, 1H), 2.43 (td, 1H), 1.21 (d, 3H, J=6.5 Hz)

Example 5: (S)—N-(5-(3-cyanophenyl)pyridin-3-yl)-2-methyl-4-(3-phenoxybenzyl) piperazine-1-carboxamide ¹H-NMR: CDCl3 δ: 8.11 (d, 1H, J=7.5 Hz), 8.08 (d, 1H, J=8 Hz), 7.94 (s, 1H), 7.82 (d, 2H, J=8 Hz), 7.71-7.68 (m, 3H), 7.67 (d, 1H, J=8.5 Hz), 7.61 (td, 1H), 7.55-7.49 (m, 2H), 7.37 (t, 1H, J=8 Hz), 7.30 (dd, 1H, J1=1.5 Hz, J2=8 Hz), 7.24 (td, 1H), 6.45 (s, 1H), 4.29 (d, 1H, J=14 Hz), 3.84 (td, 1H), 3.72 (t, 1H, J=8.5 Hz), 3.68 (d, 1H, J=14.5 Hz), 3.29 (td, 1H), 3.06 (dd, 1H, J=9 Hz, J2=13 Hz), 2.83 (td, 1H, J=8.5 Hz), 2.73-2.67 (m, 1H), 2.43 (td, 1H), 1.24 (d, 3H, J=6.5 Hz)

Example 6: N-(3'-Carbamoyl-[1,1'-biphenyl]-3-yl)-4-(quinolin-3-ylmethyl)piperazine-1-carboxamide ¹H NMR (500 MHz, CDCl₃) δ ppm 8.15 (d, 1H, J=8.5 Hz), 8.08 (d, 1H, J=8.5 Hz), 8.03 (s, 1H), 7.82 (d, 1H, J=8.5 Hz), 7.75-7.70 (m, 3H), 7.63 (d, 2H, J=8.5 Hz), 7.54 (t, 1H, J=7.5 Hz), 7.48 (t, 1H, J=7.5 Hz), 7.40-7.33 (m, 2H), 6.70 (s, 1H), 3.88 (s, 2H), 3.57 (t, 4H, J=4.5 Hz), 2.60 (t, 4H, J=4.5 Hz)

Example 7: N-(3'-carbamoyl-[1,1'-biphenyl]-3-yl)-4-phenylpiperidine-1-carboxamide ¹H NMR (500 MHz, CDCl₃) δ ppm 7.85 (s, 1H); 7.82 (d, 1H, J=7.5 Hz); 7.56 (s, 1H); 7.62 (d, 1H, J=7.0 Hz); 7.54 (t, 1H, J=8.0 Hz); 7.39 (t, 1H, J=8.0 Hz); 7.34-7.31 (m, 3H); 7.25-7.21 (m, 5H); 6.53 (S, 1H); 6.24 (d, 2H, J=13 Hz); 3.05 (t, 2H, J=12 Hz); 2.74 (tt, 1H, J=3.5 Hz, J=14 Hz) 1.96 (d, 2H, J=4.8 Hz); 1.75 (qd, 2H, J=14.0 Hz, J=4.0 Hz)

Example 8: N-(3'-carbamoyl-[1,1'-biphenyl]-3-yl)-4-(9H-fluoren-9-yl)piperazine-1-carboxamide ¹H NMR (500 MHz, CDCl₃) δ ppm 8.14 (d, 1H, J=8.5 Hz), 8.09 (d, 1H, J=8 Hz), 8.03 (s, 1H), 7.80 (d, 1H, J=8.5 Hz), 7.75-7.70 (m, 3H), 7.64 (d, 2H, J=8.5 Hz), 7.56 (t, 1H, J=7.5 Hz), 7.48 (t, 1H, J=7.5 Hz), 7.40-7.33 (m, 2H), 6.70 (s, 1H), 3.88 (s, 2H), 3.57 (t, 4H, J=5 Hz), 2.60 (t, 4H, J=5 Hz)

Example 9: N-(3'-carbamoyl-[1,1'-biphenyl]-3-yl)-4-(pyridin-2-yl)piperazine-1-carboxamide ¹H NMR (500 MHz, CDCl₃) δ 8.86 (s, 1H); 8.73 (d, 1H, J=2 Hz); 8.54 (d, 1H, J=2 Hz); 8.24 (t, 1H, J=2 Hz); 8.16 (s, 1H); 8.02 (d, 1H, J=8.0 Hz); 7.89 (d, 1H, J=8.0 Hz); 7.72 (t, 1H, J=8.0 Hz); 7.27-7.32 (m, 4H); 7.20 (t, 1H, J=7.5 Hz); 4.31 (d, 2H, J=13 Hz); 2.93 (t, 2H, J=12 Hz); 2.77 (tt, J=3.5 Hz, J=12 Hz); 1.83 (d, 2H, J=12 Hz); 1.61 (qd, 2H, J=4 Hz, J=12 Hz)

Example 10: 4-([1,1'-biphenyl]-4-ylmethyl)-N-(3'-carbamoyl-[1,1'-biphenyl]-3-yl)piperazine-1-carboxamide ¹H NMR (500 MHz, CDCl₃) δ 7.85 (t, 1H, J=2 Hz); 7.81 (dd, 1H, J=12 Hz); 7.71 (t, 1H, J=5 Hz); 7.60 (d, 3H, J=12 Hz); 7.57 (s, 1H); 7.48-7.52 (m, 2H); 7.45 (t, 1H, J=8 Hz); 7.41 (t, 1H, J=8 Hz); 7.34-7.37 (m, 3H); 7.28-7.33 (m, 2H); 7.21 (dt, 1H, J=12 Hz); 6.48 (s, 1H); 3.62 (s, 2H); 3.54 (t, 4H, J=5 Hz); 2.54 (t, 4H, J=5 Hz)

Example 11: N-(3'-carbamoyl-[1,1'-biphenyl]-3-yl)-4-phenylpiperazine-1-carboxamide ¹H NMR (500 MHz, CDCl3) δ ppm 7.87 (s, 1H); 7.83 (d, 1H, J=7.5 Hz); 7.57 (s, 1H); 7.62 (d, 1H, J=7.0 Hz); 7.53 (t, 1H, J=8.0 Hz); 7.39 (t, 1H, J=8.0 Hz); 7.34-7.31 (m, 3H); 7.25-7.21 (m, 5H); 4.2 (t, 4H, J=5.0 Hz); 3.14 (t, 4H, J=5.0 Hz)

Example 12: N-(3'-carbamoyl-[1,1'-biphenyl]-3-yl)-4-(quinolin-2-ylmethyl)piperazine-1-carboxamide ¹H NMR (500 MHz, CDCl₃) δ 8.15 (d, 1H, J=8 Hz); 8.08 (d, 1H, J=8.5 Hz); 8.01 (s, 1H); 7.81 (d, 1H, J=8.5 Hz);

7.69-7.72 (m, 3H); 7.62 (d, 1H, J=8.5 Hz); 7.56 (t, 1H, J=2 Hz); 7.53 (t, 1H, J=7.0 Hz); 7.46 (t, 1H, J=7.0 Hz); 7.42 (d, 1H, J=8.5 Hz) 7.33 (t, 1H, J=8.0 Hz); 7.24 (t, 1H, J=8.0 Hz); 6.92 (s, 1H); 6.39 (bs, 1H); 5.69 (bs, 1H); 3.85 (s, 2H); 3.56 (t, 4H, J=4.5 Hz); 2.56 (t, 4H, J=4.5 Hz)

Example 13: N-(3'-cyano-[1,1'-biphenyl]-3-yl)-4-(quinolin-2-ylmethyl)piperazine-1-carboxamide $^1$H NMR (500 MHz, CDCl$_3$) δ ppm 8.15 (d, 1H, J=8.5 Hz), 8.07 (d, 1H, J=8.5 Hz), 8.02 (s, 1H), 7.82 (d, 1H, J=8.5 Hz), 7.75-7.70 (m, 3H), 7.63 (d, 2H, J=8.5 Hz), 7.54 (t, 1H, J=7.5 Hz), 7.48 (t, 1H, J=7.5 Hz), 7.40-7.33 (m, 2H), 6.70 (s, 1H), 3.86 (s, 2H), 3.57 (t, 4H, J=4.5 Hz), 2.61 (t, 4H, J=4.5 Hz).

Example 14: N-(3-phenoxyphenyl)-4-(quinolin-2-ylmethyl)piperazine-1-carboxamide $^1$H NMR (500 MHz, CDCl$_3$) δ 8.15 (d, 1H, J=8 Hz); 8.07 (d, 1H, J=8 Hz); 7.81 (d, 1H, J=8 Hz); 7.71 (t, 1H, J=7.5 Hz); 7.62 (d, 1H, J=7.5 Hz); 7.53 (t, 1H, J=8.0 Hz); 7.29 (t, 1H, J=8.0 Hz); 7.21 (t, 1H, J=8.0 Hz); 6.99-7.11 (m, 5H); 6.67 (d, 1H, J=10 Hz); 6.37 (s, 1H); 3.86 (s, 2H); 3.50 (t, 4H, J=5 Hz); 2.58 (t, 4H, J=5 Hz)

Example 15: N-(3'-cyano-[1,1'-biphenyl]-3-yl)-4-phenylpiperidine-1-carboxamide $^1$H NMR (500 MHz, CDCl$_3$) δ ppm 7.87 (s, 1H); 7.83 (d, 1H, J=7.5 Hz); 7.57 (s, 1H); 7.62 (d, 1H, J=7.0 Hz); 7.53 (t, 1H, J=8.0 Hz); 7.39 (t, 1H, J=8.0 Hz); 7.34-7.31 (m, 3H); 7.25-7.21 (m, 5H); 6.53 (S, 1H); 6.25 (d, 2H, J=13 Hz); 3.04 (t, 2H, J=12 Hz); 2.75 (tt, 1H, J=3.5 Hz, J=14 Hz) 1.95 (d, 2H, J=4.8 Hz); 1.76 (qd, 2H, J=14.0 Hz, J=4.0 Hz)

Example 16: N-(5-(3-cyanophenyl)pyridin-3-yl)-4-phenylpiperidine-1-carboxamide $^1$H NMR (500 MHz, CDCl$_3$) δ ppm 8.34 (s, 1H); 7.83 (d, 1H, J=7.5 Hz); 7.57 (s, 1H); 7.62 (d, 1H, J=7.0 Hz); 7.51 (t, 1H, J=8.0 Hz); 7.42 (t, 1H, J=8.0 Hz); 7.34-7.31 (m, 3H); 7.25-7.21 (m, 5H); 6.53 (S, 1H); 6.25 (d, 2H, J=13 Hz); 3.04 (t, 2H, J=12 Hz); 2.75 (tt, 1H, J=3.5 Hz, J=14 Hz) 1.95 (d, 2H, J=4.8 Hz); 1.76 (qd, 2H, J=14.0 Hz, J=4.0 Hz)

Example 17: 4-([1,1'-biphenyl]-3-ylmethyl)-N-(3'-cyano-[1,1'-biphenyl]-3-yl)piperazine-1-carboxamide $^1$H-NMR: CDCl$_3$ δ: 8.24 (d, 1H, J=8 Hz), 8.06 (d, 1H, J=8 Hz), 7.92 (s, 1H), 7.82 (d, 2H, J=8 Hz), 7.70-7.68 (m, 4H), 7.67 (d, 1H, J=8.5 Hz), 7.61 (td, 1H), 7.55-7.49 (m, 2H), 7.37 (t, 1H, J=8 Hz), 7.30 (dd, 1H, J1=1.5 Hz, J2=8 Hz), 7.24 (td, 1H), 6.45 (s, 1H), 4.29 (d, 1H, J=14 Hz), 3.82 (td, 1H), 3.72 (t, 1H, J=8.5 Hz), 3.67 (d, 1H, J=14.5 Hz), 3.28 (td, 1H), 3.06 (dd, 1H, J=9 Hz, J2=13 Hz), 2.83 (td, 1H, J=8.5 Hz), 2.71-2.67 (m, 1H), 2.43 (td, 1H), 1.24 (d, 3H, J=6.5 Hz)

Example 18: N-(3'-carbamoyl-[1,1'-biphenyl]-3-yl)-4-(3-phenoxybenzyl)piperazine-1-carboxamide $^1$H-NMR: CDCl$_3$ δ: 8.16 (d, 1H, J=8 Hz), 8.10 (d, 1H, J=8 Hz), 7.94 (s, 1H), 7.85 (d, 2H, J=8 Hz), 7.71-7.69 (m, 3H), 7.66 (d, 1H, J=8.5 Hz), 7.61 (td, 1H), 7.55-7.48 (m, 2H), 7.37 (t, 1H, J=8 Hz), 7.29 (dd, 1H, J1=1.5 Hz, J2=8 Hz), 7.21 (td, 1H), 6.45 (s, 1H), 4.28 (d, 1H, J=14 Hz), 3.85 (td, 1H), 3.72 (t, 1H, J=8.5 Hz), 3.69 (d, 1H, J=14.5 Hz), 3.29 (td, 1H), 3.06 (dd, 1H, J=9 Hz, J2=13 Hz), 2.83 (td, 1H, J=8.5 Hz), 2.72-2.67 (m, 1H), 2.43 (td, 1H), 1.25 (d, 3H, J=6.5 Hz)

Example 19: (S)—N-(3'-cyano-[1,1'-biphenyl]-3-yl)-3-methyl-4-(quinoliylmethyl)piperazine-1-carboxamide 1H-NMR (500 MHz CDCl$_3$) δ 8.15 (d, 1H, J=8 Hz), 8.06 (d, 1H, J=8 Hz), 7.85 (s, 1H), 7.82 (d, 2H, J=8 Hz), 7.72-7.69 (m, 2H), 7.67 (d, 1H, J=8.5 Hz), 7.61 (td, 1H), 7.55-7.49 (m, 2H), 7.37 (t, 1H, J=8 Hz), 7.30 (dd, 1H, J=1.5 Hz, J=8 Hz), 7.22 (td, 1H), 6.45 (s, 1H), 4.29 (d, 1H, J=14 Hz), 3.84 (td, 1H), 3.72 (t, 1H, J=8.5 Hz), 3.68 (d, 1H, J=14.5 Hz), 3.29 (td, 1H), 3.06 (dd, 1H, J=9 Hz, J=13 Hz), 2.83 (td, 1H, J=8.5 Hz), 2.73-2.67 (m, 1H), 2.43 (td, 1H), 1.24 (d, 3H, J=6.5 Hz)

Example 20: N-(3'-Cyano-[1,1'-biphenyl]-3-yl)-4-oxospiro[chromane-2,4'-piperidine]-1'-carboxamide $^1$H-NMR: DMSO-d6 δ: 8.71 (s, 1H), 8.04 (s, 1H), 7.95 (d, 1H, J=8 Hz), 7.83 (t, 2H, J=2 Hz), 7.74 (dd, 1H, J=1 Hz, J=7.5 Hz), 7.68 (t, 1H, J=8 Hz), 7.62-7.55 (m, 2H), 7.63 (t, 1H, J=7.5 Hz), 7.31 (d, 1H, J=8 Hz), 7.15-7.05 (m, 3H), 3.92 (td, 2H), 3.270 (t, 2H, J=11 Hz), 2.89 (s, 2H), 1.94 (d, 2H, J=13 Hz), 1.76-1.70 (m, 2H)

Method B: Synthesis of Imidazolyl Ureas 10

Imidazolyl ureas 10 (Scheme II) were synthesized by reaction of substituted piperazines 3 (Scheme I) or commercially available aryl piperidines derivatives with 4-nitrophenyl 4-phenyl-1H-imidazole-1-carboxylate 9 in THF or DCM without or with a base as triethylamine. Intermediate 9 was synthesized by treatment of 4-nitrophenyl chloroformate with commercially available 4-phenyl imidazole 8.

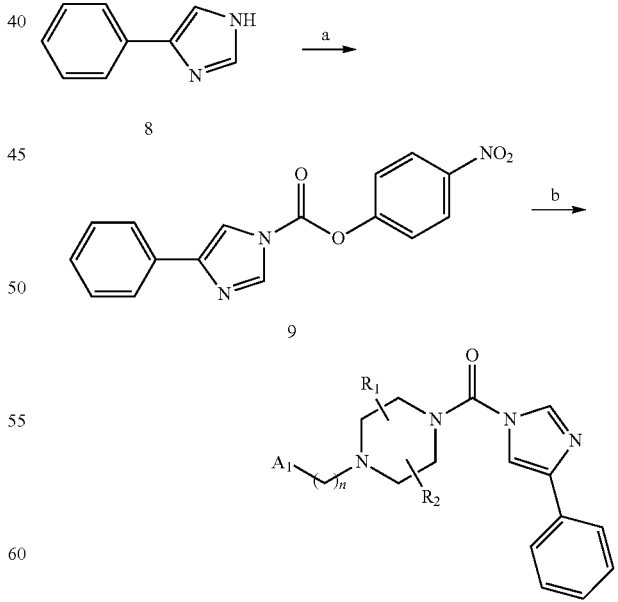

Scheme II

Reagents (a) 4-Nitrophenyl chloroformate, Et$_3$N, CH$_2$Cl$_2$, rt.; (b) 3, CH$_2$Cl$_2$, rt, 2 h.

The Following Examples were Prepared by Following Method B

Synthesis of Example 21 (S)-(4-([1,1'-biphenyl]-3-ylmethyl)-3-methylpiperazin-1-yl)(4-phenyl-1H-imidazol-1-yl)methanone Step a) Synthesis of 4-phenylimidazole-4-nitrophenyl carboxylate 9

To solution of 4-phenyl imidazole (2.2 g, 15.2 mmol) and triethylamine (2.42 mL, 16.7 mmol) in dry THF (20 mL) at 0° C., was added 4-nitrophenyl chloroformate (3.1 g, 15.2 mmol) over 15 min period. The reaction mixture was allowed to warm to room temperature. After 6 hours, the mixture was diluted with EtOAc (100 mL) and washed with saturated aqueous $NaHCO_3$ (20 mL). The organic layer was dried over $MgSO_4$ and concentrated. The residue was chromatographed to give 2.56 g of 4-phenylimidazole-4-nitrophenyl carboxylate 9 as a yellowish white solid.

$^1$H NMR (500 M Hz, $CDCl_3$) δ 8.30 (d, 2H, J=7.50 Hz); 7.72 (d, 2H, J=7.50 Hz); 7.50 (d, 2H, J=7.0 Hz); 7.45-7.41 (m, 4H); 7.28 (s, 1H)

Step b) Synthesis of (S)-(4-([1,1'-biphenyl]-3-ylmethyl)-3-methylpiperazin-1-yl)(4-phenyl-1H-imidazol-1-yl)methanone To a solution of (S)-1-([1,1'-biphenyl]-3-ylmethyl)-2-methylpiperazine (Scheme I, step b) (0.8 g, 3.17 mmol) in dichloromethane was added 4-phenylimidazole-4-nitrophenyl carboxylate (1.13 g, 3.64 mmol) 9 and mixture was stirred at room temperature for 2 hours. Solvent was removed under reduced pressure. The residue was chromatographed to give (4-([1,1'-biphenyl]-3-ylmethyl)piperazin-1-yl)(4-phenyl-1H-imidazol-1-yl)methanone 21 (1.09 g) as a white solid.

1H NMR (500 MHz, CDCl3) 7.98 (s, 1H); 7.81 (d, 2H, J=8.0 Hz); 7.53 (s, 1H); 7.41 (t, 2H, J=7.5 Hz); 7.34 (dt, 1H, J=8.0 Hz, J=2.0 Hz); 7.11-6.92 (m, 5H, J=8.0 Hz); 6.88-6.81 (m, 4H); 3.97 (dt, 1H, J=13.0 Hz, J=4.5 Hz); 3.85 (dd, 1H, J=13.0 Hz, J=2.0 Hz); 3.72-3.6 (m, 3H); 3.19 (qd, 2H, J=13.0, J=3.5 Hz); 2.30 (s, 3H), 1.03 (d, 3H, J=6.0 Hz).

Examples 22-34 were Prepared According to Method B

Example 22: 4'(4-Bromo-1H-imidazole-1-carbonyl)spiro[chroman-2,1'-cyclohexan]-4-one $^1$H NMR (500 MHz, $CDCl_3$) 7.89 (d, 1H, J=7.5 Hz); 7.77 (d, 1H, J=2.0 Hz); 7.53 (t, 1H, J=8.0 Hz), 7.18 (d, 1H, J=1.0 Hz); 7.06 (t, 1H, J=7.5 Hz, J=1.0 Hz); 7.01 (d, 1H, J=8.0 Hz); 3.96 (d, 2H, J=13.0 Hz), 3.54 (dt, 2H, J=13.0 Hz, J=2.0 Hz); 2.77 (s, 2H); 2.20 (d, 2H, J=13.0 Hz), 1.74 (dt, 2H, J=13.5 Hz, J=5.0 Hz).

Example 23: (3-Methyl-4-phenylpiperazin-1-yl)(4-phenyl-1H-imidazol-1-yl)methanone $^1$H NMR (500 MHz, $CDCl_3$) 7.96 (s, 1H); 7.81 (d, 2H, J=8.0 Hz); 7.51 (s, 1H); 7.41 (t, 2H, J=7.5 Hz); 7.30 (t, 3H, J=7.5 Hz); 6.96 (d as m, 3H, J=8.0 Hz); 4.05 (dt, 1H, J=13.0 Hz, J=4.0 Hz); 3.90-3.82 (m, 1H); 3.77 (t, as d, half of A'X' system, 2H, J=4.0 Hz); 3.56 (ddd, 1H, J=26.0 J=14.0 Hz J=5.0 Hz); 3.26 (d as m, 1H, J=12.0 Hz, J=3.5 Hz); 2.90 (dt, 1H, J=13.0 Hz, J=3.0 Hz); 1.06 (d, 3H, J=7.0 Hz).

Example 24: (3-Methyl-4-phenylpiperazin-1-yl)(4-phenyl-1H-imidazol-1-yl)methanone $^1$H NMR (500 MHz, $CDCl_3$) 7.92 (s, 1H); 7.79 (d, 2H, J=8.0 Hz); 7.51 (s, 1H); 7.39 (t, 2H, J=7.5 Hz); 7.28 (dt, 1H, J=8.0 Hz, J=2.0 Hz); 7.10 (d, 2H, J=8.0 Hz); 6.89 (d, 2H, J=8.0 Hz); 3.94 (dt, 1H, J=13.0 Hz, J=4.5 Hz); 3.80 (dd, 1H, J=13.0 Hz, J=2.0 Hz); 3.72-3.61 (m, 3H); 3.18 (qd, 2H, J=13.0, J=3.5 Hz); 1.01 (d, 3H, J=6.0 Hz).

Example 25: (3-Methyl-4-(p-tolyl)piperazin-1-yl)(4-phenyl-1H-imidazol-1-yl)methanone $^1$H NMR (500 MHz, $CDCl_3$) 7.96 (s, 1H); 7.81 (d, 2H, J=8.0 Hz); 7.51 (s, 1H); 7.41 (t, 2H, J=7.5 Hz); 7.30 (dt, 1H, J=8.0 Hz, J=2.0 Hz); 7.11 (d, 2H, J=8.0 Hz); 6.88 (d, 2H, J=8.0 Hz); 3.96 (dt, 1H, J=13.0 Hz, J=4.5 Hz); 3.80 (dd, 1H, J=13.0 Hz, J=2.0 Hz); 3.72-3.6 (m, 3H); 3.18 (qd, 2H, J=13.0, J=3.5 Hz); 2.30 (s, 3H), 1.01 (d, 3H, J=6.0 Hz).

Example 26: (4-(3-(Benzyloxy)phenyl)-3-methylpiperazin-1-yl)(4-phenyl-1H-imidazol-1-yl)methanone $^1$H NMR (500 MHz, $CDCl_3$) 7.91 (s, 1H); 7.81 (d, 2H, J=8.0 Hz); 7.51 (s, 1H); 7.41 (t, 2H, J=7.5 Hz); 7.30 (dt, 1H, J=8.0 Hz, J=2.0 Hz); 7.11-6.92 (m, 5H, J=8.0 Hz); 6.88-6.81 (m, 4H); 3.96 (dt, 1H, dr=13.0 Hz, J=4.5 Hz); 3.80 (dd, 1H, J=13.0 Hz, J=2.0 Hz); 3.72-3.6 (m, 3H); 3.18 (qd, 2H, J=13.0, J=3.5 Hz); 2.30 (s, 3H), 1.01 (d, 3H, J=6.0 Hz).

Example 27: (4-(3-Hydroxyphenyl)-3-methylpiperazin-1-yl)(4-phenyl-1H-imidazol-1-yl)methanone $^1$H NMR (500 MHz, $CDCl_3$) 7.91 (s, 1H); 7.79 (d, 2H, J=8.0 Hz); 7.49 (s, 1H); 7.39 (t, 2H, J=7.5 Hz); 7.30 (dt, 1H, J=8.0 Hz, J=2.0 Hz); 7.11 (d, 2H, J=8.0 Hz); 6.88 (d, 2H, J=8.0 Hz); 3.96 (dt, 1H, J=13.0 Hz, J=4.5 Hz); 3.80 (dd, 1H, J=13.0 Hz, J=2.0 Hz); 3.72-3.6 (m, 3H); 3.18 (qd, 2H, J=13.0, J=3.5 Hz); 2.30 (s, 3H), 1.01 (d, 3H, J=6.0 Hz).

Example 28: (4-(Bis 4-fluorophenyl)piperazin-1-yl)(4-bromo-1H-imidazol-1-yl)methanone $^1$H NMR (500 MHz, $CDCl_3$) 7.74 (s, 1H); 7.76 (d, 1H, J=8.0 Hz); 7.34 (dd, 4H, J=8.5 Hz, J=5.5 Hz); 7.14 (d, 1H, J=2.0 Hz); 7.01 (t, 4H, J=8.5 Hz); 7.34-7.5 (m, 5H); 7.24-7.12 (m, 2H); 4.29 (s, 1H); 3.62 (t, 4H, J=5.0 Hz); 2.45 (t, 4H, J=5.0 Hz).

Example 29: (4-(Bis(4-fluorophenyl)methyl)piperazin-1-yl)(4-phenyl-1H-imidazol-1-yl)methanone $^1$H NMR (500 MHz, $CDCl_3$) 7.88 (s, 1H); 7.76 (d, 1H, J=8.0 Hz); 7.43 (s, 1H), 7.39 (t, 2H, J=8.0 Hz), (dd, 4H, J=8.0 Hz, J=5.5 Hz); 7.28 (t, 1H, J=7.0 Hz); 7.00 (t, 4H, J=8.0 Hz); 4.30 (s, 1H); 3.67 (t, 4H, J=5.0 Hz); 2.47 (t, 4H, J=5.0 Hz).

Example 30: (4-Benzhydrylpiperazin-1-yl)(4-phenyl-1H-imidazol-1-yl)methanone $^1$H NMR (400 MHz, $CDCl_3$) 7.90 (s, 1H); 7.76 (d, 1H, J=8.0 Hz); 7.50-7.40 (m, 4H); 7.38 (t, 3H, J=8.5 Hz); 7.34-7.5 (m, 5H); 7.24-7.12 (m, 2H); 4.34 (s, 1H); 3.9-3.6 (m, 4H), 2.7-2.4 (m, 4H)

Example 31: (4-Benzhydrylpiperazin-1-yl)(5-benzyl-1H-tetrazol-1-yl)methanone $^1$H NMR (400 MHz, CDCl$_3$) 7.32 (d, 2H, J=8.0 Hz); 7.30-7.27 (m, 8H); 7.25 (d, 2H, J=8.0 Hz); 7.21-7.17 (m, 3H); 4.42 (s, 2H); 4.13 (s, 1H); 3.62 (t, 2H, J=4.0 Hz); 3.05 (t, 2H, J=4.0 Hz); 2.35 (t, 2H, J=4.0 Hz); 1.95 (t, 2H, J=4.0 Hz)

Example 32: (5-Benzyl-1H-tetrazol-1-yl)(4-(bis(4-fluorophenyl)methyl)piperazin-1-yl)methanone $^1$H NMR (400 MHz, CDCl$_3$) 7.43 (d, 2H, J=8.0 Hz); 7.40-7.34 (m, 7H); 7.10-6.90 (m, 4H); 4.60 (s, 2H); 4.30 (s, 1H), 3.85-3.73 (m, 4H); 2.60-2.50 (m, 4H)

Example 33: (3-(Carbomethoxy)-1H-1,2,4-triazol-1-yl)(4-(bis(4-fluorophenyl)methyoxy) pipe-ridin-1yl) methanone $^1$H NMR (400 MHz, CDCl$_3$) δ 8.08 (s, 1H), 7.28 (m, 4H); 7.02 (m, 4H); 5.5 (s, 1H); 4.01 (s, 3H); 3.95-3.83 (m, 1H); 3.82-3.68 (m, 4H) 1.95-65 (m, 4H)

Example 34: 4'-(4-Bromo-1H-imidazole-1-carbonyl)spiro[chromane-2,1'-cyclohexan]-4-one $^1$H NMR (500 MHz, CDCl$_3$) 7.89 (d, 1H, J=7.5 Hz); 7.77 (d, 1H, J=2.0 Hz); 7.53 (t, 1H, J=8.0 Hz); 7.18 (d, 1H, J=1.0 Hz); 7.06 (t, 1H, J=7.5 Hz, J=1.0 Hz); 7.01 (d, 1H, J=8.0 Hz); 3.96 (d, 2H, J=13.0 Hz); 3.54 (dt, 2H, J=13.0 Hz, J=2.0 Hz); 2.77 (s, 2H); 2.20 (d, 2H, J=13.0 Hz), 1.74 (dt, 2H, J=13.5 Hz, J=5.0 Hz).

Method C Syntheses of Substituted Piperazine Carbamates 17

Commercially available substituted aldehydes 11 (Scheme III) were treated with alkyl, cycloalkyl or aryl Grignard reagents to give substituted benzyl alcohols 12, which were converted to corresponding chlorides 13 with thionyl chloride. Chlorides 13 were further treated with piperazine to produce alkylated piperazines 14. Commercially available phenols 15 were converted to chloroformates 16 using triphosgene. Final piperazine carbamates 17 were formed by reaction of chloroformates 16 with alkylated piperazine 14

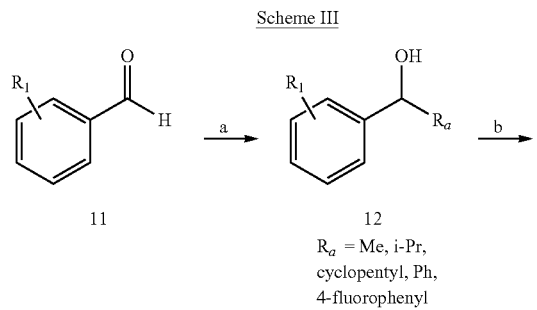

Scheme III

Reagents: (a) alkyl, cycloalkyl, or aryl-MgBr, THF, -20° C.; (b) SOCl$_2$, CH$_2$Cl$_2$, reflux: (c) piperazine, EtOH, reflux; (d) (COCl$_3$)$_2$CO, DIEA, CH$_2$Cl$_2$, 0° C.-rt, 1 h; (e) piperazines 14, Et$_3$N, CH$_2$Cl$_2$, rt.

The Following Examples were Prepared by Following Method C

Example 35 Synthesis of 3-cyanophenyl 4-(2-methyl-1-phenylpropyl)piperazine-1-carboxylate Step a) Synthesis of 2-methyl-1-phenylpropan-1-ol (12, R$_1$=H, R$_a$=isopropyl)

To a solution of commercially available benzaldehyde (1.30 g, 12.30 mmol) in THF (25 mL) at −20° C. under a nitrogen atmosphere was added isopropylmagnesium bromide (4.1 mL, 3.0 M solution in diethyl ether) over 15 min with stirring. Reaction mixture was stirred for additional 1 h at −20° C., and upon completion (monitored by TLC) the reaction mixture was diluted with saturated aqueous NH$_4$Cl solution (10 mL). The aqueous layer was extracted with EtOAc and the combined organic layer was dried over MgSO$_4$ and concentrated in vacuo. The crude material was purified by column chromatography on silica gel to give benzyl alcohol 12 (1.73 g, 11.56 mmol) as colorless liquid.

$^1$H NMR (400 MHz, CDCl$_3$) δ 7.35-7.25 (m, 5H); 4.12 (d, 1H, J=6.0 Hz); 2.05-1.90 (m, 1H); 1.92 (brs, 1H) 1.31 (d, 3H, J=6.0 Hz); 1.19 (d, 3H, J=6.0 Hz)

Step b) Synthesis of (1-chloro-2-methylpropyl)benzene (13, $R_1$=H, $R_a$=isopropyl)

To a solution of benzyl alcohol 12 (900 mg, 6.0 mmol) in dichloromethane (50 mL) at room temperature was added thionyl chloride (1.1 mL, 15 mmol) drop wise over 10 min. The reaction was refluxed for 1 hour and then reaction mixture was concentrated in vacuo to give 0.96 g of (1-chloro-2-methylpropyl)benzene 13 as a colorless viscous liquid, which was used to the next step without any further purification.

$^1$H NMR (400 MHz, CDCl$_3$) δ 7.36-7.27 (m, 5H); 4.67 (d, 1H, J=6.0 Hz); 2.05-1.90 (m, 1H); 1.92 (brs, 1H) 1.31 (d, 3H, J=6.0 Hz); 1.19 (d, 3H, J=6.0 Hz)

Step c) Synthesis 1-(2-Methyl-1-phenylpropyl)piperazine (14, $R_1$=H, $R_a$=isopropyl)

A solution of name (0.84 g, 5.0 mmol) in ethanol (10 mL) was treated with piperazine, (2.15 g, 25.0 mmol) the resulting mixture was heated in a sealed tube at 80° C. for 2 hours with stirring. The reaction mixture was cooled to room temperature. The solvent was removed in vacuo and the residue partitioned between dichloromethane and saturated aqueous NaHCO$_3$ solution. The aqueous layer was further extracted with dichloromethane. The combined organic layer was washed with brine, dried over MgSO4 and solvent removed in vacuum to give 0.98 g of 1-(2-methyl-1-phenylpropyl)piperazine as pale yellow viscous liquid.

$^1$H NMR (400 MHz, CDCl$_3$) δ 7.36-7.27 (m, 5H); 4.67 (d, 1H, J=6.0 Hz); 3.07 (d, 1H, J=8.0 Hz); 2.50-2.40 (m, 4H); 2.40-2.30 (m, 4H); 2.05-1.90 (m, 1H); 2.10 (brs, 1H) 1.31 (d, 3H, J=4.0 Hz); 1.19 (d, 3H, J=8.0 Hz)

Step d) Synthesis of 3-cyanophenyl chloroformate (16, $R_2$=CN, $R_3$=H, $W_1$=CH)

To a stirred solution of triphosgene (0.5 g, 1.70 mmol) in dichloromethane (15 mL) at 0° C. under argon atmosphere was added a mixture of commercially available 3-cyanophenol (0.58, 4.87 mmol) and N,N-diisopropylethyl amine (0.87 mL, 5.0 mmol) in methylene chloride (15 mL), drop-wise over 10 min. After addition was complete the reaction mixture was stirred at the same temperature for 1 h. When the phenol was consumed (TLC analysis) the mixture was diluted with ice-cold water, the aqueous layer was extracted with methylene chloride (2×10 mL), the combined organic layer was dried over MgSO$_4$, and the solvent was removed under reduced pressure to give 0.75 mg of 3-cyanophenyl chloroformate as a pale yellow solid material, which was used in the next step without any further purification

Step e) 3-Cyanophenyl 4-(2-methyl-1-phenylpropyl) piperazine-1-carboxylate (17, $R_1$=H, $R_a$=isopropyl, $R_2$=CN, $R_3$=H, $W_1$=CH)

To a stirred solution of 3-cyanophenyl chloroformate (0.55 g, 3.0 mmol) in methylene chloride (20 mL) at room temperature under argon atmosphere were added 1-(2-methyl-1-phenylpropyl)piperazine (0.79 g, 3.6 mmol) and triethylamine (0.61 mL, 4.2 mmol) sequentially. The resulting mixture was stirred at room temperature for 2 hours. after the completion of reaction, (chloroformate was monitored by TLC), mixture was diluted with water, the aqueous layer was extracted with methylene chloride (2×10 mL), the combined organic layer was dried over MgSO$_4$ and the solvent removed under reduced pressure to give a crude material, purified by column chromatography on silica gel to give 0.8 g of 3-cyanophenyl 4-(2-methyl-1-phenylpropyl) piperazine-1-carboxylate as a white solid.

$^1$H NMR (400 MHz, CDCl$_3$) δ 7.45 (d, 1H, J=8.0 Hz); 7.42 (t, 2H, J=8.0), 7.37 (t, 1H, J=2.0 Hz); 7.34 (t, 2H, J=8.0) overlapping with (m, 1H); 7.30-7.27 (m, 1H), 7.13 (d, 2H, J=8.0 Hz); 3.70-3.40 (m, 4H); 3.07 (d, 1H, J=8.0 Hz); 2.50-2.40 (m, 2H); 2.40-2.30 (m, 2H); 2.32-2.20 (m, 1H); 1.02 (d, 3H, J=4.0); 0.74 (d, 3H, J=8.0)

Examples 36-45 were Prepared According to Method C

Example 36: 3-Cyanophenyl 4-(1-phenylethyl)piperazine-1-carboxylate $^1$H NMR (400 MHz, CDCl$_3$) δ 7.45 (d, 4H, J=8.0 Hz); 7.33-7.26 (m, 5H); 3.65-3.63 (m, 2H); 3.57-3.55 (m, 2H), 3.46 (s, 1H), 2.53-2.55 (m, 2H); 2.48-2.46 (m, 2H); 1.41 (s, 3H)

Example 37: 3-Cyanophenyl 4-(cyclopentyl(phenyl) methyl)piperazine-1-carboxylate $^1$H NMR (400 MHz, CDCl$_3$) δ 7.44 (d, 1H, J=8.0 Hz); 7.41 (t, 2H, J=8.0 Hz), 7.36 (t, 1H, J=2.0 Hz); 7.34 (t, 2H, J=8.0 Hz) overlapping with (m, 1H); 7.29-7.26 (m, 1H), 7.13 (d, 2H, J=8.0 Hz); 3.70-3.40 (m, 4H); 3.25 (d, 1H, J=7.0 Hz); 2.60-2.45 (m, 3H); 2.40-2.30 (m, 2H); 1.95-1.85 (m, 1H); 1.52-1.48 (m, 6H)

Example 38: 3-Cyano-5-hydroxyphenyl 4-benzhydrylpiperazine-1-carboxylate $^1$H NMR (400 MHz, CDCl$_3$) δ 7.43 (d, 4H, J=8.0 Hz); 7.30 (t, 4H, J=8.0 overlapping with m 1H @ 7.29-7.27); 7.27-7.25 (m, 2H); 7.21 (t, 2H, J=8.0); 4.28 (s, 1H); 3.67-3.60 (m, 2H); 3.59-3.52 (m, 2H); 2.55-2.45 (m, 4H)

Example 39: 6-Chloropyridin-2-yl 4-benzhydrylpiperazine-1-carboxylate $^1$H NMR (400 M Hz, CDCl$_3$) δ 7.77 (d, 1H, J=8.0 Hz); 7.58-7.42 (m, 5H); 7.40-7.30 (m, 5H); 6.72 (d, 1H, J=8.0 Hz); 6.67 (d, 1H, J=8.0 Hz); 5.28 (s, 1H); 4.25-4.15 (m, 4H); 3.50-3.40 (m, 4H)

Example 40: 3-Cyanophenyl 4-(bis(4-fluorophenyl) methyl)piperazine-1-carboxylate $^1$H NMR (500 M Hz, CDCl$_3$) δ 7.48 (d as m, 1H, J=8.0 Hz); 7.44 (t, 1H, J=8.0 Hz); 7.42 (d, 1H, J=2.0 Hz); 7.36 (d as m, 3H, J=8.5 Hz); 7.35 (d, 2H, J=8.5 Hz); 6.99 (t, 7.36 4H, J=8.5 Hz) 3.69 (brs, 2H); 4.29 (s, 1H); 3.66 (brs, 2H); 3.57 (brs, 2H); 2.43 (t, 4H, J=5.0 Hz)

Example 41: 3-Cyanophenyl 4-(9H-fluoren-9-yl)piperazine-1-carboxylate $^1$H NMR (500 M Hz DMSO) δ 8.58 (d, 1H J=4.5 Hz); 7.85 (d, 1H, J=8.0 Hz); 7.79-7.77 (m as d overlapping with triplets, 2H), 7.65 (d, 1H, J=7.5 Hz, 2H), 7.41 (t, 2H, J=7.5 Hz); 7.34 (t, 2H, J=7.5 Hz); 5.02 (s, 1H); 3.58-3.53 (m, 2H); 3.46-3.41 (m, 2H); 2.65-2.55 (m, 4H).

Example 42: 4-Cyanopyridin-2-yl 4-(9H-fluoren-9-yl)piperazine-1-carboxylate $^{1}$H NMR (500 M Hz, CDCl$_3$) δ 8.58 (d, 1H J=4.5 Hz); 7.85 (d, 1H, J=8.0 Hz); 7.79-7.77 (m as d overlapping with triplets, 2H), 7.65 (d, 1H, J=7.5 Hz, 2H); 7.41 (t, 2H, J=7.5 Hz); 7.34 (t, 2H, J=7.5 Hz); 5.02 (s, 1H); 3.58-3.53 (m, 2H); 3.46-3.41 (m, 2H); 2.65-2.55 (m, 4H)

Example 43: 3-Cyanopyridin-2-yl 4-(9H-fluoren-9-yl)piperazine-1-carboxylate $^{1}$H NMR (500 M Hz, CDCl$_3$) δ 8.58 (d, 1H J=4.5 Hz); 7.82 (d, 1H, J=8.0 Hz); 7.79-7.77 (m, 2H), 7.63 (d, 1H, J=7.5 Hz, 2H); 7.41 (t, 2H, J=7.5 Hz); 7.34 (t, 2H, J=7.5 Hz); 5.02 (s, 1H); 3.58-3.53 (m, 2H); 3.46-3.41 (m, 2H); 2.65-2.55 (m, 4H)

Example 44: 3-Cyanophenyl 4-benzhydrylpiperazine-1-carboxylate $^{1}$H NMR (400 M Hz, CDCl$_3$) δ 7.52-7.49 (m, 2H); 7.4 (t, 1H, J=8.0 Hz); 7.39 (td, 1H, J=8.0 Hz, J=2.0 Hz); 7.37-7.34 (m, 5H); 7.31 (m, 1H); 3.69 (brs, 2H); 3.58 (s, 2H); 3.55 (brs, 2H); 3.26 (s, 2H); 2.53 (t, 4H, J=5.0 Hz)

Example 45: 5-Cyano-2-fluorophenyl 4-benzylpiperidine-1-carboxylate $^{1}$H NMR (400 MHz, CDCl$_3$) δ 7.55 (dd, 1H, J=7.0 Hz, J=2.0 Hz); 7.50 (ddd, 1H, J=7.0 Hz, J=2.0 Hz, J=2.0 Hz); 7.30 (t, 2H, J=7.0 Hz); 7.25-7.23 (m, 1H); 7.22 (t, 1H J=7.0 Hz); 7.16 (t, 1H J=7.0 Hz); 4.25 (d, 1H, J=13.0 Hz); 4.19 (d, 1H, J=13.0 Hz); 2.96 (t, 1H, J=13.0 Hz); 2.83 (t, 1H, J=13.0 Hz); 2.59 (d, 2H, J=6.8 Hz); 1.85-1.70 (1H, m overlapping with d at 1.75, 2H, J=13.0 Hz); 1.30 (dq, 2H, J=13.0 Hz, J=4.0 Hz)

Method D: Syntheses of Benzhydryl Piperidine Carbamates 22 and Benzyhydryloxy Piperidine Carbamates 25

Commercially available 1-(tert-butyl) 4-methyl piperidine-1,4-dicarboxylate 18 (Scheme Iv), was treated with phenyl, magnesium bromide solution in TI-IF to afford benzhydrol 19 which was converted by simultaneous dehydration and deprotection to piperidinium salt 20. Intermediate 20 was further reduced to piperidine salt 21 via catalytic hydrogenation. Final carbamates 22 were obtained by treating piperidine salt 21 with aryl chloroformates 16 (Scheme III). Benzhydrols 23 were converted into corresponding benzhydroxy piperidines 24 via acid-catalyzed reaction using Dean-Stark condenser. Carbamates 25 were obtained by reaction of benzhydroxy piperidines 24 with chloroformates 16.

Scheme IV

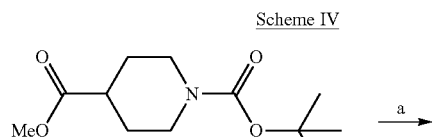

18

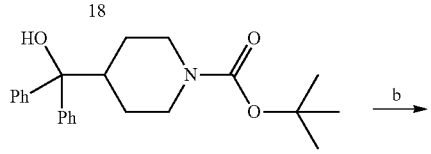

19

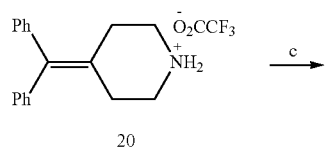

20

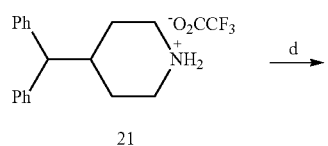

21

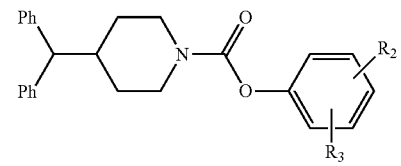

22

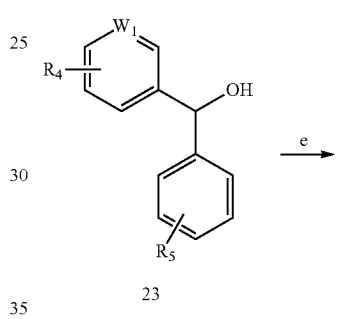

23

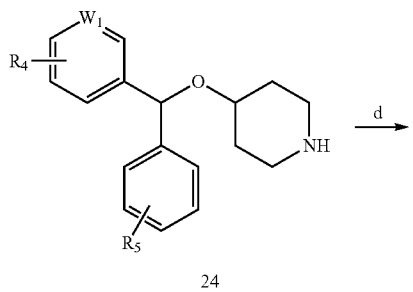

24

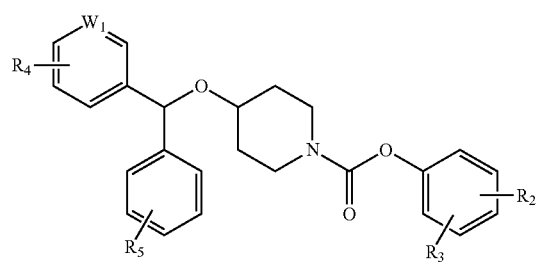

25

Reagents: (a) PhMgBr, THF, 0° C.-rt, 2 h; (b) TFA, CH$_2$Cl$_2$, rt; (c) H$_2$, Pd/C, MeOH, rt, overnight; (d) 16, Et$_3$N, DCM, rt; (e) p-TSA, 4-hydroxypiperidine, PhCH$_3$, reflux, 3-4 h The Following Examples were Prepared by Following Method D

Synthesis of Example 46, 3-Cyanophenyl 4-benzhydrylpiperidine-1-carboxylate

Step a) Synthesis of tert-butyl 4-(hydroxydiphenylmethyl)piperidine-1-carboxylate 19

A stirred solution of commercially available 1-(tert-butyl) 4-methyl piperidine-1,4-dicarboxylate 18 (4.86 g, 20 mmol) in THF (100 mL) at 0° C. was treated with phenyl magnesium bromide (1M solution in THF, 80 MO over 15 min. and stirred at room temperature for 1 h. Upon completion (monitored by TLC) the reaction mixture was quenched with saturated aqueous NH$_4$Cl solution (20 mL). The aqueous layer was extracted with EtOAc and the combined organic layer was washed with brine, dried over MgSO$_4$ and concentrated in vacuo. The crude material was purified by column chromatography on silica gel to give tert-butyl 4-(hydroxydiphenylmethyl)piperidine-1-carboxylate 5.6 g as a white solid.

$^1$H NMR (400 MHz, CDCl$_3$) δ 7.47 (d, 4H, J=8.0 Hz); 7.31 (t, 4H, J=8.0 Hz); 7.20 (t, 2H, J=8.0 Hz); 4.25-4.05 (m, 2H); 2.71 (t, 1H, J=12.0 Hz); 2.55 (dt, 1H, J=12.0 Hz, J=4.0 Hz); 2.12 (s, 1H); 1.55 (d, 2H, J=12.0 Hz); 1.35 (dq 2H, J=12.0 Hz, J=4.0 Hz)

Step b) Synthesis of 4-(diphenylmethylene)piperidinium trifluoro acetate 20

A solution of tert-butyl 4-(hydroxydiphenylmethyl)piperidine-1-carboxylate (5.5 g, 15.0 mmol) and TEA (5.8 mL, 75 mmol) in CH$_2$Cl$_2$ (100 mL) at room temperature was stirred overnight and then concentrated. The residue was triturated with 10% EtOAc:Hexane. The precipitating salt was isolated by filtration and dried to give 5.4 g of 4-(diphenylmethylene)piperidinium trifluoro acetate as a white solid.

$^1$H NMR (400 MHz, DMSO) δ 8.61 (brs, 1H); 8.34 (brs, 1H); 7.40-7.10 (m, 10H); 3.40-3.35 (m, 4H); Hz, J=4.0 Hz); 2.55-2.45 (m, 4H)

Step c) Synthesis of 4-(diphenylmethyl)piperidinium trifluoro acetate 21

A stirred solution of 4-(diphenylmethylene)piperidinium trifluoro acetate 20 (5.30 g, 14.52 mmol) in methanol was flushed with argon, 10% palladium on carbon (0.8 g, 15% wt/wt) was added and the mixture hydrogenated at atmospheric pressure overnight. The mixture was filtered over celite and celite was further washed with MeOH. The combined filtrate was concentrated in vacuo to afford 4.98 g of 4-(diphenylmethyl)piperidinium trifluoro acetate as a white solid, which was used for the next step without further purification.

$^1$H NMR (400 MHz, DMSO) δ 8.61 (brs, 1H); 8.34 (brs, 1H); 7.37-7.32 (m, 4H); 7.30-7.25 9m, 4H); 7.17-7.10 (m, 2H); 3.59 (d, 1H, J=8.0 Hz); 3.25-3.18 (m, 2H); 2.85-2.80 (m, 2H); 2.60-2.48 (m, 1H); 1.54 (d, 2H, J=12.0 Hz); 1.23 (q, 2H, J=12.0 Hz)

Step d) Synthesis of 3-cyanophenyl 4-benzhydrylpiperidine-1-carboxylate

To a stirred solution of 3-cyanophenyl chloroformate 16 (Scheme III, 0.64 g, 3.5 mmol,) in methylene chloride (50 mL) at room temperature under argon atmosphere were added a piperidine 21 (1.53 g, 4.2 mmol) and triethylamine (0.5 mL, 3.60 mmol). The resulting mixture was stirred at room temperature for 2 hours. After the completion of reaction, as monitored by TLC, the mixture was diluted with water, the aqueous layer was extracted with methylene chloride (2×20 mL), the combined organic layer was dried with MgSO$_4$, The solvent was removed under reduced pressure to give a crude material, which was purified by column chromatography on silica gel to afford 0.9 g of 3-cyanophenyl 4-benzhydrylpiperidine-1-carboxylate as a white solid.

$^1$H NMR (400 MHz, CDCl$_3$) δ 7.47-7.41 (m, 3H); 7.36 (dt, 1H, J=8.0, J=2.0); 7.32-7.25 (m, 9H); 7.22-7.15 (m, 2H); 4.20 (d, 2H, J=13.0 Hz); 3.54 (d, 1H J=6.8 Hz); 2.96 (dt, 2H, J=13.0, J=2.0); 2.42-2.30 (m, 1H); 1.67 (d, 2H, J=13.0); 1.20 (dq, 2H, J=13.0, J=2.0)

Step e) Synthesis of 4-(4-chlorophenyl)(2-chloropyridin-3-yl)methoxypiperidine (24, W$_1$=N, R$_4$=2-Cl, R$_5$=4-Cl)

A mixture of 4-(4-chlorophenyl)(2-chloropyridin-3-yl)methamol (2.54 g, 10.0 mmol; prepared according to Hart et al *Biorg. & Med. Chem. Lett.* 2009, 19: 4241-4244), 4-hydroxypiperidine (1.0 g, 10.0 mmol), and p-toluenesulfonic acid monohydrate (4.19 g 22.0 mmol) in toluene (50 mL) was refluxed with a Dean-Stark condenser for 3 h. After cooling to room temperature, the toluene solution was washed with saturated aqueous NaHCO$_3$, and dried over MgSO$_4$. The solvent was removed under reduced pressure to give 2.52 g of 4-(4-chlorophenyl)(2-chloropyridin-3-yl)methoxypiperidine as a pale yellow gum, $^1$H NMR (400 MHz, CDCl$_3$) δ 8.37 (dd, 1H, J=8.0 Hz, J=2.0 Hz); 7.82 (dd, 1H, J=8.0 Hz); 7.5-7.42 (m, 3H); 7.38-7.28 (m, 6); 5.90 (s, 1H); 3.72-3.65 (m, 1H); 3.32-3.55 (m, 4H); 2.10 9brs, 1H); 1.90-1.80 (m, 2H); 1.79-1.70 (m, 2H)

Step f) 3-Cyanophenyl 4-(4-chlorophenyl)(2-chloropyridin-3-yl)methoxy)piperidine-1-carboxylate 3-Cyanophenyl 4-(4-chlorophenyl)(2-chloropyridin-3-yl)methoxy)piperidine-1-carboxylate was prepared from a solution of 3-cyanophenyl chloroformate (Scheme III, 0.45 g, 2.5 mmol) methylene chloride (40 mL), 4-(4-chlorophenyl)(2-chloropyridin-3-yl)methoxypiperidine 24 (1.0 g, 3.0 mmol) and triethyl amine (0.86 mL, 6.20 mmol) to afford 0.84 g of 3-cyanophenyl 4-((4-chlorophenyl)(2-chloropyridin-3-yl)methoxy)piperidine-1-carboxylate as a white solid.

$^1$H NMR (400 MHz, CDCl$_3$) δ 8.34 (dd, 1H, J=8.0 Hz, J=2.0 Hz); 7.92 (d, 1H, J=8.0); 7.52-7.41 (m, 3H) 7.41-7.28 (m, 6H); 5.89 (s, 1H), 3.95-3.75 (m, 2H); 3.80-3.65 (m, 1H); 3.50-3.30 (m, 2H); 3.49-3.39 (m, 1H); 1.95-1.85 (m, 2H); 1.80-1.70 (m, 2H).

Examples 47-51, 54-58 were Synthesized by Method D

Example 47: 3-Cyanophenyl 4-(diphenylmethylene)piperidine-1-carboxylate $^1$H NMR (400 MHz, CDCl$_3$) δ 7.54-7.44 (m, 2H) overlapping with (d, @7.48 1H, J=8.0 Hz); 7.40 (d, 1H, J=8.0 Hz), 7.33 (t, 4H, J=7.2 Hz); 7.24 (t, 2H, J=7.2 Hz) 7.14 (d, 4H, J=8.0 Hz); 3.75-3.64 (m, 2H); 3.62-3.52 (m, 2H); 2.52-2.40 (m, 4H)

Example 48: 3-(Methoxycarbonyl)phenyl 4-(diphenylmethylene)piperidine-1-carboxylate $^1$H NMR (400 MHz, CDCl$_3$) δ 7.54 (t, 1H J=2.0); 7.4-7.32 (m, 1H); 7.30-7.15 (m, 8H); 7.10-7.02 (m, 4H); 3.81 (s, 3H); 3.70-3.56 (m, 4H); 2.50-2.40 (m, 4H)

Example 49: 5-Cyano-2-fluorophenyl 4-benzhydrylpiperidine-1-carboxylate $^1$H NMR (400 MHz, CDCl$_3$) δ 7.53 (dd, 1H, J=7.0 Hz, J=2.0 Hz); 7.49 (ddd, 1H, J=7.0 Hz, J=2.0, J=2.0); 7.35-7.25 (m, 8H); 7.25-7.22 (m, 1H); 7.22-7.15 (m, 2H); 4.22 (d, 1H, J=13.0 Hz); 4.17 (d, 1H, J=13.0 Hz); 3.54 (d, 1H, J=7.0); 3.0 (t, 1H, J=13.0 Hz); 2.86 (t, 1H, J=13.0 Hz); 2.40-2.30 (m, 1H); 1.67 (d, 2H, J=13.0); 1.25 (dq, 2H, J=13.0, J=2.0)

Example 50: 3-Cyano-5-hydroxyphenyl 4-benzhydrylpiperidine-1-carboxylate $^1$H NMR (400 MHz, CDCl$_3$) δ 7.35-7.27 (m, 8H); 7.22-7.15 (m, 2H); 6.89 (s, 1H); 6.89 (s, 1H); 6.79 (s, 1H); 4.19 (d, 2H J=13.0); 3.56 (d, 1H J=7.0); 3.05-2.75 (m, 2H); 2.37-2.31 (m, 2H); 1.67 (d, 2H, J=13.0); 1.30 (dq, 2H, J=13.0, J=2.0)

Example 51: 6-Chloropyridin-2-yl 4-(hydroxydiphenylmethyl)piperidine-1-carboxylate $^1$H NMR (400 MHz, CDCl$_3$) δ 7.70 (t, 1H, J=8.0 Hz); 7.47 (d, 4H, J=8.0 Hz); 7.32 (d, 4H, J=8.0 Hz); 7.24-7.22 (m, 1H, (4H, overlapping with t at δ 7.21 2H, J=8.0 Hz); 4.30 (t, 2H, J=13.0 Hz); 3.05 (t, 1H, J=13.0 Hz); 2.88 (t, 1H, J=13.0 Hz); 1H); 1.67 (d, 1H, J=13.0 Hz); 1.45 (dq, 2H, J=13.0 Hz, J=2.0 Hz)

Example 52: 3-Cyanophenyl 4-benzylpiperidine-1-carboxylate $^1$H NMR (400 MHz, CDCl$_3$) δ 7.49-7.42 (m, 3H); 7.37 (td, 1H, J=7.0 Hz, J=2.0 Hz); 7.31 (t, 2H, J=7.0 Hz); 7.22 (d, 1H, J=8.0 Hz); 7.16 (d, 1H, J=8.0 Hz); 4.23 (t, 2H, J=12.0 Hz); 2.94 (t, 1H, J=12.0 Hz); 2.81 (t, 1H, J=12.0 Hz); 2.60 (d, 2H, J=6.8 Hz); 1.74 (d, 2H, J=12.0 Hz); 1.27 (dq, 2H, J=12.0 Hz, J=4.0 Hz)

Example 54 6-Chloropyridin-2-yl 4-(benzhydryl)piperidine-1-carboxylate $^1$H NMR (400 MHz, CDCl$_3$) δ 7.70 (t, 1H, J=8.0 Hz); 7.35-7.25 (m, 9H); 7.25-7.15 (m, 3H); 7.05 (d, 1H, J=8.0 Hz); 4.20 (t, 2H, J=13.0 Hz); 3.55 (d, 1H, J=6.0 Hz); 3.0 (t, 1H, J=13.0 Hz); 2.85 (t, 1H, J=13.0 Hz); 2.4-2.2 (m, 1H), 1.7-1.55 (m, 2H); 1.25 (dq, 2H, J=13.0 Hz, J=2.0 Hz)

Example 55: 3-(Methoxycarbonyl)phenyl 4-(benzhydryloxy)piperidine-1-carboxylate $^1$H NMR (400 MHz, CDCl$_3$) 7.62 (d, 2H, J=8.0 Hz); 7.55-7.42 (m, 2H); 7.40-7.28 (m, 8H); 7.02 (d, 2H, J=8.0 Hz); 5.55 (s, 1H); 3.94 (s, 3H); 3.90-3.76 (m, 3H); 3.7-3.35 (m, 2H); 1.92-1.85 (m, 4H)

Example 56: 5-Cyano-2-fluorophenyl 4-(benzhydryloxy)piperidine-1-carboxylate $^1$H NMR (400 MHz, CDCl$_3$) δ 7.55 (dd, 1H, J=7.0 Hz, J=2.0 Hz); 7.51-7.49 (m, 1H); 7.38-7.30 (m, 8H) 7.27 (t, 2H, J=7.0 Hz); 7.18-7.15 (m, 1H); 5.54 (s, 1H), 3.95-3.85 (m, 1H); 3.82-3.75 (m, 1H); 3.74-3.68 (m, 1H); 3.60-3.50 (m, 1H); 3.49-3.39 (m, 1H); 1.92-1.84 (m, 2H); 1.83-1.80 (m, 2H)

Example 57: 6-Chloropyridin-2-yl 4-(benzhydryloxy)piperidine-1-carboxylate $^1$H NMR (400 MHz, CDCl$_3$) δ 7.71 (t, 1H, J=8.0 Hz); 7.36-7.31 (m, 7H); 7.28-7.24 (m, 3H); 7.21 (d, 1H, J=8.0 Hz); 7.07 (d, 1H, J=8.0 Hz); 5.53 (s, 1H); 3.95-3.87 (m, 1H); 3.86-3.76 (m, 1H); 3.75-3.65 (m, 1H); 3.58-3.48 (m, 1H); 3.47-3.37 (m, 1H); 1.90-1.82 (m, 2H); 1.81-1.72 (m, 2H)

Example 58: 3-Cyanophenyl 4-(benzhydryloxy)piperidine-1-carboxylate $^1$H NMR (400 MHz, CDCl$_3$) δ 7.49-7.46 (m, 1H); 7.45-7.41 (m, 2H); 7.39-7.33 (m, 8H); 7.32-7.27 (m, 3H); 5.60 (s, 1H); 3.95-3.75 (m, 2H); 3.74-3.68 (m, 1H); 3.55-3.40 (m, 2H); 1.93-1.87 (m, 2H); 1.84-1.74 (m, 2H) Method E: Synthesis of 4-arylsulfonylpiperidine carbamates 29 and 4-arylsulfonylpiperazine carbamates 32

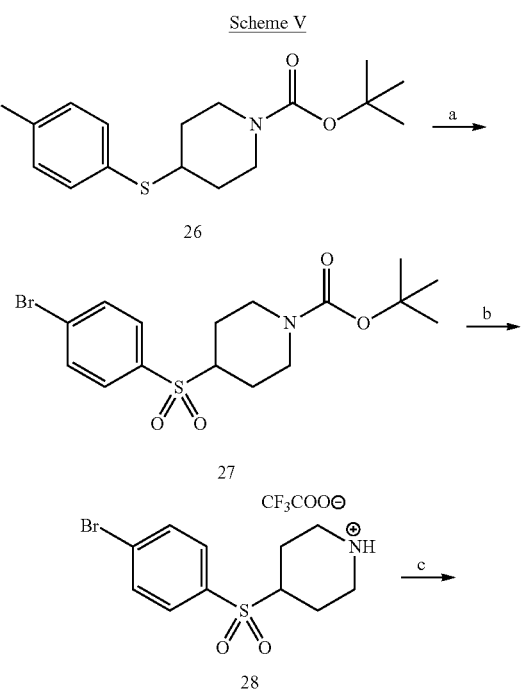

Scheme V

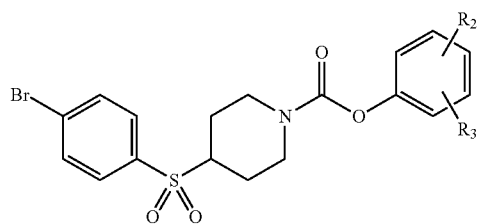

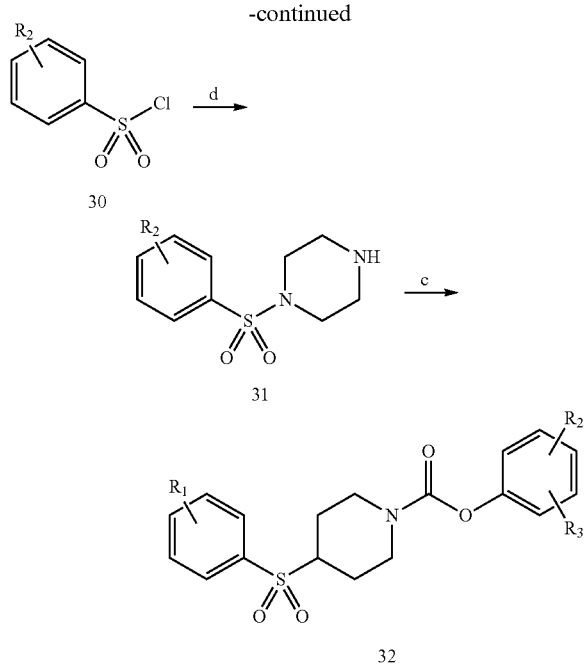

30

31

32

Reagent: (a) mCPBA, CH₂Cl₂, rt 10 hours, (b) TFA, CH₂Cl₂, rt, 12 hours; (c) 16, Et₃N, rt 3-6 h; (d) piperazine, CH₂Cl₂ rt 2 hours.

Synthesis started from tert-butyl (4-4-Bromophenyl)thio-piperidine-1-carboxylate (26), which was prepared as per literature procedure (Fletcher et al. *J. Med. Chem.* (2002) 45: 492-503). Piperidinethioether 26 was oxidized to sulfone 27 with m-CPBA and the N—BOC group was deprotected with TFA, to give piperidinium TFA salt 28, which was treated with aryl chloroformates 16, to give sulfonyl piperidine carbamates 29. Commercially available aryl sulfonyl chlorides 30 were treated with piperazine to give corresponding 1-(arylsulfonyl)piperazine derivatives 33, which were converted in to carbamate derivatives 32, by treating with aryl chloroformates 16, as shown in scheme V.

The Following Examples were Prepared by Following Method E

Synthesis of Example 59, 3-Cyanophenyl 4-(4-bromophenylsulfonyl)piperidine-1-carboxylate Step a) Synthesis of tert-butyl 4-((4-bromophenyl)sulfonyl)piperidine-1-carboxylate (27)

To a solution of name (2.1 g, 5.6 mmol) in dichloromethane (50 mL) at 0° C. was added of m-CPBA (2.1 g, 12.4 mmol) and the solution was stirred at room temperature overnight hours. The solution was diluted with water and washed with 10 percent aqueous Na₂SO₃ solution and saturated aqueousNaHCO₃ solution, sequentially. The organic layer was dried over magnesium sulfate and the solvent removed under reduced pressure to afford 2.1 g of tert-butyl 4-((4-bromophenyl)sulfonyl)piperidine-1-carboxylate as a white solid.

$^1$H NMR (400 MHz, CDCl₃) δ 7.71 (s, 4H); 4.35-4.25 (m, 2H); 3.10-2.90 (m, 1H); 2.70-2.55 (m, 2H); 1.96 (d, 2H, J=8.0 Hz); 1.58 (d, 2H, J=12.0 Hz); 1.43 (s, 9H)

Step b) Synthesis of 4-((4-bromophenyl)sulfonyl)piperidinium trifluoro acetate (28)

A solution of tort-butyl 4-((4-bromophenyl)sulfonyl)piperidine-1-carboxylate (2.0 g, 4.96 mmol) and TFA (1.9 mL, 24.8 mmol) in CH₂Cl₂ (20 mL) at rt. was stirred overnight and then concentrated. The residue was triturated with 10% EtOAc:Hexane. The precipitating salt was isolated by filtration and dried to give 1.9 g of 4-((4-bromophenyl)sulfonyl)piperidinium trifluoro acetate as a white solid.

$^1$H NMR (400 MHz, DMSO) δ 8.60 (brs, 1H); 8.33 (brs, 1H); 7.82 (d, 2H, J=8 Hz); 7.78 (d, 2H, J=8 Hz); 3.46 (d, 2H, J=8.0 Hz); 2.97 (t, 1H, J=12.0 Hz); 2.16 9 (d, 2H, J=12.0 Hz); 1.90 (d, 2H, J=8.0 Hz)

Step c) 3-Cyanophenyl 4-(4-bromophenylsulfonyl)piperidine-1-carboxylate

To a stirred solution of the of 3-cyanophenyl chloroformate (Scheme III, 0.10 g, 0.55 mmol) in methylene chloride at room temperature under argon atmosphere were added 4-((4-bromophenyl)sulfonyl)piperidinium trifluoro acetate (0.27 g, 0.66 mmol) and triethyl amine (0.18 g, 1.32 mmol), sequentially. The resulting mixture was stirred at room temperature for 2 h. After the completion of reaction, as monitored by TLC, mixture was diluted with water, the aqueous layer was extracted with methylene chloride, the combined organic layer was dried over MgSO₄, and the solvent removed under reduced pressure to give a crude material, purified by column chromatography on silica gel to give 3-cyanophenyl 4-(4-bromophenylsulfonyl)piperidine-1-carboxylate as a white solid.

$^1$H NMR (400 MHz, CDCl₃) δ 7.72 (s, 4H); 7.55-7.45 (m, 2H); 7.43-7.40 (m, 1H); 7.35 (d, 1H, J=8.0 Hz); 4.5-4.30 (m, 4H); 3.20-3.12 (m, 1H); 3.10-3.0 (m, 1H); 2.92-2.80 (m, 2H); 2.20-2.05 (m, 2H); 1.90-1.70 (m, 2H)

Step d) Synthesis of 4-tolylsulfonylpiperazine (31, R₂=Me)

To a stirred solution of p-tolylsulfonyl chloride 31 (1.90 g, 10.0 mmol) in methylene chloride (50 mL) at 0° C. was added piperazine (0.95 g, 11.0 mmol) and triethyl amine (1.1 g, 11.0 mmol). The mixture was stirred at 0° C. for 10 min and at room temperature under argon atmosphere for 2 h. After the completion of reaction, as monitored by TLC, mixture was diluted with water. The aqueous layer was extracted with methylene chloride, and the combined organic layer was dried over MgSO₄. The solvent removed under reduced pressure to give 2.1 g of 4-tolylsulfonylpiperazine as a white solid, used in next step without further purification.

$^1$H NMR (400 MHz, CDCl₃) δ 7.65 (d, 2H, J=8.0 Hz); 7.43 (d, 2H, J=8.0 Hz); 3.07 (m, 4H); 2.60-2.51 (m, 4H); 2.45 (s, 3H)

Examples 60-66 were Synthesized by Method E

Example 60: 5-Cyano-2-fluorophenyl 4-(4-bromophenylsulfonyl)piperidine-1-carboxylate $^1$H NMR (400 MHz, CDCl₃) δ 7.76 (s, 4H); 7.60-7.50 (m, 1H); 7.30-7.20 (m, 2H); 4.5-4.30 (m, 4H); 3.20-3.12 (m, 1H); 3.10-3.0 (m, 1H); 2.92-2.80 (m, 2H); 2.20-2.05 (m, 2H); 1.90-1.70 (m, 2H)

Example 61: 5-Cyano-2-methylphenyl 4-(4-bromophenylsulfonyl)piperidine-1-carboxylate $^1$H NMR (400 MHz, CDCl₃) δ 7.76 (s, 4H); 7.41 (dd, 1H, J=8.0 Hz, J=2.0 Hz); 7.35 (d, 1H, J=2.0 Hz); 7.30 (d, 1H, J=8.0 Hz); 4.43 (d, 1H, J=12.0 Hz); 4.37 (d, 1H, J=12.0 Hz);

3.13 (tt, 1H, J=12.0 Hz, J=4.0 Hz); 3.08 (t, 1H, J=12.0 Hz); 2.87 (t, 1H, J=12.0 Hz); 2.23 (s, 3H); 2.20-2.0 (m, 2H); 1.85-1.68 (m, 2H)

Example 62: 5-Cyano-2-methoxyphenyl 4-(4-bromophenylsulfonyl)piperidine-1-carboxylate ¹H NMR (400 MHz, CDCl₃) δ 7.76 (s, 4H); 7.51 (dd, 1H, J=8.0 Hz, J=2.0 Hz); 7.35 (d, 1H, J=2.0 Hz); 6.98 (d, 1H, J=8.0 Hz); 4.42 (d, 1H, J=12.0 Hz); 4.33 (d, 1H, J=12.0 Hz); 3.88 (s, 3H); 3.11 (tt, 1H, J=12.0 Hz, J=4.0 Hz); 2.99 (t, 1H, J=12.0 Hz); 2.82 (t, 1H, J=12.0 Hz); 2.12-1.95 (m, 2H); 1.90-1.70 (m, 2H)

Example 63: 2,6-Difluorophenyl 4-(4-bromophenylsulfonyl)piperidine-1-carboxylate ¹H NMR (400 MHz, CDCl₃) δ 7.76 (s, 4H); 7.42 (m, 2H); 7.27 (t, 1H, J=8.0 Hz); 4.43 (d, 1H, J=12.0 Hz); 4.32 (d, 1H, J=12.0 Hz); 3.89 (s, 3H); 3.10 (tt, 1H, J=12.0 Hz, J=4.0 Hz); 2.99 (t, 1H, J=12.0 Hz); 2.81 (t, 1H, J=12.0 Hz); 2.10-1.92 (m, 2H); 1.91-1.72 (m, 2H)

Example 64: 4-Bromophenyl 4-tosylpiperazine-1-carboxylate

¹H NMR (400 MHz, CDCl₃) δ 7.65 (d, 2H, J=8.0 Hz); 7.43 (d, 2H, J=8.0 Hz); 7.36 (d, 2H, J=8.0 Hz); 6.92 (d, 2H J=8.0); 3.78-3.72 (m, 2H); 3.72-3.62 (m, 2H); 3.07 (t, 4H, J=4.0 Hz); 2.45 (s, 3H)

Example 65: 2,6-Difluorophenyl 4-tosylpiperazine-1-carboxylate

¹H NMR (400 MHz, CDCl₃) δ 7.6 (d, 2H, J=8.0 Hz); 7.33 (d, 2H, J=8.0 Hz); 7.19-7.09 (m, 1H); 6.93 (t, 2H, J=8.0 Hz); 3.90-3.80 (m, 2H); 3.7-0-3.60 (m, 2H); 3.05-3.15 (t, 4H, J=4.0 Hz); 2.46 (s, 3H)

Example 66: 4'-Fluoro-3-hydroxy-[1,1'-biphenyl]-4-yl 4-tosylpiperazine-1-carboxylate ¹H NMR (400 MHz, CDCl₃) δ 7.67 (d, 2H, J=8.0 Hz); 7.60 (d, 1H, J=8.0 Hz); 7.50-7.40 (m, 2H); 7.39-7.22 (m, 3H); 7.15 (t, 1H, J=2.0 Hz); 7.08 (dt, 2H, J=8.0 Hz, J=2.0 Hz); 6.70 (brs, 1H); 3.88-3.78 (m, 2H); 3.75-0-3.68 (m, 2H); 3.15-3.05 (m, 4H); 2.47 (s, 3H)

Method F: Synthesis of N-(3-(1,1-dioxidothiomorpholino)phenyl)-4-phenylpiperazine/piperidine ureas 38

Commercially available 3-nitro bromobenzene 33 (Scheme VII) was coupled with thiomorpholine under Buchwald condition reference to give 4-(3-nitrophenyl)thiomorpholine 34. Sulfide was oxidized to sulfones 35, followed by catalytic reduction of the nitro group to give amine 36, which was converted into its phenyl carbamate 37, by reacting with phenyl chloroformate. Finally, N-aryl ureas 38 were obtained by reacting common intermediate phenyl carbamate 37 with aryl piperazine 3/ commercially available phenyl piperidine under microwave irradiation condition Scheme VI

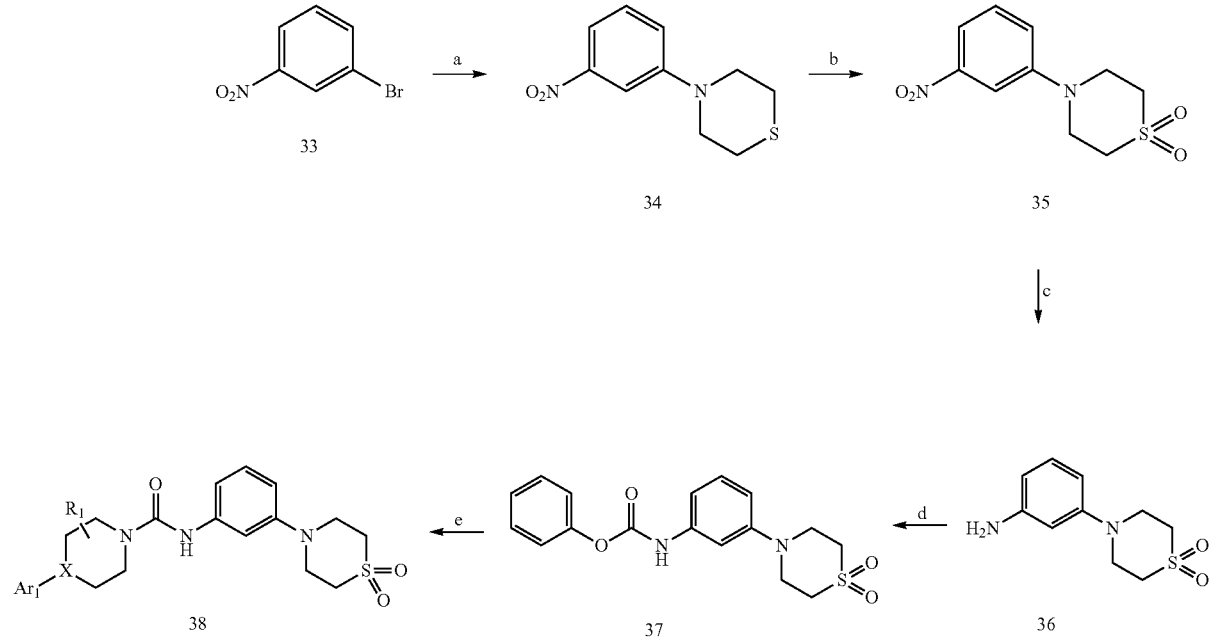

Reagents (a) Thiomorpholine, Pd₂(dba)₃, Xantphos, K₂CO₃, 1,4-dioxane, reflux, 10 h; (b) m-CPBA, DCM, rt, overnight; (c) H₂, Pd—C; (d) Phenyl chloroformate, Et₃N, DCM; (e) Aryl piperazines, piperadines, microwave, 100° C., 10 min.

The Following Examples were Prepared by Following Method F

Synthesis of Example 67, N-(3-(1,1-Dioxidothiomorpholino)phenyl)-4-phenylpiperazine-1-carboxamide Step a) Synthesis of 4-(3-nitro-phenyl)-thiomorpholine 34

$Pd_2(dba)_3$ (0.362 g, 0.3 mmol), xantphos (0.343 g, 0.5 $K_2CO_3$ (1.91 g, 13.8 mol) were added to a flask containing dioxane the mixture was flushed with nitrogen gas for 10 min, followed by the addition of 1-bromo-3-nitro-benzene (2.0 g, 9.8 mmol) and thiomorpholine (1.2 g, 1.8 mmol) and the flask was refluxed overnight. The reaction was monitored by the TLC (20% EtOAc:hexane). The reaction mixture was then filtered through celite, and the filterate was concentrated. The crude product was purified by column chromatography (10% ethyl acetate in hexane) to afford 1.8 g of 4-(3-nitro-phenyl)-thiomorpholine as colorless liquid.

$^1$H NMR (500 M Hz, $CDCl_3$) δ 7.87 (s, 1H); 7.82 (d, 1H, J=8 Hz); 7.48 (t, 1H, J=8.5 Hz); 7.37-7.34 (m, 1H); 3.81 (t, 2H, J=5.5 Hz); 3.65 (t, 2H, J=6.0 Hz); 3.57 (t, 2H, J=5.5 Hz); 3.50 (t, 2H, J=5.5 Hz)

Step b) Synthesis of 4-(3-nitro-phenyl)-thiomorpholine 1,1-dioxide 35

To a stirred solution of 4-(3-nitro-phenyl)thiomorpholine 34 (1.8 g, 8.0 mmol) in DCM (25 mL) maintained at 10-15° C. was added mCPBA (3.2 g, 20.0 mmol) The mixture was stirred at 10-15° C. for 30 min and at room temperature overnight, After completion of reaction (monitored by the TLC, 5% methanol:chloroform), the reaction mixture was washed with saturated $NaHCO_3$. The aqueous layer was extracted with ethyl acetate, the combined organic layer was washed with brine solution, dried over $Na_2SO_4$, and concentrated to get the crude product which was purified by column chromatography to afford 1.5 g of 4-(3-Nitro-phenyl)-thiomorpholine 1,1-dioxide as pale yellow solid.

$^1$H NMR (500 M Hz, $CDCl_3$) δ 7.93 (s, 1H); 7.91 (d, 1H, J=8 Hz); 7.50 (t, 1H, J=8.5 Hz); 7.37-7.35 (m, 1H); 4.29 (t, 2H, J=5.5 Hz); 3.75 (t, 2H, J=6.0 Hz); 3.57 (t, 2H, J=5.5 Hz); 3.50 (t, 2H, J=5.5 Hz)

Step c) Synthesis of 3-(1,1-dioxothiomorpholin-4-yl)-phenylamine 36

To a solution of 4-(3-nitro-phenyl)-thiomorpholine 1, 1-dioxide (1.5 g, 0.0058 mol) in MeOH (20 mL) in an atmosphere of argon gas was added 10% Pd—C (200 mg) and the reaction was carried out under $H_2$ gas pressure number?. The reaction was monitored by the TLC. The reaction mixture was filtered through celite and concentered to afford 1.0 g of 3-(1,1-dioxothiomorpholin-4-yl)-phenylamine as a white solid.

$^1$H NMR (500 M Hz, Acetone $d_6$) δ 6.81 (t, 1H, J=8 Hz); 6.01-5.95 (m, 3H); 4.80 (t, 1H, J=5 Hz); 4.38 (bs, 2H); 4.00 (t, 2H, J=5 Hz); 3.59 (q, 2H, J=7.0 Hz); 3.37 (t, 2H, J=7.0 Hz); 3.27 (t, 2H, J=7.0 Hz)

Step d) Synthesis of phenyl (3-(1,1-dioxidothiomorpholino)phenyl)carbamate 37

To solution of 3-(1,1-dioxo-1λ6-thiomorpholin-4-yl)-phenylamine in dry THF (30 mL) at 0° C., was added phenyl chloroformate (1.0 g, 0.8 mL) drop wise over 15 min period. The reaction mixture was allowed to warm to room temperature. After 12 h, the mixture was diluted with EtOAc (100 mL) and washed with saturated aqueous $NaHCO_3$ (20 mL). The organic layer was dried over $MgSO_4$ and concentrated. The residue was chromatographed to give 1.24 g of phenyl (3'-carbamoyl-[1,1'-biphenyl]-3-yl)carbamates as a white solid.

$^1$H NMR (500 M Hz, $CDCl_3$) δ 7.49 (t, 1H, J=8.0 Hz); 7.31-7.28 (m, 3H); 7.11 (t, 2H, J=7.5 Hz); 6.90-6.81 (m, 3H); 3.89 (t, 2H, J=5.0 Hz); 3.10 (t, 2H, J=5.0 Hz)

Step e) Synthesis of N-(3-(1,1-dioxidothiomorpholino)phenyl)-4-phenylpiperazine-1-carboxamide (38, $Ar_1$=Ph, X=N, $R_1$=H)

A solution of phenyl piperazine (0.6 g, 3.69 mmol) and phenyl (3-(1,1-dioxidothiomorpholino)phenyl) carbamate (1.28 g, 3.69 mmol) in acetonitrile was heated in a sealed tube tinder microwave irradiation at 120° C. for 10 min with stirring. The reaction mixture was cooled to room temperature and solvent was removed under reduced pressure. The crude material was partitioned between dichloromethane and water. The aqueous phase was extracted with dichloromethane. The combined extracts were dried over $MgSO_4$ and concentrated. Chromatography of the residue gave 1.28 g of N-(3-(1,1-dioxidothiomorpholino)phenyl)-4-phenylpiperazine-1-carboxamide as white solid.

$^1$H NMR (500 M Hz, $CDCl_3$) δ 7.31 (t, 2H, J=8 Hz); 7.25-7.19 (m, 3H); 7.06 (t, 1H, J=8 Hz); 6.98 (bs, 1H); 6.68 (bs, 1H), 6.48 (d, 1H, J=7.5 Hz); 4.24 (t, 4H, J=5.0 Hz); 3.65 (t, 4H, J=5 Hz); 3.37 (t, 2H, J=5 Hz); 3.17 (t, 2H, J=5 Hz); 2.96 (t, 2H, J=8 Hz); 2.70 (t, 2H, J=8 Hz)

Example 68 was Prepared by Method F

Example 68 N-(3-(1,1-dioxidothiomorpholino)phenyl)-4-phenylpiperidine-1-carboxamide $^1$H NMR (500 M Hz, $CDCl_3$) δ 7.31 (t, 2H, J=8 Hz); 7.25-7.19 (m, 3H); 7.06 (t, 1H, J=8 Hz); 6.98 (bs, 1H); 6.68 (bs, 1H), 6.48 (d, 1H, J=7.5 Hz); 4.20 (d, 3H, J=13.5 Hz); 4.0 (t, 3H, J=5 Hz); 3.65 (t, 2H, J=5 Hz); 3.37 (t, 2H, J=5 Hz); 3.17 (t, 2H, J=5 Hz); 2.96 (t, 2H, J=8 Hz); 2.70 (tt, 1H, J=12 Hz); 1.91 (d, 2H, J=12 Hz); 1.74-1.65 (qd, 2H, J=12.5 Hz, J=4.0 Hz)

Method G: Synthesis of 1,1-dioxidothiomorpholin-1-ylphenyl carbamates 42

3-Amino phenol (Scheme VII) was reacted with divinyl sulfone under bis-aza micheal condition (Halimehjnai et al (*Synthetic Communications*, (2013) 43 191-197) to afford 4-(3-hydroxyphenyl) thiomorpholine 1,1-dioxide 40, which was converted into its chloroformate 41 with phosgene solution in toluene. Chloroformate 41 was converted to aryl carbamates by reaction with aryl piperazine 3 (Scheme I) or commercially available aryl piperidine derivatives.

Scheme VII

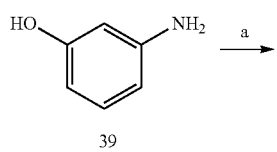

39

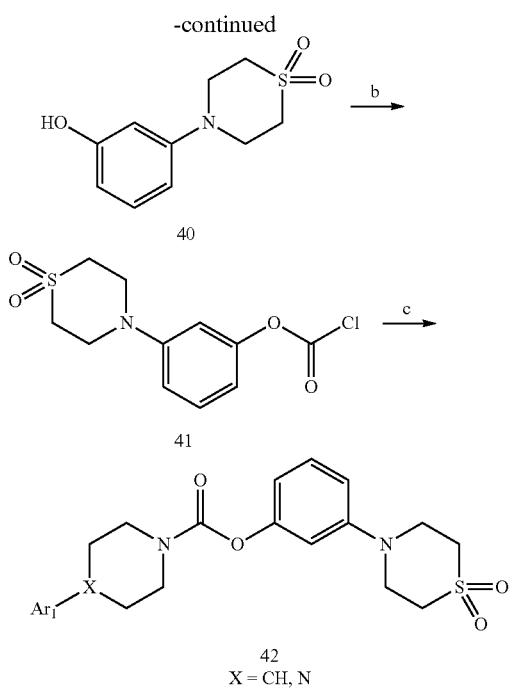

42
X = CH, N

Reagents: (a) divinyl sulfone, boric acid, glycerol (cat.), water, reflux, 3 h; (b) Phosgene, pyridine, DCM, 0° C.-r.t.; (C) aryl piperidine, aryl piperazine, acetonitrile, microwave, 100° C., 10 min.

The Following Examples were Prepared by Following Method G

Synthesis of Example 69:
3-(1,1-Dioxidothiomorpholino)phenyl 4-phenylpiperazine-1-carboxylate Step a) Synthesis of 4-(3-hydroxyphenyl)thiomorpholine 1,1-dioxide 40

Water (30 mL), boric acid (30 mol %), and glycerol (6 drops) were added to a stirred solution of 3-amino phenol 39 (3.2 g, 29.32 mmol) and divinyl sulfone (3.46 g, 29.32 mmol). The resulting mixture was stirred under reflux for 3 h. The reaction mixture was extracted with ethyl acetate, and the organic layer was washed three times with water. After the solvent was evaporated, the crude product was washed with hot petroleum ether, to give 4-(3-hydroxyphenyl)thiomorpholine 1,1-dioxide 6.21 g, as white solid.
$^1$H NMR (500 M Hz, CDCl$_3$) δ 7.26 (t, 1H, J=8.0 Hz); 6.48 (dd, 1H, J=8.0 Hz, J=2.5 Hz); 6.40-6.37 (m, 3H); 5.15 (bs, 1H); 3.85 (t, 2H, J=5.0 Hz); 3.08 (t, 2H, J=5.0 Hz)

Step b) Synthesis of 3-(1,1-dioxidothiomorpholino)phenyl chloroformate 41

To a stirred solution of triphosgene (0.52 g, 1.54 mmol) in dichloromethane at 0° C. under argon atmosphere was added a mixture of the 4-(3-hydroxyphenyl)thiomorpholine 1,1-dioxide (1.0 g, 4.39 mmol) and N,N-diisopropylethyl amine (1.3 mL) in methylene chloride drop wise. After addition was complete the reaction mixture was gradually warmed to room temperature and stirred for h. After the completion of the reaction, as monitored by TLC, the mixture was diluted with ice-cold water, the aqueous layer was extracted with methylene chloride. The combined organic layer was dried over MgSO$_4$, and the solvent was removed under reduced pressure to give 3-(1,1-dioxidothiomorpholino)phenyl chloroformate 1.12 g, white solid, which was used in the next step without any further purification, as.
$^1$H NMR (500 M Hz, CDCl$_3$) δ 7.33 (t, 1H, J=8.0 Hz); 6.85-6.81 (m, 3H); 3.87 (t, 4H, J=5.0 Hz); 3.10 (t, 4H, J=5.0 Hz)

Step c) Synthesis of 3-(1,1-dioxidothiomorpholino)phenyl 4-phenylpiperazine-1-carboxylate (42, Ar$_1$=Ph, X=N)

To a stirred solution of the 3-(1,1-dioxidothiomorpholino) phenyl chloroformate (1.3 g, 4.49 mmol) in methylene chloride (10 mL) at room temperature under argon atmosphere was added 4-phenylpiperazine (0.74 g, 4.48 mmol) and triethylamine (1.1 mL, 4.92 mmol) in methylene chloride. The resulting mixture was stirred at room temperature for 2 h. After the completion of reaction, as monitored by TLC, mixture was diluted with water, the aqueous layer was extracted with methylene chloride, the combined organic layer was dried over MgSO$_4$. The solvent was removed under reduced pressure to give crude material, which were purified by column chromatography on silica gel to give 1.08 g of 3-(1,1-dioxidothiomorpholino)phenyl 4-phenylpiperazine-1-carboxylate as white solid.
$^1$H NMR (500 M Hz, CDCl$_3$) δ 7.33 (t, 2H, J=5.0 Hz); 7.29 (d, 1H, J=7.5.0 Hz); 6.97 (d, 2H, J=7.5 Hz); 6.93 (t, 1H, J=7.5 Hz); 6.75 (dd, 1H, J=7.5 Hz, J=2.0 Hz); 6.72-6.68 (m, 2H), 3.86 (m as t, 4H, J=5.5 Hz); 3.84-3.78 (m, 2H); 3.76-3.70 (m, 2H) 3.24 (m as t, 4H, J=5.5 Hz), 3.01 (m as t, 4H, J=5.0 Hz)

Examples 70-73 were Prepared by Method F

Example 70:
3-(1,1-Dioxothiomorpholin-4-yl)phenyl 4-phenylpiperidine-1-carboxylate $^1$H NMR (500 MHz, CDCl$_3$) δ 7.34 (t, 2H, J=8.0 Hz); 7.28 (t, 2H, J=8.5 Hz); 7.24 (d, 2H, J=8.0 Hz); 6.74 (dd, 1H, J=8.0 Hz, J=2.0 Hz); 6.72-6.68 (m, 2H), 4.42 (t, 2H, J=13.0 Hz); 3.86 (m as t, 4H, J=5.0 Hz); 3.10 (m as t, 4H, J=5.0 Hz), 3.08 (t, 1H, J=6.8 Hz), 2.95 (t, 1H, J=6.8 Hz); 2.75 (tt, 1H, J=12.0 Hz, J=3.5 Hz); 1.94 (d, 2H, J=13.0 Hz); 2.75 (qd, 1H, J=13.0 Hz, J=4.0 Hz)

Example 71: 3-(1,1-Dioxidothiomorpholino)phenyl 4-(3-phenoxybenzyl)piperazine-1-carboxylate $^1$H NMR (500 MHz, CDCl$_3$) δ 7.54 (t, 2H, J=8.0 Hz); 7.32 (t, 2H, J=8.5 Hz); 7.24-6.90 (m, 4H); 6.74 (dd, 1H, J=8.0 Hz, J=2.0 Hz); 6.65-6.61 (m, 2H), 4.42 (t, 2H, J=13.0 Hz); 3.86 (m as t, 4H, J=5.0 Hz); 3.10 (m as t, 4H, J=5.0 Hz), 3.08 (t, 1H, J=6.8 Hz), 2.95 (t, 1H, J=6.8 Hz); 2.75 (tt, 1H, J=12.0 Hz, J=3.5 Hz); 1.94 (d, 2H, J=13.0 Hz); 2.75 (qd, 1H, J=13.0 Hz, J=4.0 Hz)

Example 72: 3-(1,1-Dioxidothiomorpholino)phenyl 4-(quinolin-2-ylmethyl)piperazine-1-carboxylate $^1$H NMR (500 MHz, CDCl$_3$) δ 7.44 (t, 2H, J=8.0 Hz); 7.28 (t, 2H, J=8.5 Hz); 7.24 (d, 2H, J=8.0 Hz); 6.74 (dd, 1H, J=8.0 Hz, J=2.0 Hz); 6.72-6.68 (m, 2H), 4.42 (t, 2H, J=13.0

Hz); 3.86 (m, 4H); 3.10 (m as t, 4H, J=5.0 Hz), 3.08 (t, 1H, J=6.8 Hz), 2.95 (t, 1H, J=6.8 Hz); 2.75 (tt, 1H, J=12.0 Hz, J=3.5 Hz); 1.94 (d, 2H, J=13.0 Hz); 2.73 (qd, 2H, J=13.0 Hz, J=4.0 Hz)

Example 73: 3-(1,1-Dioxidothiomorpholino)phenyl 2-methyl-4-phenylpiperazine-1-carboxylate $^1$H NMR (500 MHz, CDCl$_3$) δ 7.34 (t, 2H, J=8.0 Hz); 7.26 (t, 2H, J=8.5 Hz); 7.24 (d, 2H, J=8.0 Hz); 6.74 (dd, 1H, J=8.0 Hz, J=2.0 Hz); 6.70-6.48 (m, 2H), 4.42 (t, 2H, J=13.0 Hz); 3.86 (m as t, 4H, J=5.0 Hz); 3.10 (m as t, 4H, J=5.0 Hz), 3.08 (t, 1H, J=6.8 Hz), 2.95 (t, 1H, J=6.8 Hz); 2.75 (tt, 1H, J=12.0 Hz, J=3.5 Hz); 1.94 (d, 2H, J=13.0 Hz); 1.56 (d, 2H, J=8 Hz)

Method H Syntheses of Azetidine Carbamates 40

As depicted in Scheme VIII, syntheses of azetidine carbamates 40 involve coupling chloroformates 16 (Scheme III) with azetidine derivatives 39. Substituted azetidine derivatives 39 were obtained in two steps from commercially available 1-benzhydrylazetidin-3-01 (37). This process involves displacement of 4-chlorobenzyl bromide with 37 to produce benzylazetidine ether 38 followed by removal of benzhydryl protection to give substituted azetidine 39 (Hart et al Biorg. & Med. Chem. Lett. (2009) 19: 4241-4244).

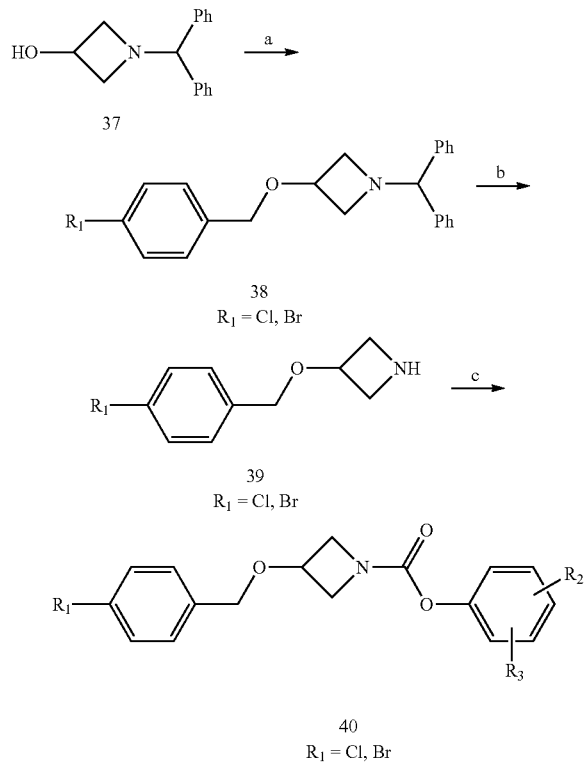

Scheme VIII

Reagents: (a) NaH, THF, 0° C., 10 min, 4-chlorobenzyl bromide, THF, reflux, 6 h; (b) 1-chloroethyl chloroformate CH$_2$Cl$_2$, rt, 1 h, MeOH, rt, 6 h; (c) 16, Et$_3$N, DCM, rt 2 h The following examples were prepared by following Method H Synthesis of Example 74 3-Cyanophenyl 3-(4-chlorobenzyloxy)azetidine-1-carboxylate Step a) Synthesis of 1-Benzhydryl-3-(4-chlorobenzyloxy)azetidine (38, R$_1$=Cl)

A solution of 4-chlorobenzyl bromide (3.1 g, 15.0 mmol) in TI-IF (20 mL) was added to a suspension of 1-benzhydrylazetidin-3-ol sodium salt, which was generated in-situ by treating azetidinol 37 (2.4 g, 10.0 mmol) in dry THF (100 mL) at 0° C. with NaH (60% dispersion in mineral oil, 410 mg, 10.5 mmol). The resulting mixture was refluxed for 6 hours, cooled to room temperature, and diluted with water. The aqueous layer was extracted with EtOAc and the organic layer was washed with brine, dried over MgSO$_4$ and solvent removed in vacuo. The crude product was purified by column chromatography on silica gel to give 2.77 g of 1-Benzhydryl-3-(4-Chlorobenzyloxy) azetidine as viscous liquid.

$^1$H NMR (400 MHz, CDCl$_3$) δ 7.38-7.33 (m, 3H); 7.32-7.20 (m, 11H); 4.36 (s, 2H); 4.2-4.18 (m, 1H); 3.55-3.45 (m, 2H); 3.0-2.90 (m, 2H)

Step b) Synthesis of 3-(4-chlorobenzyloxy)azetidine (39, R$_1$=Cl)

A solution of 1-benzhydryl-3-(4-chlorobenzyloxy)azetidine (38, 2.55 g, 7.0 mmol) in anhydrous dichloromethane (50 mL) was treated with 1-chloroethyl chloroformate (2.70 mL, 24.5 mmol) at room temperature and stirred for 1 h. The mixture was treated with methanol (10 mL) and stirred at the same temperature for additional 6 h. The solvent was removed under reduced pressure and the residue was triturated with 5% ethyl acetate:hexane to give azetidine hydrochloride salt, which was partitioned between dichloromethane and aqueous NaHCO$_3$. The aqueous layer was further extracted with dichloromethane. The combined organic layer was washed with brine, dried over MgSO4 and solvent removed in vacuo to give a 1.26 g of 3-(4-chlorobenzyloxy) azetidine (39) as pale yellow gum.

$^1$H NMR (400 MHz, CDCl$_3$) δ 7.31 (d, 2H, J=8.0 Hz)); δ 7.31 (d, 2H, J=8.0 Hz)); 7.28 (d, 2H, J=8.0 Hz)); 4.35 (s, 2H); 4.22-4.17 (m, 1H); 3.55-3.45 (m, 2H); 3.0-2.90 (m, 2H)

Step b) Synthesis of 3-Cyanophenyl 3-(4-chlorobenzyloxy)azetidine-1-carboxylate

To a stirred solution of 3-cyanophenyl chloroformate 16 (Scheme III, 0.36 g, 2.0 mmol,) in methylene chloride (20 mL) at room temperature under argon atmosphere were added a 3-(4-chlorobenzyloxy)azetidine (39) (Scheme VIII, 0.5 g, 2.50 mmol) and triethylamine (0.35 mL, 2.5 mmol) and the resulting mixture was stirred at room temperature for 2 hours. After the completion of reaction, as monitored by TLC, the mixture was diluted with water, the aqueous layer was extracted with methylene chloride (2×10 mL), and the combined organic layer was dried over MgSO$_4$. The solvent was removed under reduced pressure to give a crude material, which was purified by column chromatography on silica gel to afford 0.45 g of 3-cyanophenyl 3-(4-chlorobenzyloxy) azetidine-1-carboxylate as white solid.

$^1$H NMR (400 MHz, CDCl$_3$) δ: 7.47-7.42 (m, 2H); 7.38 (d, 1H, J=8.0 Hz); 7.36 (d, 2H, J=8.0 Hz); 7.33-7.25 (m, 3); 4.47 (s, 2H); 4.46-4.39 (m, 1H); 4.38-4.18 (m, 2H); 4.17-3.98 (m, 2H)

Examples 75-80 were Synthesized by Method H

Example 75: 3-(Trifluoromethyl)phenyl 3-(4-chlorobenzyloxy)azetidine-1-carboxylate $^1$H NMR (400 MHz, CDCl$_3$) δ: 7.31 (d, 2H, J=8.0 Hz); 7.28-7.22 (m, 4H); 7.17 (t, 1H, J=8.0 Hz); 7.02 (d, 1H, J=8.0 Hz); 4.46 (s, 2H); 4.44-4.34 (m, 1H); 4.32-4.13 (m, 2H); 4.12-3.94 (m, 2H)

Example 76: 3-Bromophenyl 3-(4-chlorobenzyloxy)azetidine-1-carboxylate $^1$H NMR (400 MHz, CDCl$_3$) δ: 7.31 (d, 2H, J=8.0 Hz); 7.28-7.22 (m, 4H); 7.17 (t, 1H, J=8.0 Hz); 7.02 (d, 1H, J=8.0 Hz); 4.46 (s, 2H); 4.44-4.34 (m, 1H); 4.32-4.13 (m, 2H); 4.12-3.94 (m, 2H)

Example 77: 3-Carbamoylphenyl 3-(4-chlorobenzyloxy)azetidine-1-carboxylate $^1$H NMR (400 MHz, CDCl$_3$) δ: 7.62 (d, 1H, J=8.0 Hz); 7.56 (m, 1H); 7.43 (t, 1H, J=8.0 Hz); 7.34 (d, 2H, J=8.0 Hz); 7.28 (d, 2H, J=8); 7.25-7.22 (m, 1H); 6.08 (brs, 1H); 5.06 (brs, 1H); 4.46 (s, 2H); 4.45-4.40 (m, 1H); 4.38-4.18 (m, 2H); 4.15-3.95 (m, 2H)

Example 78: 3-Methoxyphenyl 3-(4-Bromobenzyloxy)azetidine-1-carboxylate $^1$H NMR (400 MHz, CDCl$_3$) δ: 7.51 (d, 1H, J=8.0 Hz); 7.25 (d, 2H, J=8.0 Hz); 7.23 (dt, 2H, J=8.0 Hz, J=2.0 Hz); 6.74 (dd, 1H, J=8.0 Hz, J=2.0 Hz); 6.70 (dd, 1H, J=8.0 Hz, J=2.0 Hz); 6.66 (t, 1H, J=2.0 Hz); 4.48 (s, 2H); 4.47-4.38 (m, 1H); 4.39-4.29 (m, 2H); 4.26-4.04 (m, 2H); 3.78 (s, 3H)

Example 79: 2,4-Dichlorophenyl 3-(4-chlorobenzyloxy)azetidine-1-carboxylate $^1$H NMR (400 MHz, CDCl$_3$) δ: 7.42 (d, 1H, J=2.0 Hz); 7.35 (d, 2H, J=8.0 Hz); 7.28 (d, 2H, J=8.0 Hz); 7.23 (dd, 1H, J=8.0 Hz, J=2.0 Hz); 7.14 (d, 1H, J=8.0 Hz); 4.48 (s, 2H); 4.47-4.36 (m, 2H); 4.28-4.14 (m, 2H); 4.08-3.88 (m, 2H)

Example 80: 3-(Pyridin-3-yl)phenyl 3-(4-chlorobenzyloxy)azetidine-1-carboxylate $^1$H NMR (400 MHz, CDCl$_3$) δ: 8.12 (d, 1H, J=8.0 Hz); 7.68 (d, 1H, J=8.0 Hz); 7.65 (d, 1H, J=8.0 Hz); 7.57-7.51 (m, 2H); 7.50-7.40 (m, 2H); 7.35 (2H, J=8.0 Hz); 7.29 (d, 2H, J=8.0 Hz); 7.22 (1H, J=8.0 Hz); 4.48 (s, 2H); 4.47-4.40 (m, 1H); 4.38-4.20 (m, 2H); 4.20-4.0 (m, 2H)

Method I Syntheses of Azetidine Carboxamides 42

As depicted in Scheme IX, azetidine carboxamides 42 were obtained by coupling commercially available isocyanates 41 with 3-(4-chlorobenzyloxy)azetidine or 3-(4-bromobenzyloxy)azetidine 39 (Scheme VIII).

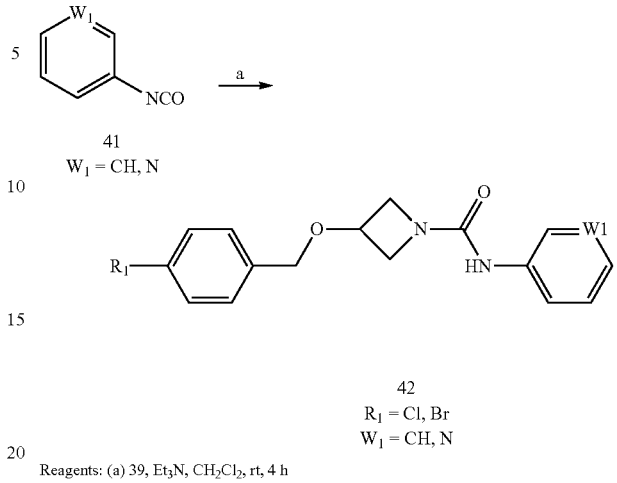

Scheme IX

Reagents: (a) 39, Et$_3$N, CH$_2$Cl$_2$, rt, 4 h

Synthesis of Example 81

3-(4-Chlorobenzyloxy)-N-phenylazetidine-1-carboxamide

Step a)

To a stirred solution of commercially available phenyl isocyanate (60 mg 0.5 mmol) in methylene chloride (20 mL) at room temperature under argon atmosphere were added a 3-(4-chlorobenzyloxy)azetidine (39) (Scheme VIII, 120 mg, 0.60 mmol) and triethylamine (0.08 mL, 2.5 mmol) and the resulting mixture was stirred at room temperature for 4 hours. After the completion of reaction, as monitored by TLC, the mixture was diluted with water, the aqueous layer was extracted with methylene chloride (2×10 mL), and the combined organic layer was dried over MgSO$_4$. The solvent was removed under reduced pressure to give a crude material, which was purified by column chromatography on silica gel to afford 135 mg 3-(4-chlorobenzyloxy)-N-phenylazetidine-1-carboxamide as a white solid.

$^1$H NMR (400 MHz, CDCl$_3$) δ: 7.37 (d, 2H, J=8.0 Hz); 7.34 (d, 2H, J=8.0 Hz); 7.30-7.25 (m, 4H); 7.03 (t, 1H, J=8.0 Hz); 5.94 (brs, 1H); 4.45 (s, 2H); 4.42-4.36 (m, 1); 4.17 (dd, 2H, J=9.2 Hz, J=4.0 Hz); 3.96 (dd, 1H, J=9.2 Hz, J=4.0 Hz)

Example 82 was Synthesized by Method H

Example 82: 3-(4-Bromobenzyloxy)-N-(pyridin-3-yl)azetidine-1-carboxamide $^1$H NMR (400 MHz, CDCl$_3$) δ: 8.60 (t, 2H, J=2.0 Hz); 8.50 (brs, 1H, >NH); 8.08 (d, 1H, J=8.0 Hz); 7.88 (dd, 1H, J=8.0 Hz, J=2.0 Hz); 7.45 (d, 2H, J=7.6 Hz); 7.24 (d, 2H, J=7.6 Hz); 7.13 (dd, 1H, J=8.0 Hz, J=4.0 Hz); 4.40 (s, 2H); 4.39-4.31 (m, 1H); 4.13 (t, 2H, J=9.2 Hz); 3.82 (dd, 1H, J=9.2 Hz, J=4.0 Hz)

Method J Syntheses of Azetidine Methanones 47

As depicted in Scheme X, azetidine methanones 47 were produced by coupling azetidine carbonyl chlorides 46 with commercially available 4-phenyl-1H-imidazole, 1H-1,2,3-triazole or 1H-benzo[d]imidazole. Azetidine carbonyl chlorides 46 were obtained in two steps including displacement of commercially available benzhydrlyazetidine mesylate 43 with commercially available 4-phenylpiperidine or 4-thiophenol, to give 3-aminoazetidine or azetidine thioether 44. Subsequently, deprotection of benzhydryl group gave azetidine derivative 45, which were carbonylated with triphosgene.

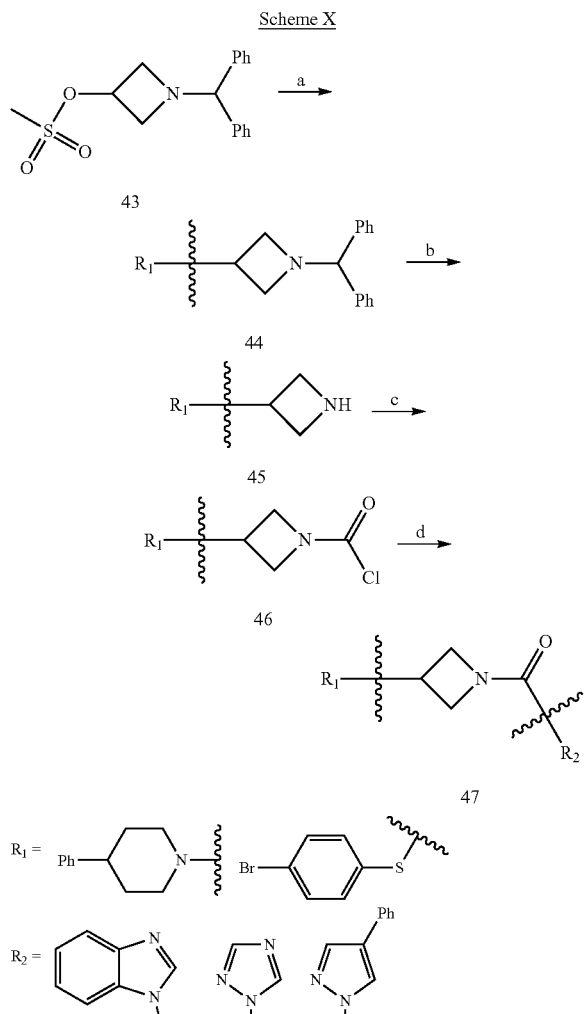

Reagents (a) 4-phenylpiperidine or 4-bromothiophenol, DIEA, CH$_3$CN, 70° C., 4 h; (b) 1-chloroethyl chloroformate CH$_2$Cl$_2$, rt, 1 h, MeOH, rt, 6 h; (c) triphosgene, pyridine, CH$_2$Cl$_2$, 0° C.-rt, 1 h; (d) DIEA 4-phenyl-1H-imidazole, 1H-1,2,3-triazole or 1H-benzo[d]imidazole, rt, THF, 12 h.

The Following Examples were Prepared by Following Method J

Synthesis of Example 83 (1H-Benzo[d]imidazol-1-yl)(3-(4-phenylpiperidin-1-yl)azetidin-1-yl)methanone Step a) Syntheses of 1-(Benzhydrylazetidin-3-yl)-4-phenylpiperidine 44 (R$_1$ is 4-phenylpiperidine)

To a solution of 43 (3.2 g, 10.0 mmol) in acetonitrile (50 mL)) were added 4-phenylpiperidine (1.93 g, 12.0 mmol) and diisopropylethyl amine (2.1 mL, 12.0 mmol), sequentially and the mixture heated at 70° C. for 3 h. Solvent was removed under reduced pressure, and the resulting slurry partitioned between ethyl acetate and water. The organic layer was washed with brine, dried over MgSO$_4$ and evaporated. The crude product was purified by column chromatography on silica gel to give 2.75 g of 1(1-benzhydrylazetidin-3-yl)-4-phenylpiperidine as white solid.

$^1$H NMR (400 MHz, CDCl$_3$) δ: 7.39 (d, 4H, J=9.0 Hz) 7.27 (d, 6H, J=9.0 Hz); 7.21-715 (m, 3H); 7.12 (d, 2H, J=9.0 Hz); 4.4 (s, 1H), 3.35-3.25 (m, 2H); 3.0-2.85 (m, 3H); 2.8-2.7 (m, 3H); 1.80-1.65 (m, 2H); 1.69 (d, 2H, J=13.0 Hz); 1.35-1.25 (m, 2H)

Step b) Synthesis of 1-(azetidin-3-yl)-4-phenylpiperidine 45 (R$_1$ is 4-phenylpiperidine)

A solution of 1-(benzhydrylazetidin-3-yl)-4-phenylpiperidine (1.91 g, 5.0 mmol) in anhydrous dichloromethane (20 mL) was treated with 1-chloroethyl chloroformate (1.91 mL, 17.5 mmol) at room temperature and stirred for 1 h. The mixture was treated with methanol (5 mL) and stirred at the same temperature for additional 6 h. The solvent was removed under reduced pressure and the residue was washed with 5% ethyl acetate:hexane to give a partially purified azetidine hydrochloride salt, which alt was partitioned between dichloromethane and aqueous NaHCO$_3$. The organic layer was washed with brine, dried over MgSO$_4$ and solvent removed in vacuo to give a 0.99 g of 1-(azetidin-3-yl)-4-phenylpiperidine as pale yellow gum $^1$H NMR (400 MHz, CDCl$_3$) δ: 7.31 (d, 2H, J=8.0 Hz); 7.27-7.20 (m, 3H); 3.33-3.23 (m, 2H); 3.10-2.90 (m, 3H); 2.82-2.72 (m, 3H); 2.1 (brs 1H); 1.81-1.64 (m, 2H); 1.69 (d, 2H, J=13.0 Hz); 1.33-1.23 (m, 2H)

Step c) Synthesis of 1-(4-phenylpiperidine-1-yl) azetidin-1-carbonyl chloride 46 (R$_1$ is 4-phenylpiperidine)

To a solution of triphosgene (0.45 g, 1.5 mmol) in dichloromethane (10 mL) at 0 under nitrogen atmosphere was added a solution of 1-(azetidin-3-yl)-4-phenylpiperidine (0.97 g, 4.5 mmol) and pyridine (0.45 mL, 4.5 mmol) in dichloromethane (10 mL) drop-wise over 10 minutes. The mixture was stirred at room temperature for 1 hour and diluted with ice-cold water (10 ml). The organic layer was washed with brine, dried over MgSO$_4$ and solvent removed in vacuo to give a 0.96 g of 1-(4-phenylpiperidine-1-yl) azetidin-1-carbonyl chloride as white solid.

$^1$H NMR (400 MHz, CDCl$_3$) δ: 7.31 (d, 2H, J=8.0 Hz); 7.27-7.20 (m, 3H); 4.25-3.95 (m, 4H); 3.30-3.20 (m, 1H); 3.0-2.85 (m, 2H); 2.60-2.50 9m, 1H); 2.10-2.1.95 (m, 2H); 1.94-1.80 (4H).

Step d) Synthesis of (1H-Benzo[d]imidazol-1-yl)(3-(4-phenylpiperidin-1-yl)azetidin-1-yl)methanone To a solution of 1-(4-phenylpiperidine-1-yl)azetidin-1-carbonyl chloride (280 mg, 1.0 mmol) in dichloromethane (20 mL) at room temperature was added 1H-Benzo[d] imidazole (177 mg, 1.5 mmol) and triethylamine (0.22 ml, 1.5 mmol). The mixture stirred for 6 hours and diluted with water (10 ml). The organic layer was washed with brine, dried over MgSO$_4$ and solvent removed in vacuo. The crude material was purified by column chromatography on silica gel to give 0.26 g of (1H-Benzo[d]imidazol-1-yl)(3-(4-phenylpiperidin-1-yl)azetidin-1-yl)methanone as white solid.

¹H NMR (400 MHz, CDCl₃) δ: 8.20 (s, 1H); 7.95 (d, 1H, J=8.0 Hz); 7.80 (d, 1H, J=8.0 Hz); 7.41 (t, 1H, J=8.0 Hz); 7.38 (t, 1H, J=8.0 Hz); 7.32 (t, 2H, J=8.0 Hz); 7.25-7.19 (m, 3H); 4.5-4.35 (m, 4H); 4.32-4.24 (m, 2H); 3.55-3.35 (m, 1H); 3.2-2.9 (m, 2H); 2.70-2.50 (m, 1H); 2.20-1.80 (m, 4H)

Examples 84-91 were Synthesized by Method J

Example 84 (3-(4-Benzylpiperidine)azetidin-1-yl)(4-phenyl[1H] imizadol-1-yl)methanone ¹H NMR (400 MHz, CDCl₃) 8.00 (s, 1H); 7.78 (d, 2H, J=7.2 Hz); 7.54 (s, 1H); 7.39 (t, 2H, J=8.0 Hz); 7.28 (t, 3H, J=8. Hz); 7.20 (t, 1H, J=7.20 Hz); 7.14 (d, 2H, J=7.2 Hz); 4.40-4.42 (m, 4H); 3.34-3.24 (m, 1H); 2.95-2.87 (m, 2H); 2.56 (d, 2H, J=6.8 Hz); 1.73 (d, 2H, J=11.0 Hz), 1.65-1.54 (m, 3H); 1.46-1.34 (m, 2H)

Example 85 (4-Phenyl-1H-imidazol-1-yl)(3-(4-phenylpiperidin-1-yl)azetidin-1-yl)methanone ¹H NMR (400 MHz, CDCl₃) 8.03 (s, 1H); 7.80 (d, 2H, J=7.2 Hz); 7.57 (s, 1H); 7.40 (t, 2H, J=7.2 Hz); 7.31 (d, 2H, J=7.20 Hz) overlapping with (m, 1H); 7.23 (t, 2H, J=7.20 Hz) overlapping with (m, 1H); 4.45-4.35 (m, 2H); 4.34-4.4.25 (m, 2H); 3.4-3.30 (m,1H); 3.0 (d, 2H, J=9.2 Hz); 2.56 (t, 1H, J=9.2 Hz); 2.19 (t, 2H, J=9.2 Hz); 1.91-1.78 (m, 4H)

Example 86 (3-(4-Bromobenzyloxy)azetidin-1-yl)(4-phenyl-1H-imidazol-1-yl)methanone ¹H NMR (400 MHz, CDCl₃) 8.27 (s, 1H); 7.82 (d, 2H, J=7.6 Hz); 7.58 (s, 1H); 7.50 (d, 2H, J=8.0 Hz); 7.42 (t, 2H, J=7.6 Hz, J=2.0 Hz); 7.35 (t, 1H, J=8.0 Hz); 4.57-4.48 (m, 3H); 4.45 (s, 2H); 4.32-4.26 (m, 2H)

Example 87 (1H-Benzo[d]imidazol-1-yl)(3-(4-Bromobenzyloxy)azetidin-1-yl)methanone ¹H NMR (400 MHz, CDCl₃) 8.50 (s, 1H); 7.85 (d, 2H, J=7.2 Hz); 7.84 (d, 2H, J=7.2 Hz); 7.46 (td, 1H, J=8.0 Hz, J=2.0 Hz); 7.397 (td, 1H, J=8.0 Hz, J=2.0 Hz); 7.21 (d, 2H, J=8.0 Hz); 4.55-4.48 (m, 3H); 4.46 (s, 2H); 4.29-4.23 (m, 2H)

Example 88 3-(4-Bromobenzyloxy)azetidin-1-yl](piperidin-1-yl)methanone

¹H NMR (400 MHz, CDCl₃) 7.33 (d, 2H, J=7.6 Hz); 7.29-7.23 (m, 4H); 6.91 (d, 2H, J=7.2); 4.43 (s, 2H); 4.35-4.18 (m, 1); 4.14 (t, 2H, J=9.0 Hz); 3.93 (dd, 2H, J=9.0 Hz, J=4.0 Hz); 3.48 (t, 4H, J=4.80 Hz); 3.14 (t, 4H, J=4.80 Hz)

Example 89 (3-(4-Phenylpiperidin-1-yl)azetidin-1-yl)(1H-pyrazol-1-yl)methanone ¹H NMR (400 MHz, CDCl₃) 8.20 (s, 1H); 7.62 (s, 1H); 7.33 (t, 2H, J=8.0 Hz); 7.26 (t, 1H, J=8.0 Hz); 7.23 (d, 2H, J=8.0 Hz); 6.4 (s, 1H); 5.20-5.05 (m, 1H); 4.95-4.85 (m, 1H); 4.80-4.65 (m, 1H); 4.55-4.35 (m, 1H); 3.95-3.85 (m, 1H); 3.70-3.55 (m, 2H); 2.75-2.55 (m, 3H); 2.40 (q, 2H, J=12.0 Hz), 2.1 (d, 2H, J=12.0 Hz

Example 90 3-(4-Phenylpiperidin-1-yl)azetidin-1-yl)(1H-1,2,4-triazol-1-yl)methanone ¹H NMR (400 MHz, CDCl₃) 8.87 (d, 1H, J=3.2 Hz); 7.97 (d, 2H, J=3.2 Hz); 7.34-7.28 (m, 2H); 7.25-7.18 (m, 3H); 4.80-4.70 (m, 1H); 4.64-4.50 (m, 1H); 4.35-4.23 (m, 1H); 4.22-4.08 (m, 1H); 3.35-3.20 (m, 1H); 3.10-2.85 (m, 2H); 2.54 (t, 1H, J=12.0 Hz); 2.12-1.98 (m, 2H), 1.95-1.75 (m, 4H)

Example 91 3-(4-Bromophenylthio)azetidin-1-yl)(1H-1,2,4-triazol-1-yl)methanone ¹H NMR (400 MHz, CDCl₃) 8.88 (s, 1H) 7.97 (s, 1H); 7.45 (d, 2H, J=7.6 Hz); 7.16 (d, 2H, J=7.6 Hz); 5.15-5.0 (m, 1H); 4.70-4.50 (m, 2H); 4.20-4.15 (m, 2H)

Method K: Synthesis of N-Aryl Bridged Piperazine Urea Derivatives 51

Referring to Scheme XI, N-Aryl urea derivatives 51 were synthesized by reaction of bridged piperazine derivatives 50 with substituted biaryl phenyl carbamates 6 (scheme I), under microwave irradiation. Bridged piperazine derivatives 50 were obtained by deprotection of N—BOC group 49 under acidic condition. Which in turn were prepared by nucleophilic displacement of benzylic bromides with commercially available substituted N—BOC bridged piperazine 48.

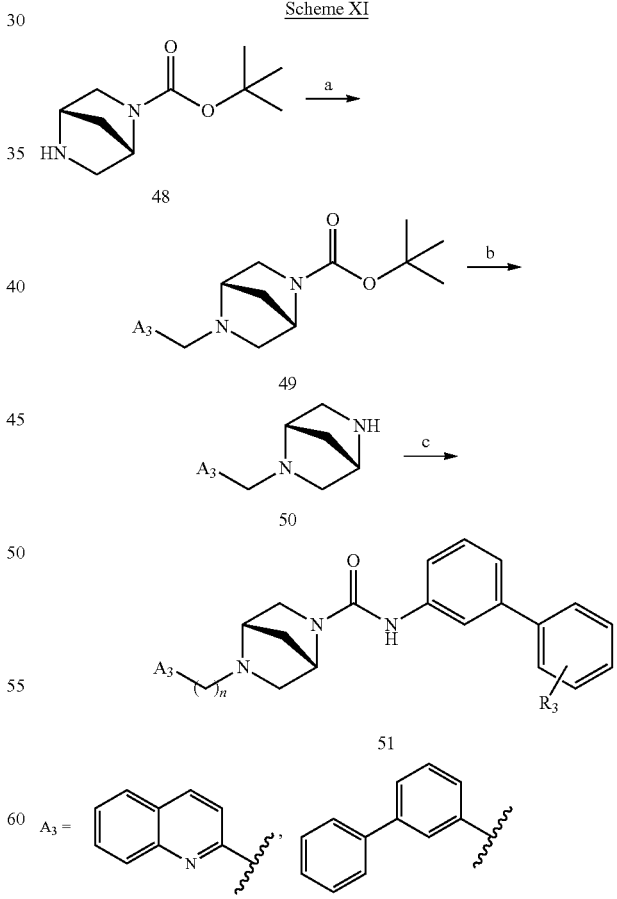

Scheme XI

Reagents: (a) ArCH₂Br, Et₃N, CH₃CN, microwave, 100° C., 15 min.; (b) TFA/CH₂Cl₂, rt, 16 h; (c) 6 (scheme I), CH₃CN, microwave, 110° C., 10 min.

The Following Examples were Prepared by Following Method K

Synthesis of Example 92: (1S,4S)—N-(3-Bromophenyl)-5-(quinolin-2-ylmethyl)-2,5-diazabicyclo [2.2.1] heptane-2-carboxamide (A$_1$=quinolin-2-yl, R$_3$=CONH$_2$)

Step a) Synthesis of tert-Butyl (1S,4S)-5-(quinolin-2-ylmethyl)-2,5-diazabicyclo[2.2.1] heptane-2-carboxylate 49 (A$_1$=quinolin-2-yl)

To a solution of 2-(chloromethyl)quinoline hydrobromide (2.0 g, 7.74 mmol) in acetonitrile (20 mL) was added tort-butyl (1S,4S)-2,5-diazabicyclo[2.2.1]heptane-2-carboxylate 48, (1.86 g, 9.28 mmol) and triethylamine (1.61 mL, 16.1 mmol) and the resulting mixture was heated in a sealed tube under microwave irradiation at 100° C. for 15 min with stirring. The reaction mixture was cooled to room temperature. The solvent was removed in vacuo and the residue partitioned between dichloromethane and water. The aqueous layer was further extracted with dichloromethane and the combined organic extracts were washed with brine, and dried over MgSO$_4$. The solvent was removed in vacuo to give a crude product, which was purified by flash column chromatography to give 2.25 g of tert-butyl (1S,4S)-5-(quinolin-2-ylmethyl)-2,5-diazabicyclo[2.2.1] heptane-2-carboxylate as colorless oil.

$^1$H NMR (500 M Hz, CDCl$_3$) δ 8.09 (d, 1H, J=9 Hz); 8.06 (d, 1H, J=9.0 Hz); 7.81 (d, 1H, J=8.0 Hz); 7-71-7.66 (m, 2H); 7.51 (t, 1H, J=8.0 Hz); 7.13 (bd, 1H, J=9.0 Hz) 7.06 (bd, 1H, J=9.0 Hz); 4.25 (d, 1H, J=14 Hz); 3.84-3.65 (m, 3H); 3.15 (bs, 1H); 2.93 (bs, 1H); 2.70 (brs, 1H); 2.58 (brs, 1H); 0.96 (brs, 9H)

Step b) Synthesis of 2-(((1S,4S)-2,5-diazabicyclo [2.2.1]heptan-2-yl)methyl)quinoline To a solution of tert-butyl (1S,4S)-5-(quinolin-2-ylmethyl)-2,5-diazabicyclo[2.2.1] heptane-2-carboxylate (2.0 g, 5.86 mmol) in methylene chloride (25 mL) was added trifluoroacetic acid (2.2 mL, 29.3 mmol). After stirring at room temperature for 16 h, the mixture was concentrated in vacuo, and residue was partitioned between ethyl acetate and aqueous sodium bicarbonate. The aqueous layer was extracted with Ethyl acetate and the combined organic layer was washed with water (20 mL) brine (20 mL), and dried over MgSO$_4$. The solvent was removed in vacuo to give 2-(((1S,4S)-2,5-diazabicyclo[2.2.1]heptan-2-yl)methyl)quinolone (1.27 g) which was used for next reaction without further purification.

$^1$H NMR (500 M Hz, CDCl$_3$) δ 8.13 (d, 1H, J=9 Hz); 8.06 (d, 1H, J=9.0 Hz); 7.81 (d, 1H, J=8.0 Hz); 7-71-7.66 (m, 2H); 7.51 (t, 1H, J=8.0 Hz); 7.14 (bd, 1H, J=9.0 Hz) 7.05 (bd, 1H, J=9.0 Hz); 4.25 (d, 1H, J=14 Hz); 3.84-3.65 (m, 3H); 3.15 (brs, 1H); 2.93 (brs, 1H); 2.70 (brs, 1H); 2.58 (brs, 1H Step c) Synthesis of (1S,4S)—N-(3-bromophenyl)-5-(quinolin-2-ylmethyl)-2,5-diazabicyclo [2.2.1] heptane-2-carboxamide A solution of 2-(((1S,4S)-2,5-diazabicyclo[2.2.1]heptan-2-yl)methyl)quinoline (0.5 g, 2.34 mmol) and biphenyl-3-yl-carbamic acid phenyl ester 6 (0.92 g, 2.77 mmol) in acetonitrile (10 mL) was heated in a sealed tube under microwave irradiation at 120° C. for 10 min with stirring. The reaction mixture was cooled to room temperature and solvent was removed under reduced pressure. The crude material was partitioned between dichloromethane and water. The aqueous phase was extracted with dichloromethane. The combined organic extracts was washed with water (10 mL), brine (10 mL) and dried over MgSO$_4$. The solvent was removed in vacuo to give residue which was chromatographed to give 0.60 g of (1S,4S)—N-(3-bromophenyl)-5-(quinolin-2-ylmethyl)-2,5-diazabicyclo[2.2.1] heptane-2-carboxamide, as white solid.

$^1$H NMR (500 M Hz, CDCl$_3$) δ 8.16 (d, 1H, J=7 Hz); 8.02 (d, 1H, J=7 Hz); 8.01 (s, 1H); 7.81 (d, 1H, J=7 Hz); 7.68-7.73 (m, 3H); 7.65 (d, 1H, J=5 Hz); 7.58-7.52 (m, 2H); 7.41-7.46 (m, 2H); 7.32 (t, 1H, J=7.5 Hz); 7.21 (d, 1H, J=7.5 Hz); 6.99 (s, 1H); 6.45 (brs, 1H); 6.48 (brs, 1H); 4.24 (d, 1H, J=12 Hz); 3.86 (d, 1H, J=13 Hz); 3.74 (td, 1H, J=12.5 Hz); 3.63 (d, 1H, J=14 Hz); 3.24 (td, 1H, J=10 Hz, J=3 Hz); 3.03 (dd, 1H, J=13 Hz, J=9 Hz); 2.77 (dt, 1H, J=12 Hz, J=4.0 Hz); 2.64-2.59 (m, 1H); 2.36 (t, J=12.5 Hz, J=3.0 Hz); 1.19 (d, 3H, J=6.5 Hz)

Examples 93-95 were Prepared According to Method K

Example 93: (1S,4S)—N-(3'-cyano-[1,1'-biphenyl]-3-yl)-5-(quinolin-2-ylmethyl)-2,5-diazabicyclo [2.2.1] heptane-2-carboxamide $^1$H-NMR: CDCl3 δ: 8.12 (d, 1H, J=8 Hz), 8.06 (d, 1H, J=8 Hz), 7.92 (s, 1H), 7.82 (d, 2H, J=8 Hz), 7.71-7.69 (m, 2H), 7.67 (d, 1H, J=8.5 Hz), 7.61 (td, 1H), 7.55-7.49 (m, 2H), 7.37 (t, 1H, J=8 Hz), 7.30 (dd, 1H, J1=1.5 Hz, J2=8 Hz), 7.24 (td, 1H), 6.45 (s, 1H), 4.29 (d, 1H, J=14 Hz), 3.84 (d, 1H), 3.72 (t, 1H, J=8.5 Hz), 3.68 (d, 1H, J=14.5 Hz), 3.29 (td, 1H), 3.06 (dd, 1H, J=9 Hz, J=13 Hz), 2.83 (td, 1H, J=8.5 Hz), 2.73-2.67 (m, 1H), 2.43 (td, 1H), 1.24 (d, 3H, J=6.5 Hz)

Example 94: (1S,4S)-5-([1,1'-biphenyl]-3-ylmethyl)-N-(3'-cyano-[1,1'-biphenyl]-3-yl)-2,5-diazabicyclo[2.2.1]heptane-2-carboxamide $^1$H-NMR: CDCl3 δ: 8.14 (d, 1H, J=8 Hz), 7.96 (d, 1H, J=8 Hz), 7.92 (s, 1H), 7.83 (d, 2H, J=8 Hz), 7.70-7.67 (m, 2H), 7.65 (d, 1H, J=8.5 Hz), 7.59 (td, 1H), 7.55-7.49 (m, 2H), 7.37 (t, 1H, J=8 Hz), 7.28 (dd, 1H, J1=1.5 Hz, J2=8 Hz), 7.24 (s, 1H), 6.45 (s, 1H), 4.29 (d, 1H, J=14 Hz), 3.84 (td, 1H), 3.72 (t, 1H, J=8.5 Hz), 3.68 (d, 1H, J=14.5 Hz), 3.29 (td, 1H), 3.06 (dd, 1H, J=9 Hz, J=13 Hz), 2.81 (d, 1H, J=8.5 Hz), 2.72-2.67 (m, 1H), 2.43 (d, 1H, J=4.5 Hz), 1.22 (d, 3H, J=6.5 Hz)

Example 95: (1S,4S)—N-(3-bromophenyl)-5-(quinolin-2-ylmethyl)-2,5-diazabicyclo[2.2.1]heptane-2-carboxamide $^1$H-NMR: CDCl3 δ: 8.04 (d, 1H, J=8 Hz), 7.98 (d, 1H, J=8 Hz), 7.92 (s, 1H), 7.81 (d, 2H, J=8 Hz), 7.71-7.69 (m, 2H), 7.65 (d, 1H, J=8.5 Hz), 7.61 (td, 1H), 7.55-7.49 (m, 2H), 7.37 (t, 1H, J=8 Hz), 7.30 (dd, 1H, J1=1.5 Hz, 0.12=8 Hz), 7.24 (td, 1H), 6.45 (s, 1H), 4.29 (d, 1H, J=14 Hz), 3.84 (td, 1H), 3.72 (t, 1H, J=8.5 Hz), 3.68 (d, 1H, J=14.5 Hz), 3.29 (td, 1H), 3.06 (dd, 1H, J=9 Hz, J=13 Hz), 2.83 (td, 1H, J=8.5 Hz), 2.72-2.67 (m, 1H), 2.43 (td, 1H), 1.22 (d, 3H, J=6.5 Hz)

Method L: Synthesis of Imidazolyl Ureas 56 and 57

Imidazolyl ureas 56 and 57 (Scheme XII) were synthesized by reaction of bridged piperazine derivatives 50

(Scheme XI) or 55 with 4-nitrophenyl 4-phenyl-1H-imidazole-1-carboxylate 9 (Scheme II) in dichloromethane. Intermediate bridged piperazine 55 was synthesized by N-arylation of commercially available tert-butyl (1S,4S)-2,5-diazabicyclo[2.2.1]heptane-2-carboxylate 48 with aryl bromides under the Buchwald coupling condition (Bermejo et al, *J. Am. Chem. Soc.*, (2008) 130: 15798-15799), followed by deprotection of N—BOC group under acidic condition.

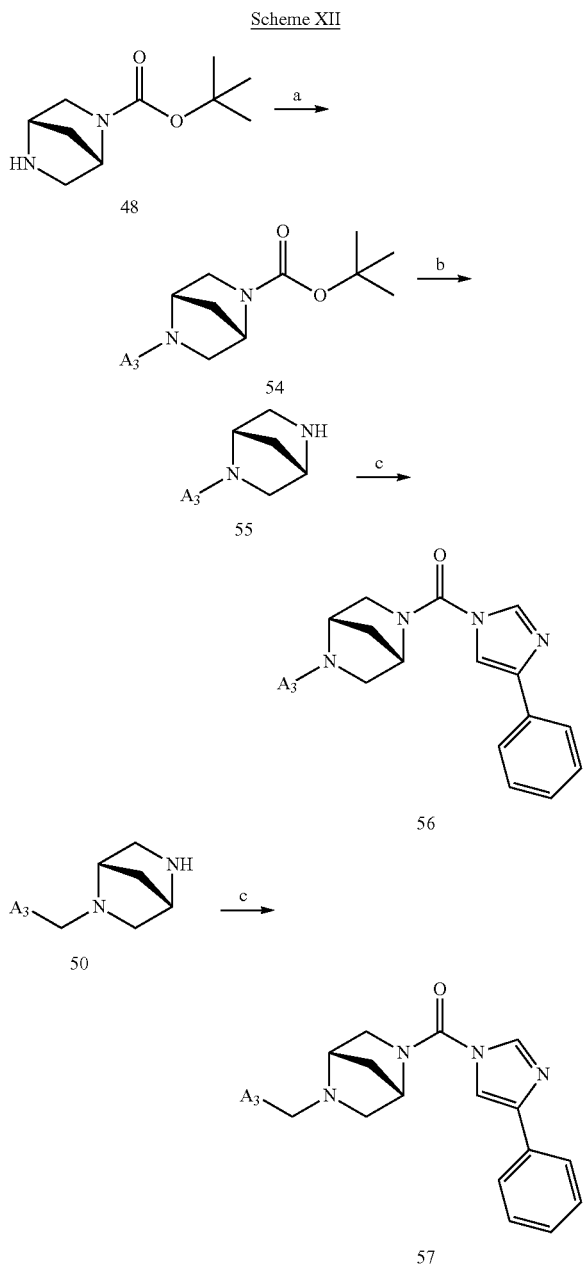

Scheme XII

Reagents: (a) Ar—Br, Pd$_2$(dba)$_3$, BINAP, NaOtBu, DME, 80° C., 8-12 h; (b) TFA/CH$_2$Cl$_2$, rt; (c) 9 CH$_2$Cl$_2$, rt, 2 h.

The following examples were prepared by following Method L Synthesis of Example 96, (4-Phenyl 4H-imidazol-1-yl)((1S,4S)-5-(pyridin-2-yl)-2,5-diazabicyclo[2.2.1] heptan-2-yl)methanone Step a) Synthesis of tert-Butyl (1S,4S)-5-(pyridin-2-yl)-2,5-diazabicyclo[2.2.1]heptane-2-carboxylate (54: A$_3$=pyridin-2-yl)

A degassed mixture of commercially available 2-bromopyridine (0.72 g, 1.5 mmol), text-butyl (1S,4S)-2,5-diazabicyclo[2.2.1]heptane-2-carboxylate (162 mg, 1.5 mmol) 48, BINAP (124 mg, 0.08 mmol), Pd$_2$dba$_3$ (156 mg, 0.05 mmol), and sodium tert-butoxide (1.54 g, 1.55 mmol), in 1,2-dimethoxy ethane was heated in a sealed tube at 120° C. for 12 h. The reaction mixture was poured into water (15 mL) and extracted with ethyl acetate (2×30 mL). The combined organic layer was washed with water (20 mL) and brine (20 mL), dried over MgSO$_4$ and evaporated. Further purification of crude material by flash chromatography on silica gel gave tert-butyl (1S,4S)-5-(pyridin-2-yl)-2,5-diazabicyclo[2.2.1] heptane-2-carboxylate (0.58 g) as light yellow liquid.

$^1$H NMR (500 M Hz, CDCl$_3$) δ 8.13 (d, 1H, J=9 Hz); 8.06 (d, 1H, J=9.0 Hz); 7.81 (d, 1H, J=8.0 Hz); 7-71-7.66 (m, 2H); 7.51 (t, 1H, J=8.0 Hz); 7.23 (bd, 1H, J=9.0 Hz) 7.05 (bd, 1H, J=9.0 Hz); 4.25 (d, 1H, J=14 Hz); 3.84-3.65 (m, 3H); 3.15 (brs, 1H); 2.93 (brs, 1H); 2.70 (brs, 1H); 2.58 (brs, 1H)

Step b) Synthesis of (1S,4S)-2-(Pyridin-2-yl)-2,5-diazabicyclo[2.2.1]heptane (55: A$_3$=pyridin-2-yl)

To a solution of tert-butyl (1S,4S)-5-(pyridin-2-yl)-2,5-diazabicyclo[2.2.1]heptane-2-carboxylate (1.5 g, 5.86 mmol) in methylene chloride (25 mL) was added trifluoroacetic acid (2.25 mL, 29.3 mmol). After stirring at room temperature for 16 h, the mixture was concentrated in vacuo, and diluted with ethyl acetate and aqueous sodium bicarbonate. The organic layer was washed with water (10 mL), brine (10 mL), dried over MgSO$_4$. The solvent was removed in vacuo to give to give 1S,4S)-2-(pyridin-2-yl)-2,5-diazabicyclo[2.2.1]heptane (1.01 g) which was used in the next step without further purification.

Step c) Synthesis of (4-phenyl-1H-imidazol-1-yl)((1S,4S)-5-(pyridin-2-yl)-2,5-diazabicyclo [2.2.1] heptan-2-yl)methanone To a solution of (1S,4S)-2-(pyridin-2-yl)-2,5-diazabicyclo [2.2.1]heptane (0.7 g, 3.17 mmol) in dichloromethane was added 4-phenylimidazole-4-nitrophenyl carboxylate (1.21 g, 3.64 mmol) 9 (scheme II) and mixture was stirred at room temperature for 2 hours. Solvent was removed under reduced pressure. The residue was chromatographed over silica gel to give (4-phenyl-1H-imidazol-1-yl)((1S4S)-5-(pyridin-2-yl)-2,5-diazabicyclo[2.2.1]heptan-2-yl)methanone (1.21 g) as white solid.

1H NMR (500 MHz, CDCl3) δ 7.98 (s, 1H); 7.81 (d, 2H, J=8.0 Hz); 7.53 (s, 1H); 7.41 (t, 2H, J=7.5 Hz); 7.34 (dt, 1H, J=8.0 Hz, J=2.0 Hz); 7.11-6.92 (m, 5H, J=8.0 Hz); 6.88-6.81 (m, 4H); 3.97 (dt, 1H, J=13.0 Hz, J=4.5 Hz); 3.85 (dd, 1H, J=13.0 Hz, J=2.0 Hz); 3.72-3.6 (m, 3H); 3.19 (qd, 2H, J=13.0, J=3.5 Hz); 2.30 (s, 3H), 1.03 (d, 3H, J=6.0 Hz).

Examples 97-100 were Prepared According to Method B

Example 97: ((1S,4S)-5-(3-Fluorophenyl)-2,5-diazabicyclo[2.2.1]heptan-2-yl)(4-phenyl-1H-imidazol-1-yl)methanone $^1$H NMR (500 MHz, CDCl$_3$) δ 7.89 (d, 1H, J=7.5 Hz); 7.77 (d, 1H, J=2.0 Hz); 7.53 (t, 1H, J=8.0 Hz), 7.18 (d, 1H, J=1.0 Hz); 7.06 (t, 1H, J=7.5 Hz, J=1.0 Hz); 7.01 (d, 1H, J=8.0 Hz); 3.96 (d, 2H, J=13.0 Hz), 3.54 (dt, 2H, J=13.0 Hz, J=2.0 Hz); 2.77 (s, 2H); 2.20 (d, 2H, J=13.0 Hz), 1.74 (dt, 2H, J=13.5 Hz, J=5.0 Hz).

Example 98: ((1S,4S)-5-(3-(Benzyloxy)phenyl)-2,5-diazabicyclo[2.2.1]heptan-2-yl)(4-phenyl-1H-imidazol-1-yl)methanone $^1$H NMR (500 MHz, CDCl$_3$) δ 7.96 (s, 1H); 7.81 (d, 2H, J=8.0 Hz); 7.51 (s, 1H); 7.41 (t, 2H, J=7.5 Hz); 7.30 (t, 3H, J=7.5 Hz); 6.96 (d as m, 3H, J=8.0 Hz); 4.05 (dt, 1H, J=13.0 Hz, J=4.0 Hz); 3.90-3.82 (m, 1H); 3.77 (t, 2H, J=4.0 Hz); 3.56 (dd, 1H, J=26.0 J=14.0 Hz J=5.0 Hz); 3.26 (d as m, 1H, J=12.0 Hz, J=3.5 Hz); 2.90 (dt, 1H, J=13.0 Hz, J=3.0 Hz); 1.06 (d, 3H, J=7.0 Hz).

Example 99: ((1S,4S)-5-([1,1'-Biphenyl]-3-ylmethyl)-2,5-diazabicyclo[2.2.1]heptan-2-yl)(4-phenyl-1H-imidazol-1-yl)methanone $^1$H NMR (500 MHz, CDCl$_3$) δ 7.89 (d, 1H, J=7.5 Hz); 7.77 (d, 1H, J=2.0 Hz); 7.53 (t, 1H, J=8.0 Hz), 7.18 (d, 1H, J=1.0 Hz); 7.06 (t, 1H, J=7.5 Hz, J=1.0 Hz); 7.01 (d, 1H, J=8.0 Hz); 3.96 (d, 2H, J=13.0 Hz), 3.54 (dt, 2H, J=13.0 Hz, J=2.0 Hz); 2.77 (s, 2H); 2.20 (d, 2H, J=13.0 Hz), 1.74 (dt, 2H, J=13.5 Hz, J=5.0 Hz).

Example 100: ((1S,4S)-5-([1,1'-Biphenyl]-3-ylmethyl)-2,5-diazabicyclo[2.2.1]heptan-2-yl)(4-bromo-1H-imidazol-1-yl)methanone $^1$H NMR (500 MHz, CDCl$_3$) δ 7.96 (s, 1H); 7.81 (d, 2H, J=8.0 Hz); 7.51 (s, 1H); 7.41 (t, 2H, J=7.5 Hz); 7.30 (dt, 1H, J=8.0 Hz, J=2.0 Hz); 7.11 (d, 2H, J=8.0 Hz); 6.88 (d, 2H, J=8.0 Hz); 3.96 (dt, 1H, J=13.0 Hz, J=4.5 Hz); 3.80 (dd, 1H, J=13.0 Hz, J=2.0 Hz); 3.72-3.6 (m, 3H); 3.18 (qd, 2H, J=13.0, J=3.5 Hz); 2.30 (s, 3H), 1.01 (d, 3H, J=6.0 Hz).

Method M: Synthesis of Phenyl Carbamates 58

As shown in scheme XIII, phenyl (1S,4S)-5-([1,1'-biphenyl]-3-ylmethyl)-2,5-diazabicyclo[2.2.1]heptane-2-carboxylate 58 was obtained by reaction of bridged piperazine 50, (scheme XI) with phenyl chloroformate at room temperature Scheme XIII:

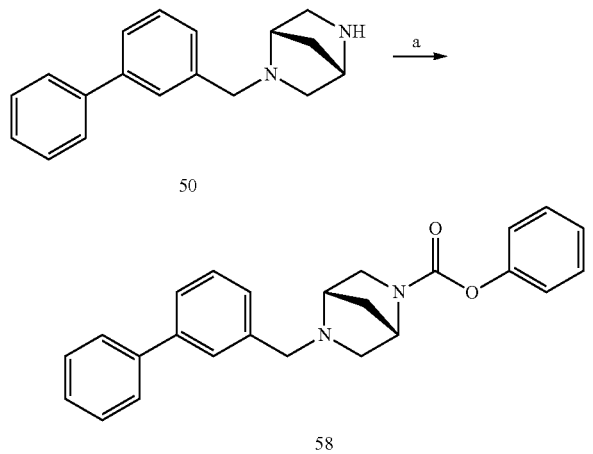

Reagents: (a) Phenyl chloroformate, Et$_3$N, CH$_2$Cl$_2$, rt, 2 h.

The Following Examples were Prepared by Following Method M

Synthesis of Example 101: phenyl (1S,4S)-5-([1,1'-Biphenyl]-3-ylmethyl)-2,5-diazabicyclo[2.2.1]heptane-2-carboxylate To a stirred solution of phenyl chloroformate (0.51 mL, 1.53 mmol,) in methylene chloride (20 mL) at room temperature was added (1S,4S)-2-([1,1'-biphenyl]-3-ylmethyl)-2,5-diazabicyclo[2.2.1]heptane (50, 0.49 g, 1.34 mmol) and triethylamine (0.45 mL, 2.1 mmol). The resulting mixture was stirred at room temperature for 2 hours. After the completion of reaction, as monitored by TLC, the mixture was diluted with water, the aqueous layer was extracted with methylene chloride (2×10 mL), and the combined organic layer was dried over MgSO$_4$. The solvent was removed under reduced pressure to give a crude material, which was purified by column chromatography on silica gel to afford 0.54 g of phenyl (1S,4S)-5-([1,1'-biphenyl]-3-ylmethyl)-2,5-diazabicyclo[2.2.1]heptane-2-carboxylate 58 as white solid.

$^1$H NMR (500 MHz, CDCl3) δ 7.98 (s, 1H); 7.81 (d, 2H, J=8.0 Hz); 7.53 (s, 1H); 7.41 (t, 2H, J=7.5 Hz); 7.34 (dt, 1H, J=8.0 Hz, J=2.0 Hz); 7.11-6.92 (m, 5H, J=8.0 Hz); 6.88-6.81 (m, 4H); 3.97 (td, 1H, J=13.0 Hz, J=4.5 Hz); 3.85 (dd, 1H, J=13.0 Hz, J=2.0 Hz); 3.72-3.6 (m, 3H); 3.19 (qd, 2H, J=13.0, J=3.5 Hz); 2.30 (s, 3H), 1.03 (d, 3H, J=6.0 Hz).

Testing of Inhibitory Compounds

Certain compounds were tested for their MAGL inhibitory activity, which is expressed as IC$_{50}$ values see Table 1. The IC$_{50}$ is the concentration of the inhibitor, which results in 50% inhibition of the velocity/rate of 2-AG hydrolysis by FAAH/MAGL. The lower the IC$_{50}$ values, the higher its inhibitory activity. A detailed description of the methods used to test inhibitory activity of compounds is given below.

Example 102: Preparation of Human MAGL (hMAGL)

Recombinant hexahistidine-tagged human MAGL (hMAGL) was expressed in E. coli cells and purified following our recently reported procedures (Zvonok et al Chem. Biol. (2008) 15: 854-862), (Zvonok et al. Proteome Res. (2008) 7: 2158-2164).

Example 103: Preparation of Rat MAGL (rMAGL)

Recombinant rMAGL (rMAGL) was expressed in E. coli cells and purified as described for Hmag, (Zvonok et al Chem. Biol. (2008) 15: 854-862), (Zvonok et al J. Proteome Res. (2008) 7: 2158-2164).

Example 104: Fluorescent Assay Protocol for hMAGL

Compound inhibition of hMAGL activity was assessed by a fluorometric assay recently developed in our laboratory (Makriyannis et al WO Patent Application 2009/117444 A1, (2009) 109 pp.), (Zvonok et al Chem. Biol. (2008) 15: 854-862), (Zvonok et al J. Proteome Res. (2008) 7: 158-2164). This medium throughput assay involved a 96-well plate format in which hMAGL activity was monitored by the hydrolysis of the substrate 7-hydroxy-6-methoxy-4-methyl-coumarin ester (AHMMCE) to form the fluorescent product, coumarin. In brief, various concentrations of each compound were preincubated with hMAGL (175 ng of total protein in *E. coli* lysate containing hMAGL) for 15 min at room temperature. Upon the addition of AHMMCE, the reaction was incubated at 25° C. for 120 min; fluorescence readings were taken every 15 min at 360 nm/460 nm (λexcitation/λemission) using a Synergy HT Plate Reader (Bio-Tek, Winooski, Vt.). Under these incubation conditions, negligible spontaneous AHMMCE hydrolysis was observed. External standards were used to convert relative fluorescence units to the amount of 4-methylcoumarin formed. All MAGL assays were performed in triplicate for each inhibitor concentration, and IC50 values were calculated using Prizm software (GraphPad. Software, Inc., San Diego, Calif.).

Example 105: Fluorescent Assay Protocol for rMAGL

Procedure was followed as described for hMAGL.

Example 106: Preparation of Transmembrane Domain-Deleted Rat FAAH (ΔTM rFAAH)

Rat ΔTM FAAH was expressed in *E. coli* cells and purified using the procedure disclosed by Patricelli et al. *Biochemistry* (1998) 37: 15177-15187.

Example 107: Preparation of Human FAAH in Fusion with N-Terminal Maltose Binding Tag (MBPΔTMhFAAH)

Human FAAH without putative transmembrane domain following maltose binding protein was expressed in *E. coli* cells using pMALcE4 vector Alapafuja et al *J. Med. Chem.* (2012) 55: 10074-89.

Example 108: Fluorescent Assay Protocol for ΔTM Rat FAAH

Procedure was followed as described for hMAGL, except that arachidonoyl-methyl coumarin amide (AAMCA) was used as fluorigenic substrate. Compounds were diluted in 50:50 DMSO/assay buffer (50 mM HEPES, 1 mM EDTA, 0.1% BSA, pH 7.4) so as to have a final DMSO concentration below 8% in each reaction. For the screening assay, 3 concentrations (1 μM, 10 μM, and 100 μM) of test compounds, 15 μg of ΔTM rFAAH and assay buffer were pre-incubated for 15 min at 25° C. AAMCA (20 μM, 2×Km) was added prior to incubation at 25° C. and kinetic fluorescence reading every 20 minutes ($\lambda_{ex}$=360/$\lambda_{em}$=460) for 4 hours on a BioTek Synergy HT Microplate Reader (BioTek Instruments, Winooski, Vt.). The fluorescence reading at the 3 hour time point (linear enzyme kinetics) was used to calculate percent inhibition based on control assays without inhibitor present. All FAAH assays were performed in triplicate for each inhibitor concentration, and $IC_{50}$ values determined using Prizm software (GraphPad Software, Inc.).

Example 109: Fluorescent Assay Protocol for hFAAH

Procedure was followed as described for rFAAH.
For Table 1 the FAAH/MAGL inhibition as $IC_{50}$ μM index is as follow:
A=0.01 μM-0.1 μM
B=0.11 μM-1.00 μM
C=>1.00 μM

TABLE 1

| Examples | rFAAH | hFAAH | rMAGL | hMAGL |
|---|---|---|---|---|
| Example 1 | A | A | C | C |
| Example 2 | B | C | C | C |
| Example 3 | A | A | C | C |
| Example 4 | A | A | C | C |
| Example 5 | C | C | C | C |
| Example 6 | A | A | B | B |
| Example 7 | A | A | C | C |
| Example 8 | A | A | C | C |
| Example 9 | A | A | C | C |
| Example 10 | A | A | C | C |
| Example 11 | A | A | C | C |
| Example 12 | A | A | C | C |
| Example 13 | A | A | C | C |
| Example 14 | C | C | C | C |
| Example 15 | C | C | C | C |
| Example 16 | C | C | C | C |
| Example 17 | A | A | C | C |
| Example 18 | A | B | C | C |
| Example 19 | B | B | C | C |
| Example 20 | B | B | C | C |
| Example 21 | B | B | C | C |
| Example 22 | B | B | C | C |
| Example 23 | A | B | C | C |
| Example 24 | A | B | C | C |
| Example 25 | A | A | C | C |
| Example 26 | A | B | C | C |
| Example 27 | B | B | C | C |
| Example 28 | B | B | C | C |
| Example 29 | B | B | C | C |
| Example 30 | C | B | C | C |
| Example 31 | A | A | C | C |
| Example 32 | B | B | C | C |
| Example 33 | C | C | C | C |
| Example 34 | A | A | C | C |
| Example 35 | C | C | C | C |
| Example 36 | A | A | C | C |
| Example 37 | A | A | C | C |
| Example 38 | B | B | C | C |
| Example 39 | B | B | C | C |
| Example 40 | C | C | C | B |
| Example 41 | B | B | C | C |
| Example 42 | C | C | A | A |
| Example 43 | C | C | A | A |
| Example 44 | A | A | C | C |
| Example 45 | A | A | C | C |
| Example 46 | A | A | C | C |
| Example 47 | A | A | C | C |
| Example 48 | B | A | C | C |
| Example 49 | C | C | B | B |
| Example 50 | C | C | B | B |
| Example 51 | A | A | C | C |
| Example 52 | A | A | B | A |
| Example 53 | A | A | A | A |
| Example 54 | B | A | B | B |
| Example 55 | A | A | B | A |
| Example 56 | B | B | B | B |
| Example 57 | C | C | A | A |
| Example 58 | C | C | A | A |
| Example 59 | B | A | A | A |
| Example 60 | B | A | A | A |
| Example 61 | A | A | A | C |
| Example 62 | A | A | A | C |
| Example 63 | C | C | B | B |
| Example 64 | C | C | A | A |
| Example 65 | C | C | B | B |
| Example 66 | C | C | A | A |
| Example 67 | C | C | A | A |
| Example 68 | C | C | B | B |
| Example 69 | B | B | A | A |
| Example 70 | B | B | B | B |
| Example 71 | B | B | A | A |
| Example 72 | B | B | B | B |
| Example 73 | C | C | A | A |
| Example 74 | A | A | C | B |
| Example 75 | A | A | C | B |
| Example 76 | A | A | B | B |

TABLE 1-continued

| Examples | IC50 | | | |
|---|---|---|---|---|
| | rFAAH | hFAAH | rMAGL | hMAGL |
| Example 77 | A | A | B | B |
| Example 78 | A | A | C | C |
| Example 79 | A | A | B | B |
| Example 80 | A | A | C | C |
| Example 81 | B | B | C | C |
| Example 82 | B | B | C | C |
| Example 83 | A | A | C | C |
| Example 84 | A | A | C | C |
| Example 85 | A | A | C | C |
| Example 86 | A | A | C | C |
| Example 87 | A | A | A | A |
| Example 88 | A | A | A | A |
| Example 89 | A | A | A | A |
| Example 90 | A | A | A | A |
| Example 91 | A | A | A | A |
| Example 74 | A | A | C | B |
| Example 75 | A | A | C | B |
| Example 76 | A | A | B | B |
| Example 77 | A | A | B | B |
| Example 78 | A | A | C | C |
| Example 79 | A | A | B | B |
| Example 80 | A | A | C | C |
| Example 81 | B | B | C | C |
| Example 82 | B | B | C | C |
| Example 83 | A | A | C | C |
| Example 84 | A | A | C | C |
| Example 85 | A | A | C | C |
| Example 86 | A | A | C | C |
| Example 87 | A | A | A | A |
| Example 88 | A | A | A | A |
| Example 89 | A | A | A | A |
| Example 90 | A | A | A | A |
| Example 91 | A | A | A | A |
| Example 92 | C | C | C | C |
| Example 93 | C | C | C | C |
| Example 94 | B | B | C | C |
| Example 95 | A | A | C | C |
| Example 96 | A | A | C | C |
| Example 97 | B | B | C | C |
| Example 98 | C | C | C | C |
| Example 99 | A | B | C | C |
| Example 100 | A | A | C | C |
| Example 101 | A | A | C | C |

Example names and structures are provided below, in Table 2.

| Example | Name | Structure |
|---|---|---|
| Example 1 | (S)-N-(3'-carbamoyl-[1,1'-biphenyl]-3-yl)-3-methyl-4-(quinolin-2-ylmethyl)piperazine-1-carboxamide | 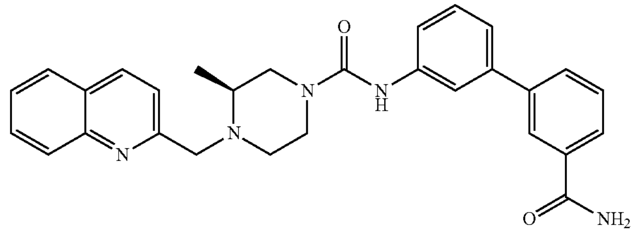 [SMILES: C[C@H]1CN(C(=O)Nc2cccc(-c3cccc(C(N)=O)c3)c2)CCN1Cc1ccc2ccccc2n1] |
| Example 2 | (R)-N-(3'-carbamoyl-[1,1'-biphenyl]-3-yl)-3-methyl-4-(quinolin-2-ylmethyl)piperazine-1-carboxamide | 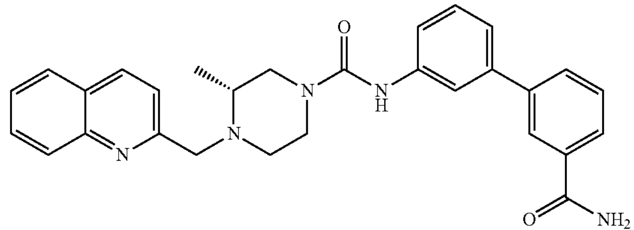 [SMILES: C[C@@H]1CN(C(=O)Nc2cccc(-c3cccc(C(N)=O)c3)c2)CCN1Cc1ccc2ccccc2n1] |
| Example 3 | (S)-N-(3'-cyano-[1,1'-biphenyl]-3-yl)-2-methyl-4-(3-phenoxybenzyl)piperazine-1-carboxamide | 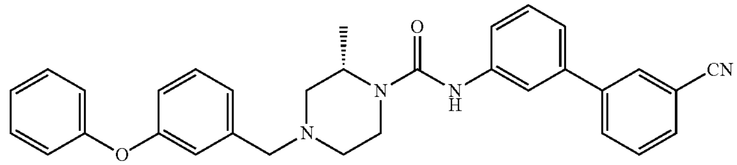 [SMILES: C[C@H]1CN(Cc2cccc(Oc3ccccc3)c2)CCN1C(=O)Nc1cccc(-c2cccc(C#N)c2)c1] |
| Example 4 | (S)-N-(3'-carbamoyl-[1,1'-biphenyl]-3-yl)-2-methyl-4-(3-phenoxybenzyl)piperazine-1-carboxamide | 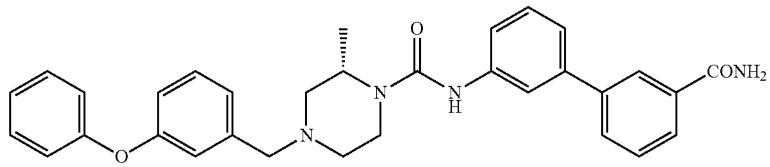 [SMILES: C[C@H]1CN(Cc2cccc(Oc3ccccc3)c2)CCN1C(=O)Nc1cccc(-c2cccc(C(N)=O)c2)c1] |

-continued

| Example | Name | Structure |
|---|---|---|
| Example 5 | (S)-N-(5-(3-cyanophenyl)pyridin-3-yl)-2-methyl-4-(3-phenoxybenzyl)piperazine-1-carboxamide | 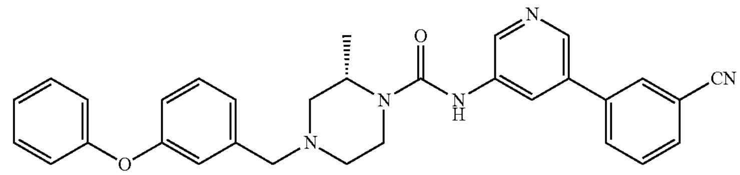 [SMILES: C[C@H]1CN(Cc2cccc(Oc3ccccc3)c2)CCN1C(=O)Nc1cncc(-c2cccc(C#N)c2)c1] |
| Example 6 | N-(3'-carbamoyl-[1,1'-biphenyl]-3-yl)-4-(quinolin-3-ylmethyl)piperazine-1-carboxamide | 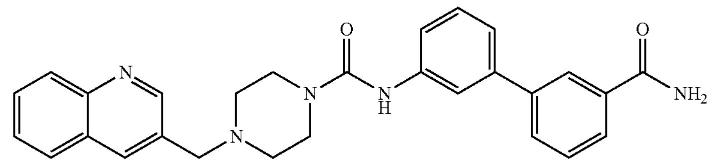 [SMILES: NC(=O)c1cccc(-c2cccc(NC(=O)N3CCN(Cc4cnc5ccccc5c4)CC3)c2)c1] |
| Example 7 | N-(3'-carbamoyl-[1,1'-biphenyl]-3-yl)-4-phenylpiperidine-1-carboxamide | 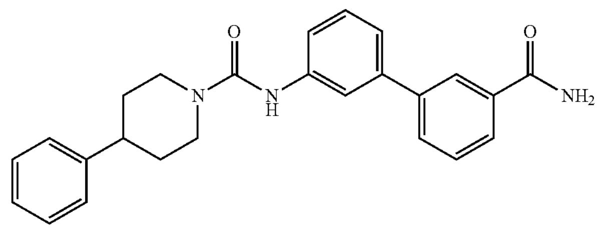 [SMILES: NC(=O)c1cccc(-c2cccc(NC(=O)N3CCC(c4ccccc4)CC3)c2)c1] |
| Example 8 | N-(3'-carbamoyl-[1,1'-biphenyl]-3-yl)-4-(9H-fluoren-9-yl)piperazine-1-carboxamide | 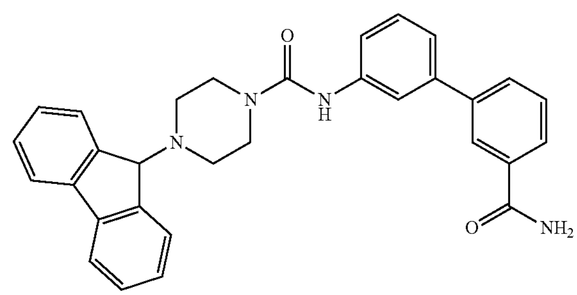 [SMILES: NC(=O)c1cccc(-c2cccc(NC(=O)N3CCN(C4c5ccccc5-c5ccccc54)CC3)c2)c1] |
| Example 9 | N-(3'-carbamoyl-[1,1'-biphenyl]-3-yl)-4-(pyridin-2-yl)piperazine-1-carboxamide | 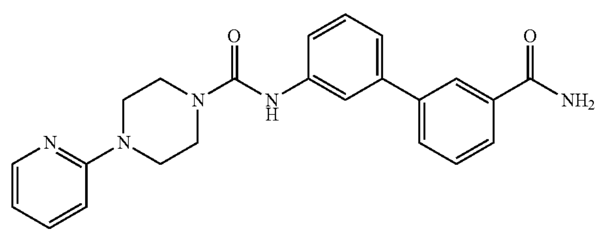 [SMILES: NC(=O)c1cccc(-c2cccc(NC(=O)N3CCN(c4ccccn4)CC3)c2)c1] |
| Example 10 | 4-([1,1'-biphenyl]-4-ylmethyl)-N-(3'-carbamoyl-[1,1'-biphenyl]-3-yl)piperazine-1-carboxamide | 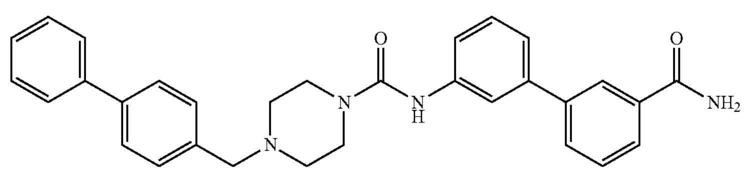 [SMILES: NC(=O)c1cccc(-c2cccc(NC(=O)N3CCN(Cc4ccc(-c5ccccc5)cc4)CC3)c2)c1] |
| Example 11 | N-(3'-carbamoyl-[1,1'-biphenyl]-3-yl)-4-phenylpiperazine-1-carboxamide | 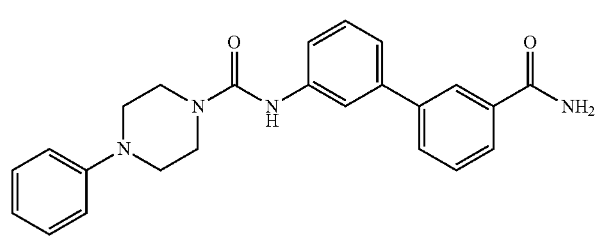 |

-continued

| Example | Name | Structure |
|---|---|---|
| Example 12 | N-(3'-carbamoyl-[1,1'-biphenyl]-3-yl)-4-(quinolin-2-ylmethyl)piperazine-1-carboxamide | 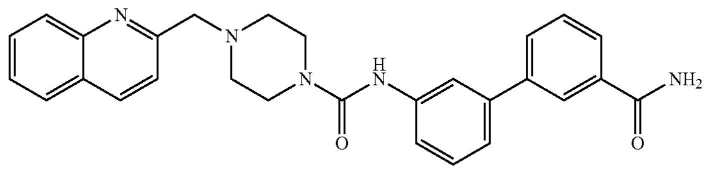 [SMILES: NC(=O)c1cccc(-c2cccc(NC(=O)N3CCN(Cc4ccc5ccccc5n4)CC3)c2)c1] |
| Example 13 | N-(3'-cyano-[1,1'-biphenyl]-3-yl)-4-(quinolin-2-ylmethyl)piperazine-1-carboxamide | 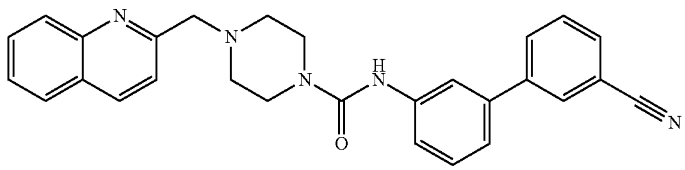 [SMILES: N#Cc1cccc(-c2cccc(NC(=O)N3CCN(Cc4ccc5ccccc5n4)CC3)c2)c1] |
| Example 14 | N-(3-phenoxyphenyl)-4-(quinolin-2-ylmethyl)piperazine-1-carboxamide | 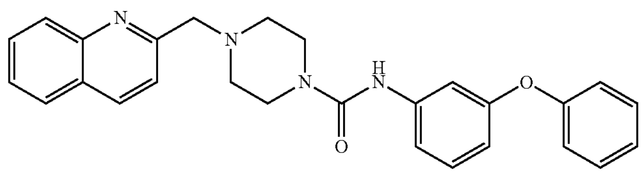 [SMILES: O=C(Nc1cccc(Oc2ccccc2)c1)N1CCN(Cc2ccc3ccccc3n2)CC1] |
| Example 15 | N-(3'-cyano[1,1'-biphenyl]-3-yl)-4-phenylpiperidine-1-carboxamide | 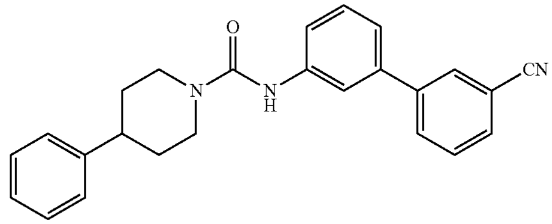 [SMILES: N#Cc1cccc(-c2cccc(NC(=O)N3CCC(c4ccccc4)CC3)c2)c1] |
| Example 16 | N-(5-(3-cyanophenyl)pyridin-3-yl)-4-phenylpiperidine-1-carboxamide | 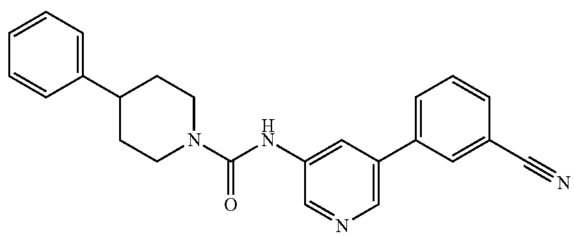 [SMILES: N#Cc1cccc(-c2cncc(NC(=O)N3CCC(c4ccccc4)CC3)c2)c1] |
| Example 17 | 4-([1,1'-biphenyl]-3-ylmethyl)-N-(3'-cyano[1,1'-biphenyl]-3-yl)piperazine-1-carboxamide | 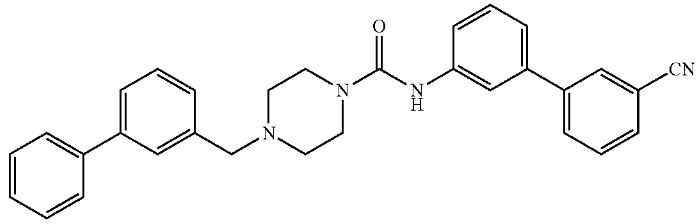 [SMILES: N#Cc1cccc(-c2cccc(NC(=O)N3CCN(Cc4cccc(-c5ccccc5)c4)CC3)c2)c1] |
| Example 18 | N-(3'-carbamoyl-[1,1'-biphenyl]-3-yl)-4-(3-phenoxybenzyl)piperazine-1-carboxamide | 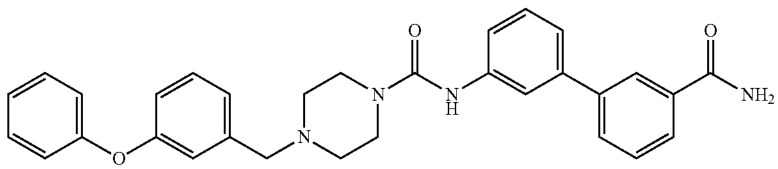 [SMILES: NC(=O)c1cccc(-c2cccc(NC(=O)N3CCN(Cc4cccc(Oc5ccccc5)c4)CC3)c2)c1] |

-continued

| Example | Name | Structure |
|---|---|---|
| Example 19 | (S)-N-(3'-cyano-[1,1'-biphenyl]-3-yl)-3-methyl-4-(quinolin-2-ylmethyl)piperazine-1-carboxamide | 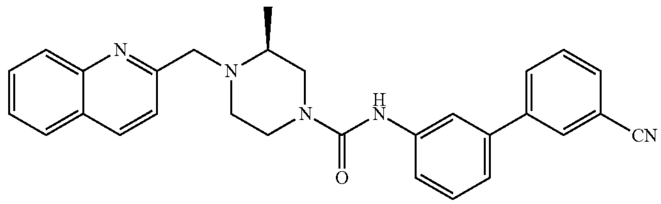 [SMILES: C[C@H]1CN(C(=O)Nc2cccc(-c3cccc(C#N)c3)c2)CCN1Cc1ccc2ccccc2n1] |
| Example 20 | N-(3'-cyano[1,1'-biphenyl]-3-yl)-4-oxospiro[chromane-2,4'-piperidine]-1'-carboxamide | 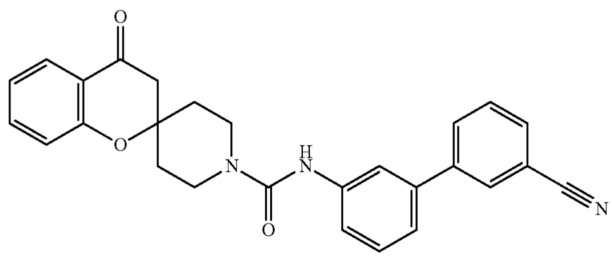 [SMILES: N#Cc1cccc(-c2cccc(NC(=O)N3CCC4(CC3)CC(=O)c3ccccc3O4)c2)c1] |
| Example 21 | (S)-(4-([1,1'-biphenyl]-3-ylmethyl)-3-methylpiperazin-1-yl)(4-phenyl-1H-imidazol-1-yl)methanone | 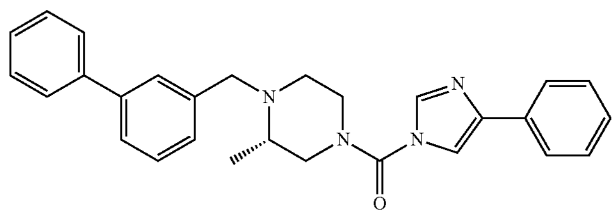 [SMILES: C[C@H]1CN(C(=O)n2cnc(-c3ccccc3)c2)CCN1Cc1cccc(-c2ccccc2)c1] |
| Example 22 | (S)-(4-bromo-1H-imidazol-1-yl)(2-methyl-4-(3-phenoxybenzyl)piperazin-1-yl)methanone | 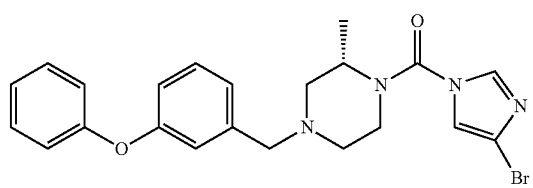 [SMILES: C[C@H]1CN(Cc2cccc(Oc3ccccc3)c2)CCN1C(=O)n1cnc(Br)c1] |
| Example 23 | (2-methyl-4-phenylpiperazin-1-yl)(4-phenyl-1H-imidazol-1-yl)methanone | 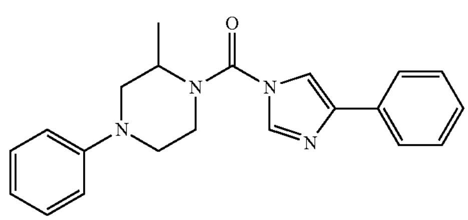 [SMILES: CC1CN(c2ccccc2)CCN1C(=O)n1cnc(-c2ccccc2)c1] |
| Example 24 | (3-methyl-4-phenylpiperazin-1-yl)(4-phenyl-1H-imidazol-1-yl)methanone | 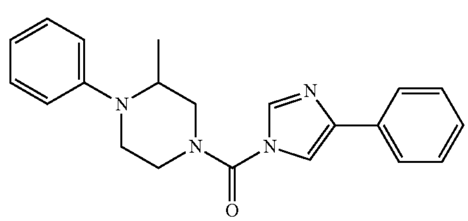 [SMILES: CC1CN(C(=O)n2cnc(-c3ccccc3)c2)CCN1c1ccccc1] |
| Example 25 | (3-methyl-4-(p-tolyl)piperazin-1-yl)(4-phenyl-1H-imidazol-1-yl)methanone | 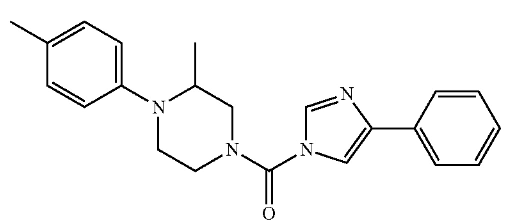 [SMILES: Cc1ccc(N2CCN(C(=O)n3cnc(-c4ccccc4)c3)CC2C)cc1] |

-continued

| Example | Name | Structure |
|---|---|---|
| Example 26 | (4-(3-(benzyloxy)phenyl)-3-methylpiperazin-1-yl)(4-phenyl-1H-imidazol-1-yl)methanone | 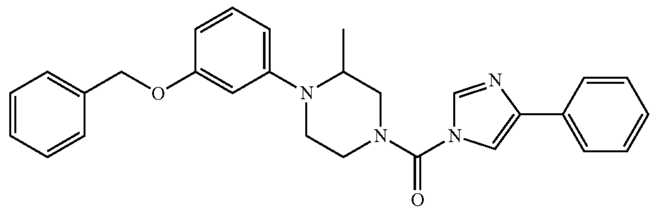 [SMILES: CC1CN(C(=O)n2cnc(-c3ccccc3)c2)CCN1c1cccc(OCc2ccccc2)c1] |
| Example 27 | (4-(3-hydroxyphenyl)-3-methylpiperazin-1-yl)(4-phenyl-1H-imidazol-1-yl)methanone | 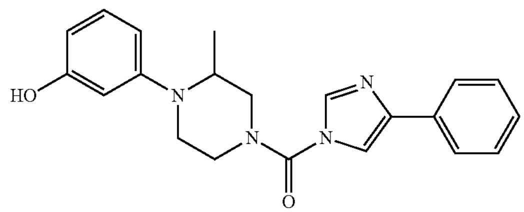 [SMILES: CC1CN(C(=O)n2cnc(-c3ccccc3)c2)CCN1c1cccc(O)c1] |
| Example 28 | (4-(bis(4-fluorophenyl)methyl)piperazin-1-yl)(4-bromo-1H-imidazol-1-yl)methanone | 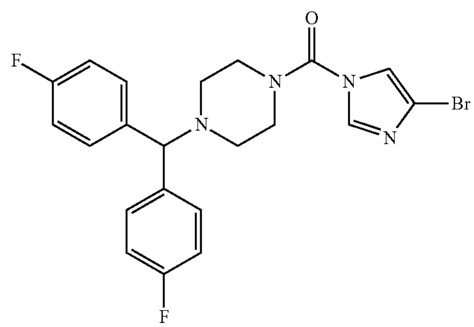 [SMILES: O=C(N1CCN(C(c2ccc(F)cc2)c2ccc(F)cc2)CC1)n1cnc(Br)c1] |
| Example 29 | (4-(bis(4-fluorophenyl)methyl)piperazin-1-yl)(4-phenyl-1H-imidazol-1-yl)methanone | 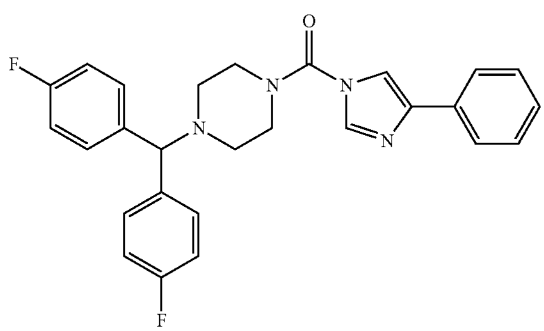 [SMILES: O=C(N1CCN(C(c2ccc(F)cc2)c2ccc(F)cc2)CC1)n1cnc(-c2ccccc2)c1] |
| Example 30 | (4-benzhydrylpiperazin-1-yl)(4-phenyl-1H-imidazol-1-yl)methanone | 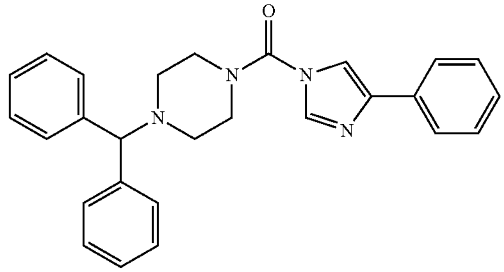 [SMILES: O=C(N1CCN(C(c2ccccc2)c2ccccc2)CC1)n1cnc(-c2ccccc2)c1] |

-continued

| Example | Name | Structure |
| --- | --- | --- |
| Example 31 | (4-benzhydrylpiperazin-1-yl)(5-benzyl-1H-tetrazol-1-yl)methanone | 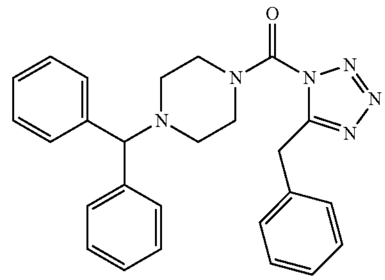 [SMILES: O=C(N1CCN(C(c2ccccc2)c2ccccc2)CC1)n1nnnc1Cc1ccccc1] |
| Example 32 | (5-benzyl-1H-tetrazol-1-yl)(4-(bis(4-fluorophenyl)methyl)piperazin-1-yl)methanone | 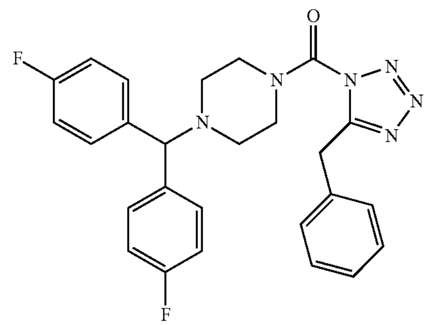 [SMILES: O=C(N1CCN(C(c2ccc(F)cc2)c2ccc(F)cc2)CC1)n1nnnc1Cc1ccccc1] |
| Example 33 | (3-(Carbomethoxy)-1H-1,2,4-triazol-1-yl)(4-(bis(4-fluorophenyl)methyoxy)piperidin-1-yl)methanone | 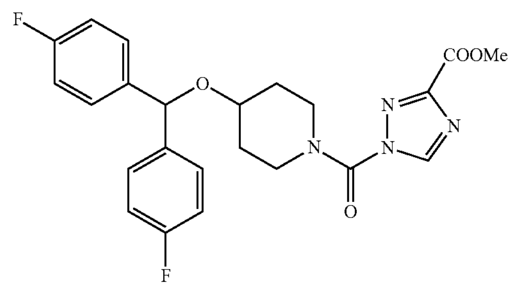 [SMILES: COC(=O)c1ncn(C(=O)N2CCC(OC(c3ccc(F)cc3)c3ccc(F)cc3)CC2)n1] |
| Example 34 | 4'-(4-bromo-1H-imidazole-1-carbonyl)spiro[chromane-2,1'-cyclohexan]-4-one | 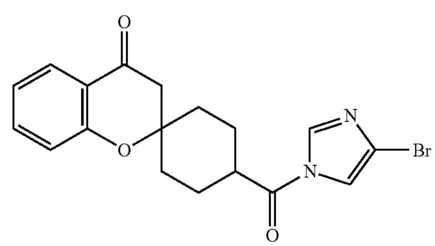 [SMILES: O=C1CC2(CCC(C(=O)n3cnc(Br)c3)CC2)Oc2ccccc21] |
| Example 35 | 3-Cyanophenyl 4-(2-methyl-1-phenylpropyl)piperazine-1-carboxylate | 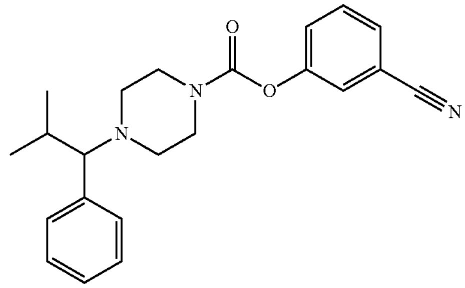 [SMILES: CC(C)C(c1ccccc1)N1CCN(C(=O)Oc2cccc(C#N)c2)CC1] |

-continued

| Example | Name |
|---|---|
| Example 36 | 3-cyanophenyl 4-(1-phenylethyl)piperazine-1-carboxylate |
| Example 37 | 3-cyanophenyl 4-(cyclopentyl(phenyl)methyl)piperazine-1-carboxylate |
| Example 38 | 3-cyano-5-hydroxyphenyl 4-benzhydrylpiperazine-1-carboxylate |
| Example 39 | 6-chloropyridin-2-yl 4-benzhydrylpiperazine-1-carboxylate |
| Example 40 | 3-cyanophenyl 4-(bis(4-fluorophenyl)methyl)piperazine-1-carboxylate |

-continued

| Example | Name | Structure |
|---|---|---|
| Example 41 | 3-cyanophenyl 4-(9H-fluoren-9-yl)piperazine-1-carboxylate | 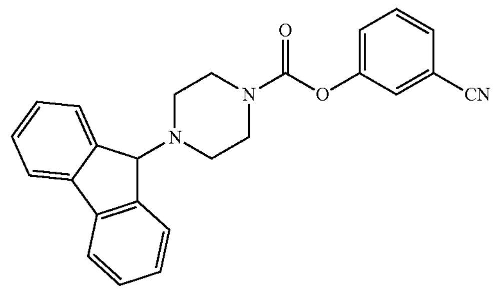 [SMILES: N#Cc1cccc(OC(=O)N2CCN(C3c4ccccc4-c4ccccc43)CC2)c1] |
| Example 42 | 4-cyanopyridin-2-yl 4-(9H-fluoren-9-yl)piperazine-1-carboxylate | 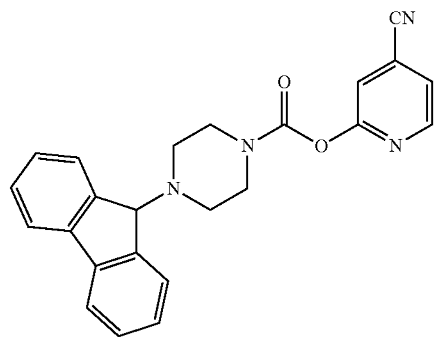 [SMILES: N#Cc1ccnc(OC(=O)N2CCN(C3c4ccccc4-c4ccccc43)CC2)c1] |
| Example 43 | 3-cyanopyridin-2-yl 4-(9H-fluoren-9-yl)piperazine-1-carboxylate | 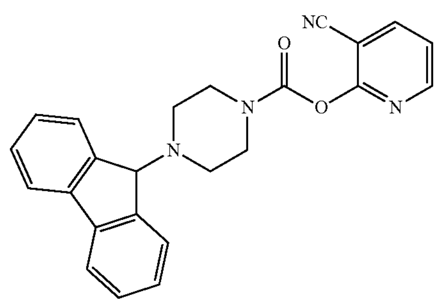 [SMILES: N#Cc1cccnc1OC(=O)N1CCN(C2c3ccccc3-c3ccccc32)CC1] |
| Example 44 | 3-Cyanophenyl 4-benzhydryl piperazine-1-carboxylate | 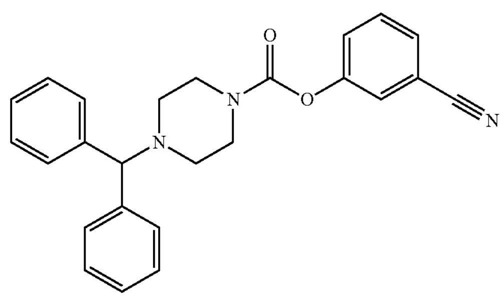 [SMILES: N#Cc1cccc(OC(=O)N2CCN(C(c3ccccc3)c3ccccc3)CC2)c1] |
| Example 45 | 5-Cyano-2-fluorophenyl 4-benzylpiperidine-1-carboxylate | 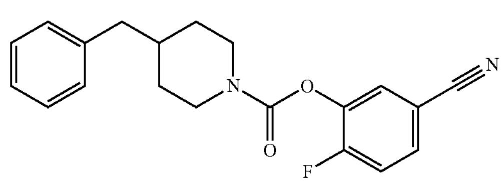 [SMILES: N#Cc1ccc(F)c(OC(=O)N2CCC(Cc3ccccc3)CC2)c1] |

-continued

| Example | Name | Structure |
|---|---|---|
| Example 46 | 3-Cyanophenyl 4-benzhydrylpiperidine-1-carboxylate | 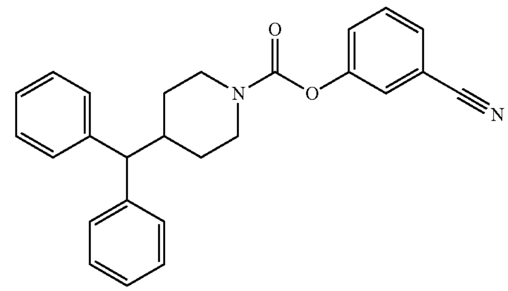 [SMILES: N#Cc1cccc(OC(=O)N2CCC(C(c3ccccc3)c3ccccc3)CC2)c1] |
| Example 47 | 3-cyanophenyl 4-(diphenylmethylene)piperidine-1-carboxylate | 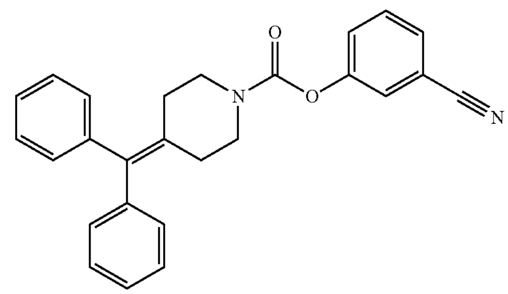 [SMILES: N#Cc1cccc(OC(=O)N2CCC(=C(c3ccccc3)c3ccccc3)CC2)c1] |
| Example 48 | 3-(methoxycarbonyl)phenyl 4-(diphenylmethylene)piperidine-1-carboxylate | 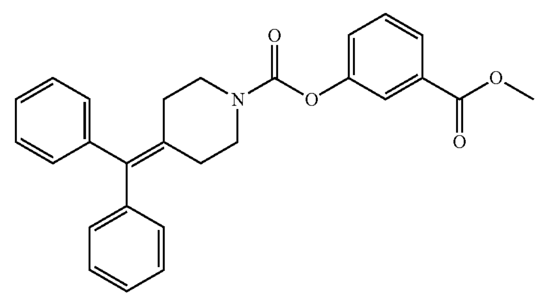 [SMILES: COC(=O)c1cccc(OC(=O)N2CCC(=C(c3ccccc3)c3ccccc3)CC2)c1] |
| Example 49 | 5-cyano-2-fluorophenyl 4-benzhydrylpiperidine-1-carboxylate | 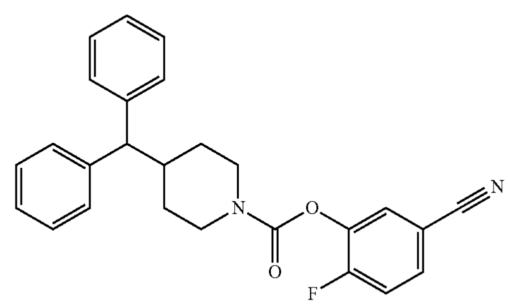 [SMILES: N#Cc1ccc(F)c(OC(=O)N2CCC(C(c3ccccc3)c3ccccc3)CC2)c1] |
| Example 50 | 3-cyano-5-hydroxyphenyl 4-benzhydrylpiperidine-1-carboxylate | 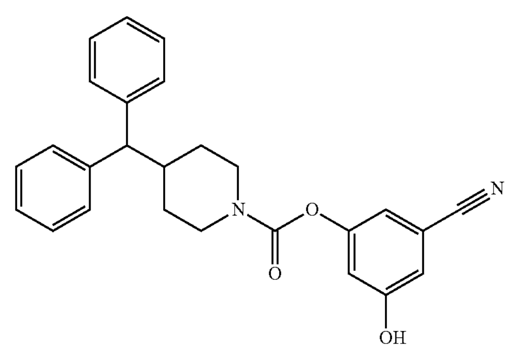 [SMILES: N#Cc1cc(O)cc(OC(=O)N2CCC(C(c3ccccc3)c3ccccc3)CC2)c1] |

-continued

| Example | Name | Structure |
|---|---|---|
| Example 51 | 6-Chloropyridin-2-yl 4-(benzhydryl)piperidine-1-carboxylate | 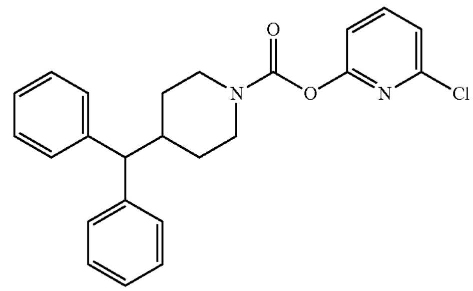 [SMILES: O=C(Oc1cccc(Cl)n1)N1CCC(C(c2ccccc2)c2ccccc2)CC1] |
| Example 52 | 3-cyanophenyl 4-benzylpiperidine-1-carboxylate | 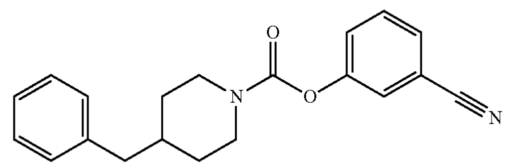 [SMILES: N#Cc1cccc(OC(=O)N2CCC(Cc3ccccc3)CC2)c1] |
| Example 53 | 3-cyanophenyl 4-((4-chlorophenyl)(2-chloropyridin-3-yl)methoxy)piperidine-1-carboxylate | 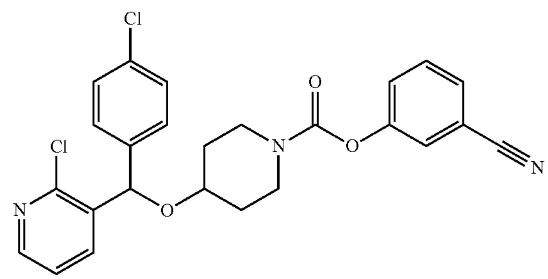 [SMILES: N#Cc1cccc(OC(=O)N2CCC(OC(c3ccc(Cl)cc3)c3cccnc3Cl)CC2)c1] |
| Example 54 | 6-Chloropyridin-2-yl 4-(benzhydryl)piperidine-1-carboxylate | 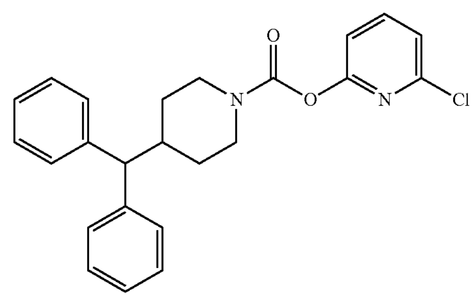 [SMILES: O=C(Oc1cccc(Cl)n1)N1CCC(C(c2ccccc2)c2ccccc2)CC1] |
| Example 55 | 3-(methoxycarbonyl)phenyl 4-(benzhydryloxy)piperidine-1-carboxylate | 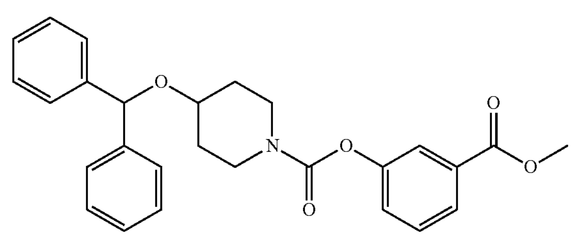 [SMILES: COC(=O)c1cccc(OC(=O)N2CCC(OC(c3ccccc3)c3ccccc3)CC2)c1] |
| Example 56 | 5-cyano-2-fluorophenyl 4-(benzhydryloxy)piperidine-1-carboxylate | 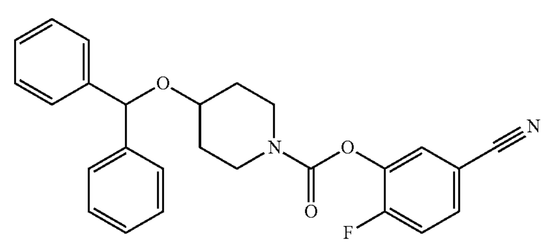 [SMILES: N#Cc1ccc(F)c(OC(=O)N2CCC(OC(c3ccccc3)c3ccccc3)CC2)c1] |

-continued

| Example | Name | Structure |
|---|---|---|
| Example 57 | 6-chloropyridin-2-yl 4-(benzhydryloxy)piperidine-1-carboxylate | 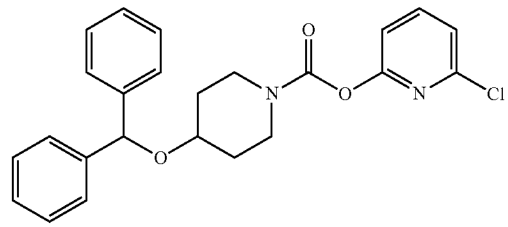 [SMILES: O=C(Oc1cccc(Cl)n1)N1CCC(OC(c2ccccc2)c2ccccc2)CC1] |
| Example 58 | 3-cyanophenyl 4-(benzhydryloxy)piperidine-1-carboxylate | 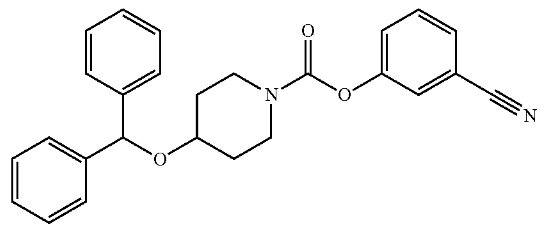 [SMILES: N#Cc1cccc(OC(=O)N2CCC(OC(c3ccccc3)c3ccccc3)CC2)c1] |
| Example 59 | 3-Cyanophenyl 4-(4-bromophenylsulfonyl)piperidine-1-carboxylate | 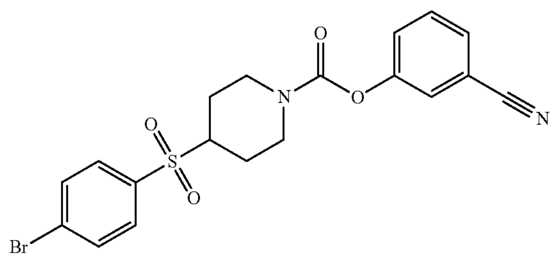 [SMILES: N#Cc1cccc(OC(=O)N2CCC(S(=O)(=O)c3ccc(Br)cc3)CC2)c1] |
| Example 60 | 5-Cyano-2-fluorophenyl 4-(4-bromophenylsulfonyl)piperidine-1-carboxylate | 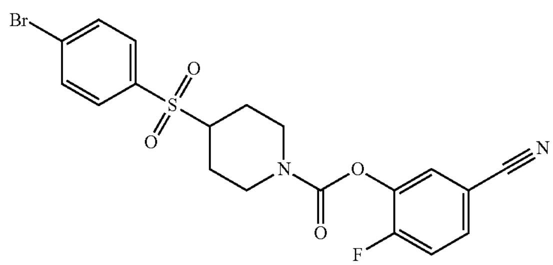 [SMILES: N#Cc1ccc(F)c(OC(=O)N2CCC(S(=O)(=O)c3ccc(Br)cc3)CC2)c1] |
| Example 61 | 5-Cyano-2-methylphenyl 4-(4-bromophenylsulfonyl)piperidine-1-carboxylate | 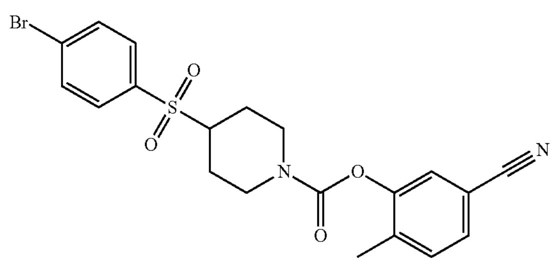 [SMILES: Cc1ccc(C#N)cc1OC(=O)N1CCC(S(=O)(=O)c2ccc(Br)cc2)CC1] |
| Example 62 | 5-Cyano-2-methoxyphenyl 4-(4-bromophenylsulfonyl)piperidine-1-carboxylate | 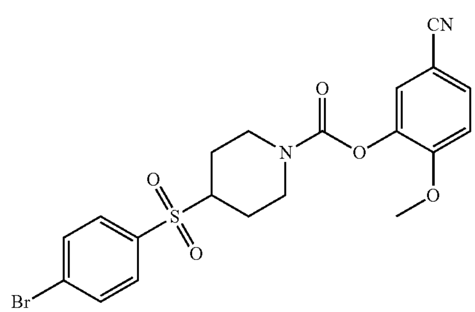 [SMILES: COc1ccc(C#N)cc1OC(=O)N1CCC(S(=O)(=O)c2ccc(Br)cc2)CC1] |

-continued

| Example | Name | Structure |
|---|---|---|
| Example 63 | 2,6-Difluorophenyl 4-(4-bromophenylsulfonyl)piperidine-1-carboxylate | 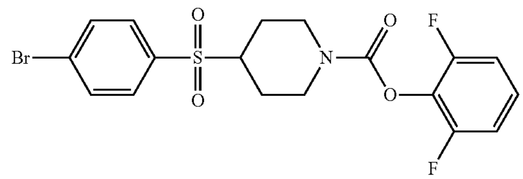 [SMILES: O=C(Oc1c(F)cccc1F)N1CCC(S(=O)(=O)c2ccc(Br)cc2)CC1] |
| Example 64 | 4-bromophenyl 4-tosylpiperazine-1-carboxylate | 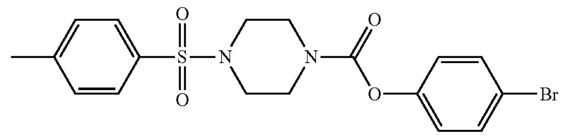 [SMILES: Cc1ccc(S(=O)(=O)N2CCN(C(=O)Oc3ccc(Br)cc3)CC2)cc1] |
| Example 65 | 2,6-difluorophenyl 4-tosylpiperazine-1-carboxylate | 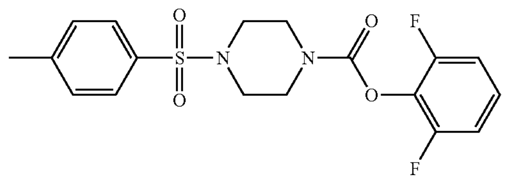 [SMILES: Cc1ccc(S(=O)(=O)N2CCN(C(=O)Oc3c(F)cccc3F)CC2)cc1] |
| Example 66 | 4'-fluoro-3-hydroxy-[1,1'-biphenyl]-4-yl 4-tosylpiperazine-1-carboxylate | 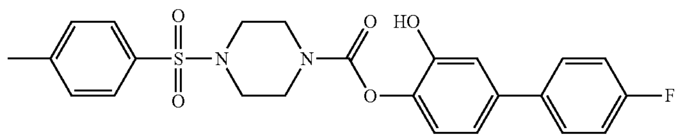 [SMILES: Cc1ccc(S(=O)(=O)N2CCN(C(=O)Oc3ccc(-c4ccc(F)cc4)cc3O)CC2)cc1] |
| Example 67 | N-(3-(1,1-dioxidothiomorpholino)phenyl)-4-phenylpiperazine-1-carboxamide | 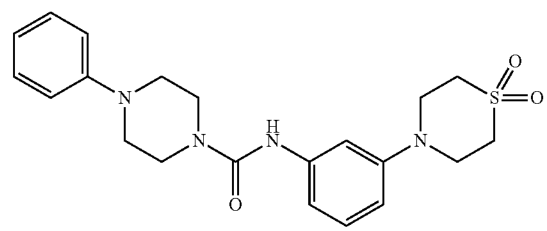 [SMILES: O=C(Nc1cccc(N2CCS(=O)(=O)CC2)c1)N1CCN(c2ccccc2)CC1] |
| Example 68 | N-(3-(1,1-dioxidothiomorpholino)phenyl)-4-phenylpiperidine-1-carboxamide | 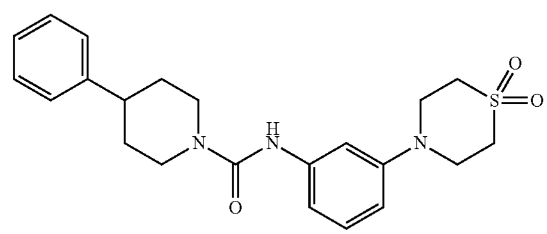 [SMILES: O=C(Nc1cccc(N2CCS(=O)(=O)CC2)c1)N1CCC(c2ccccc2)CC1] |
| Example 69 | 3-(1,1-dioxidothiomorpholino)phenyl 4-phenylpiperazine-1-carboxylate | 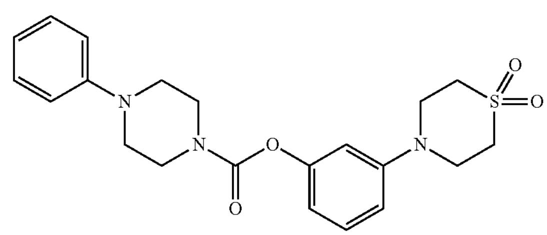 [SMILES: O=C(Oc1cccc(N2CCS(=O)(=O)CC2)c1)N1CCN(c2ccccc2)CC1] |
| Example 70 | 3-(1,1-Dioxothiomorpholin-4-yl)phenyl 4-phenylpiperidine-1-carboxylate | 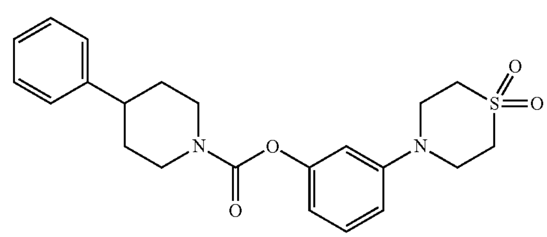 [SMILES: O=C(Oc1cccc(N2CCS(=O)(=O)CC2)c1)N1CCC(c2ccccc2)CC1] |

-continued

| Example | Name | Structure |
|---|---|---|
| Example 71 | 3-(1,1-dioxidothiomorpholino)phenyl 4-(3-phenoxybenzyl)piperazine-1-carboxylate | 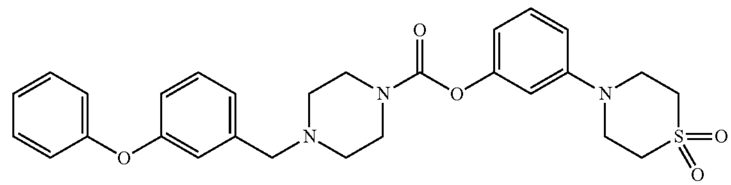 [SMILES: O=C(Oc1cccc(N2CCS(=O)(=O)CC2)c1)N1CCN(Cc2cccc(Oc3ccccc3)c2)CC1] |
| Example 72 | 3-(1,1-dioxidothiomorpholino)phenyl 4-(quinolin-2-ylmethyl)piperazine-1-carboxylate | 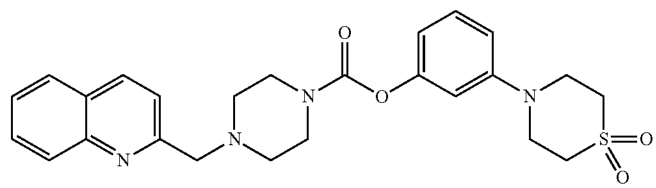 [SMILES: O=C(Oc1cccc(N2CCS(=O)(=O)CC2)c1)N1CCN(Cc2ccc3ccccc3n2)CC1] |
| Example 73 | 3-(1,1-dioxidothiomorpholino)phenyl 2-methyl-4-phenylpiperazine-1-carboxylate | 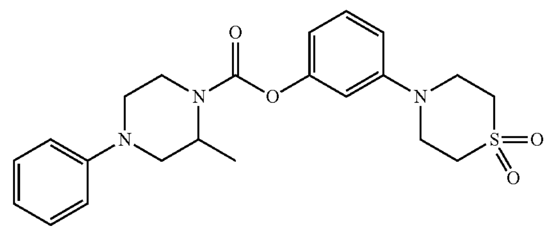 [SMILES: CC1CN(c2ccccc2)CCN1C(=O)Oc1cccc(N2CCS(=O)(=O)CC2)c1] |
| Example 74 | 3-Cyanophenyl 3-(4-chlorobenzyloxy)azetidine-1-carboxylate | 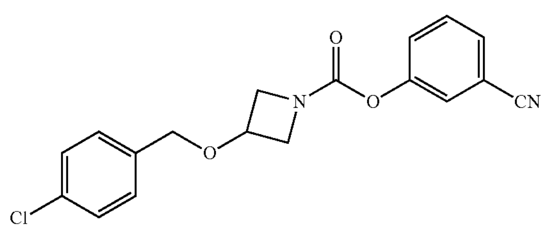 [SMILES: N#Cc1cccc(OC(=O)N2CC(OCc3ccc(Cl)cc3)C2)c1] |
| Example 75 | 3-(Trifluoromethyl)phenyl 3-(4-chlorobenzyloxy)azetidine-1-carboxylate | 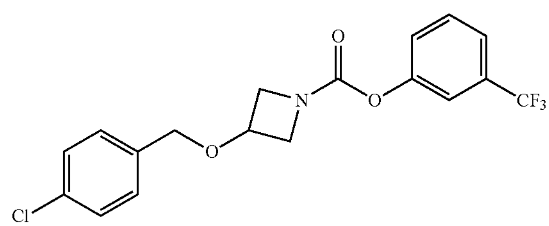 [SMILES: O=C(Oc1cccc(C(F)(F)F)c1)N1CC(OCc2ccc(Cl)cc2)C1] |
| Example 76 | 3-Bromophenyl 3-(4-chlorobenzyloxy)azetidine-1-carboxylate | 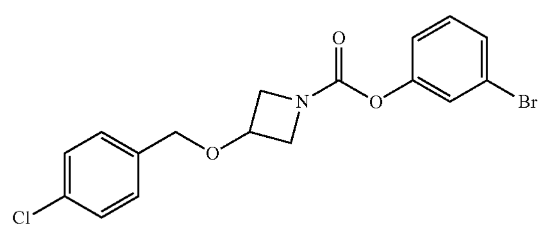 [SMILES: O=C(Oc1cccc(Br)c1)N1CC(OCc2ccc(Cl)cc2)C1] |
| Example 77 | 3-Carbamoylphenyl 3-(4-chlorobenzyloxy)azetidine-1-carboxylate | 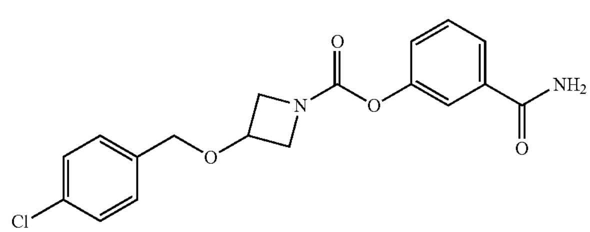 [SMILES: NC(=O)c1cccc(OC(=O)N2CC(OCc3ccc(Cl)cc3)C2)c1] |

-continued

| Example | Name | Structure |
|---|---|---|
| Example 78 | 3-Methoxyphenyl 3-(4-Bromobenzyloxy)azetidine-1-carboxylate | 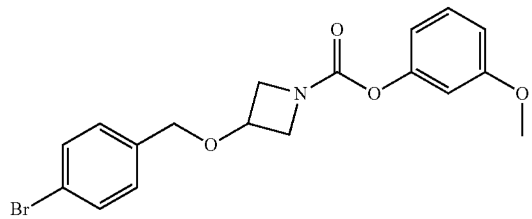 [SMILES: COc1cccc(OC(=O)N2CC(OCc3ccc(Br)cc3)C2)c1] |
| Example 79 | 2,4-Dichlorophenyl 3-(4-chlorobenzyloxy)azetidine-1-carboxylate | 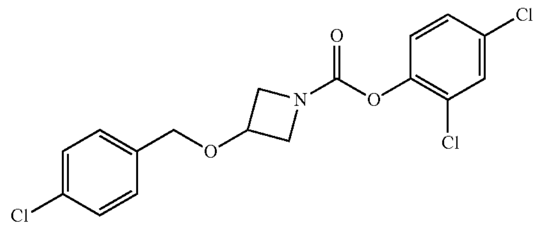 [SMILES: O=C(Oc1ccc(Cl)cc1Cl)N1CC(OCc2ccc(Cl)cc2)C1] |
| Example 80 | 3-(Pyridin-3-yl)phenyl 3-(4-chlorobenzyloxy)azetidine-1-carboxylate | 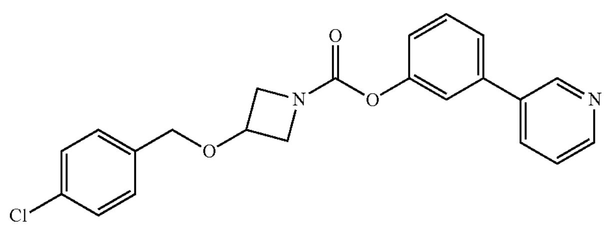 [SMILES: O=C(Oc1cccc(-c2cccnc2)c1)N1CC(OCc2ccc(Cl)cc2)C1] |
| Example 81 | 3-(4-Chlorobenzyloxy)-N-phenylazetidine-1-carboxamide | 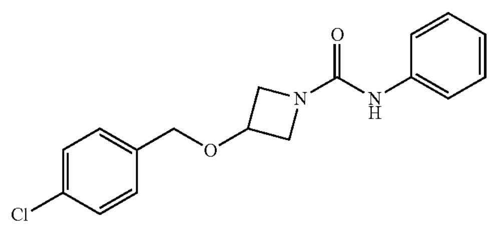 [SMILES: O=C(Nc1ccccc1)N1CC(OCc2ccc(Cl)cc2)C1] |
| Example 82 | 3-(4-Bromobenzyloxy)-N-(pyridin-3-yl)azetidine-1-carboxamide | 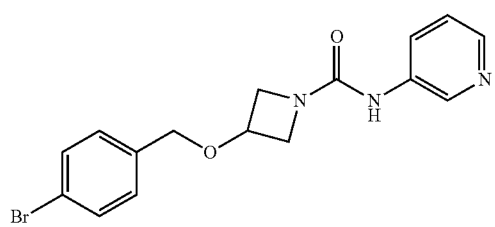 [SMILES: O=C(Nc1cccnc1)N1CC(OCc2ccc(Br)cc2)C1] |
| Example 83 | (1H-Benzo[d]imidazol-1-yl)(3-(4-phenylpiperidin-1-yl)azetidin-1-yl)methanone | 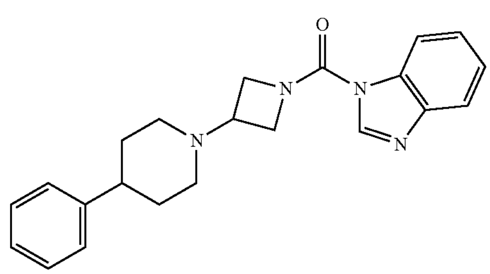 [SMILES: O=C(N1CC(N2CCC(c3ccccc3)CC2)C1)n1cnc2ccccc21] |

-continued

| Example | Name | Structure |
|---|---|---|
| Example 84 | (3-(4-Benzylpiperidine)azetidin-1-yl)(4-phenyl[1H]imidazol-1-yl)methanone | 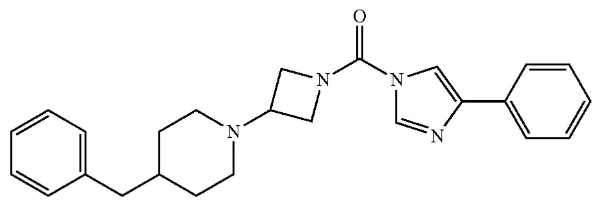 [SMILES: O=C(N1CC(N2CCC(Cc3ccccc3)CC2)C1)n1cnc(-c2ccccc2)c1] |
| Example 85 | (4-Phenyl-1H-imidazol-1-yl)(3-(4-phenylpiperidin-1-yl)azetidin-1-yl)methanone | 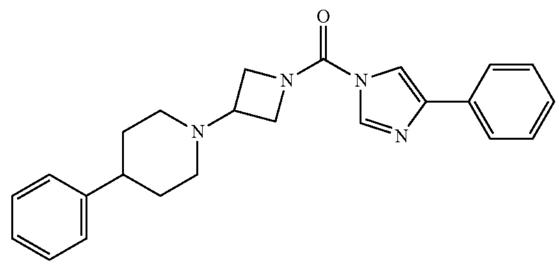 [SMILES: O=C(N1CC(N2CCC(c3ccccc3)CC2)C1)n1cnc(-c2ccccc2)c1] |
| Example 86 | (3-(4-Bromobenzyloxy)azetidin-1-yl)(4-phenyl-1H-imidazol-1-yl)methanone | 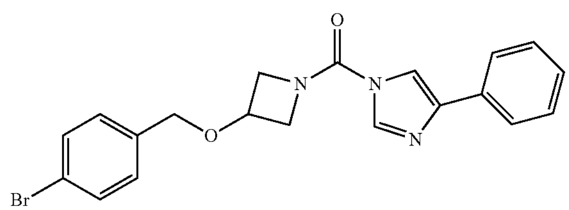 [SMILES: O=C(N1CC(OCc2ccc(Br)cc2)C1)n1cnc(-c2ccccc2)c1] |
| Example 87 | (1H-Benzo[d]imidazol-1-yl)(3-(4-Bromobenzyloxy)azetidin-1-yl)methanone | 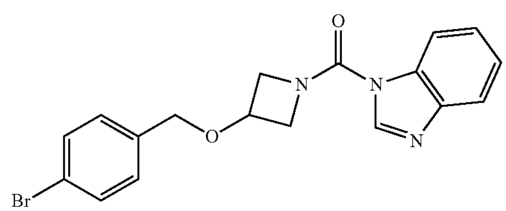 [SMILES: O=C(N1CC(OCc2ccc(Br)cc2)C1)n1cnc2ccccc21] |
| Example 88 | 3-(4-Bromobenzyloxy)azetidin-1-yl](piperidin-1-yl)methanone | 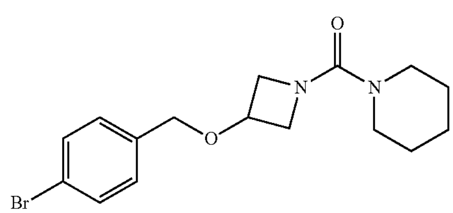 [SMILES: O=C(N1CCCCC1)N1CC(OCc2ccc(Br)cc2)C1] |
| Example 89 | (3-(4-Phenylpiperidin-1-yl)azetidin-1-yl)(1H-pyrazol-1-yl)methanone | 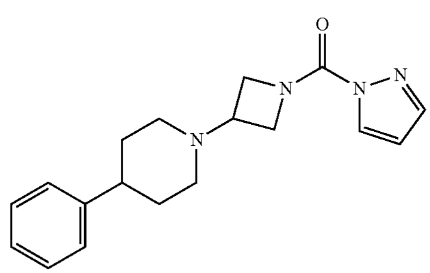 [SMILES: O=C(N1CC(N2CCC(c3ccccc3)CC2)C1)n1cccn1] |

-continued

| Example | Name | Structure |
|---|---|---|
| Example 90 | 3-(4-Phenylpiperidin-1-yl)azetidin-1-yl)(1H-1,2,4-triazol-1-yl)methanone | 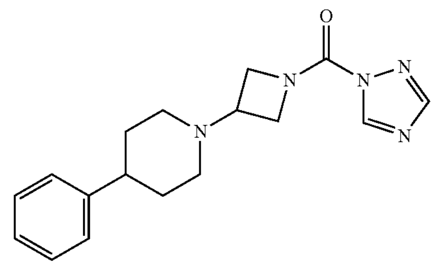 [SMILES: O=C(N1CC(N2CCC(c3ccccc3)CC2)C1)n1cncn1] |
| Example 91 | 3-(4-Bromophenylthio)azetidin-1-yl)(1H-1,2,4-triazol-1-yl)methanone | 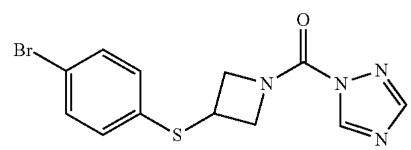 [SMILES: O=C(N1CC(Sc2ccc(Br)cc2)C1)n1cncn1] |
| Example 92 | (1S,4S)-N-(3'-carbamoyl-[1,1'-biphenyl]-3-yl)-5-(quinolin-2-ylmethyl)-2,5-diazabicyclo[2.2.1]heptane-2-carboxamide | 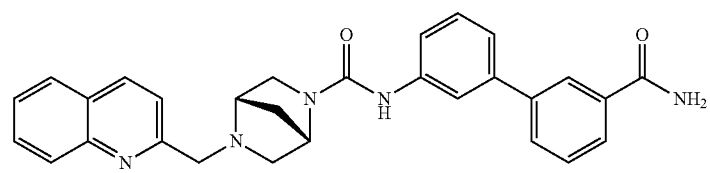 [SMILES: NC(=O)c1cccc(-c2cccc(NC(=O)N3C[C@@H]4C[C@H]3CN4Cc3ccc4ccccc4n3)c2)c1] |
| Example 93 | (1S,4S)-N-(3'-cyano-[1,1'-biphenyl]-3-yl)-5-(quinolin-2-ylmethyl)-2,5-diazabicyclo[2.2.1]heptane-2-carboxamide | 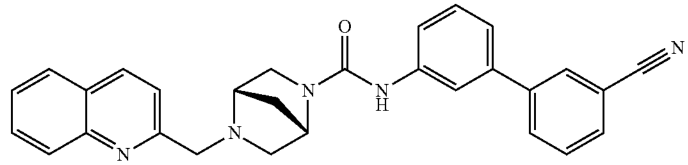 [SMILES: N#Cc1cccc(-c2cccc(NC(=O)N3C[C@@H]4C[C@H]3CN4Cc3ccc4ccccc4n3)c2)c1] |
| Example 94 | (1S,4S)-5-([1,1'-biphenyl]-3-ylmethyl)-N-(3'-cyano-[1,1'-biphenyl]-3-yl)-2,5-diazabicyclo[2.2.1]heptane-2-carboxamide | 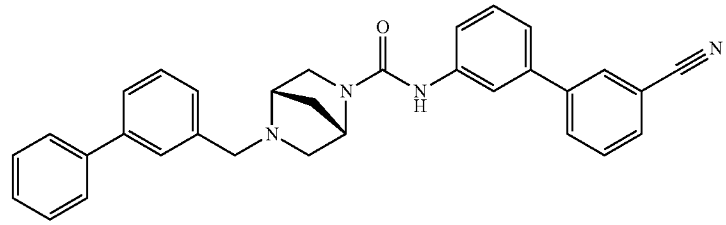 [SMILES: N#Cc1cccc(-c2cccc(NC(=O)N3C[C@@H]4C[C@H]3CN4Cc3cccc(-c4ccccc4)c3)c2)c1] |
| Example 95 | (1S,4S)-N-(3-bromophenyl)-5-(quinolin-2-ylmethyl)-2,5-diazabicyclo[2.2.1]heptane-2-carboxamide | 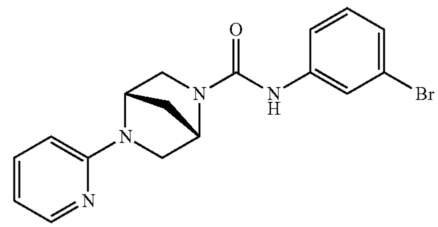 [SMILES: O=C(Nc1cccc(Br)c1)N1C[C@@H]2C[C@H]1CN2c1ccccn1] |
| Example 96 | (4-phenyl-1H-imidazol-1-yl)((1S,4S)-5-(pyridin-2-yl)-2,5-diazabicyclo[2.2.1]heptan-2-yl)methanone | 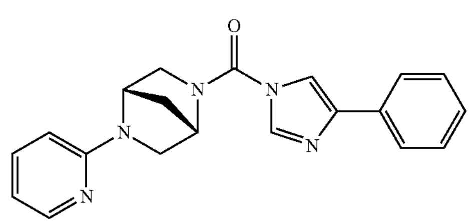 [SMILES: O=C(N1C[C@@H]2C[C@H]1CN2c1ccccn1)n1cnc(-c2ccccc2)c1] |

| Example | Name | Structure |
|---|---|---|
| Example 97 | ((1S,4S)-5-(3-fluorophenyl)-2,5-diazabicyclo[2.2.1]heptan-2-yl)(4-phenyl-1H-imidazol-1-yl)methanone | 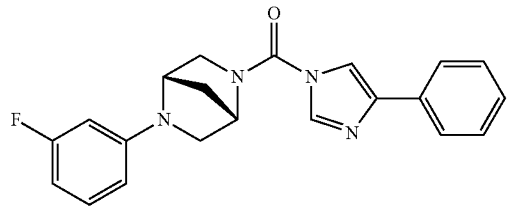 [SMILES: O=C(N1C[C@@H]2C[C@H]1CN2c1cccc(F)c1)n1cnc(-c2ccccc2)c1] |
| Example 98 | ((1S,4S)-5-(3-(benzyloxy)phenyl)-2,5-diazabicyclo[2.2.1]heptan-2-yl)(4-phenyl-1H-imidazol-1-yl)methanone | 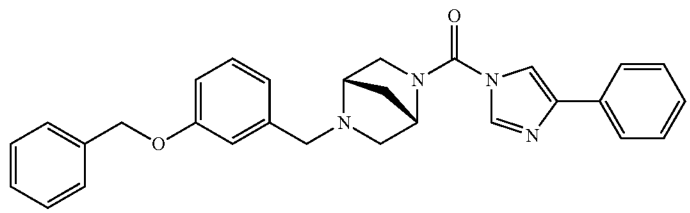 [SMILES: O=C(N1C[C@@H]2C[C@H]1CN2Cc1cccc(OCc2ccccc2)c1)n1cnc(-c2ccccc2)c1] |
| Example 99 | ((1S,4S)-5-([1,1'-biphenyl]-3-ylmethyl)-2,5-diazabicyclo[2.2.1]heptan-2-yl)(4-phenyl-1H-imidazol-1-yl)methanone | 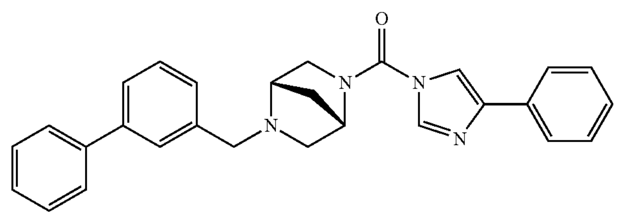 [SMILES: O=C(N1C[C@@H]2C[C@H]1CN2Cc1cccc(-c2ccccc2)c1)n1cnc(-c2ccccc2)c1] |
| Example 100 | ((1S,4S)-5-([1,1'-biphenyl]-3-ylmethyl)-2,5-diazabicyclo[2.2.1]heptan-2-yl)(4-bromo-1H-imdiazol-1-yl)methanone | 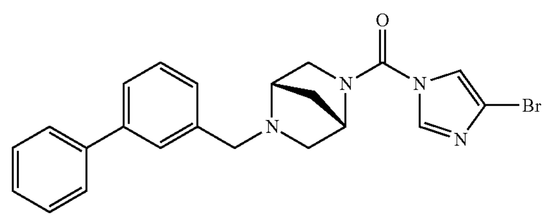 [SMILES: O=C(N1C[C@@H]2C[C@H]1CN2Cc1cccc(-c2ccccc2)c1)n1cnc(Br)c1] |
| Example 101 | phenyl (1S,4S)-5-([1,1'-biphenyl]-3-ylmethyl)-2,5-diazabicyclo[2.2.1]heptane-2-carboxylate | 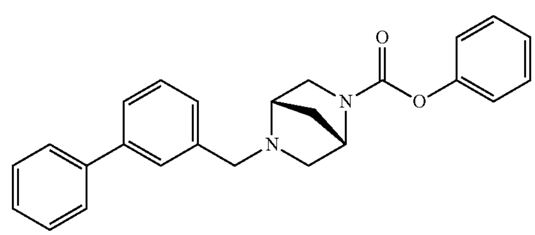 [SMILES: O=C(Oc1ccccc1)N1C[C@@H]2C[C@H]1CN2Cc1cccc(-c2ccccc2)c1] |

We have studied compounds of Example 1, 7, 46, and 52 in vivo

Compounds 1, 7, and 52 were examined for blood-brain distribution parameters according to the assay described below.

Example 110: Blood Brain Barrier (BBB) Permeability Studies

Novel compounds were studied for their abilities to cross the blood brain barrier based on procedures adapted from Cluny, et al (2010), *British journal of pharmacology* 161: 629; Rahn, et al (2011) *Pharmacology, biochemistry, and behavior* 98: 493; Wood et al (2013) *Life sciences* 92: 482.

For example, compounds 1, 7, and 52 have brain/plasma ratio of 0.03, 0.17 and 0.71, respectively.

Example 111: Anticipatory Nausea Studies

Novel compounds were studied for their ability to ameliorate LiCl-induced anticipatory nausea in rats following the procedures described in Limebeer, C. L. et al *Psychopharmacology* (2014) 231:603-612. For example compounds 46 (20 mg/Kg) and 52 (20 mg/Kg) ameliorated anticipatory nausea in rats. Mean number of gapes elicited by a LiCl-paired context in an aniticpatory nausea test following pretreatment with a MAGL inhibitor compound 46 and dual FAAH/MAGL inhibitor 52 were 8 and 3 respectively, compared to animals treated with vehicle which show 22 gapes.

Example 112: Xenograft Model of Advanced Prostate Cancer

Compounds were studied for their abilities to retard tumor growth in mouse xenograft model expressing aggressive human prostate cancer PC-3M cells. Tumors were established in immunodeficient nude mice (Taconic Farms) according to standard protocol and mice were divided in two groups. Mouse in each group was injected intraperitoneally (i.p.) with vehicle or compounds (20 mg/kg daily) for 21 days, Tumor sizes were measured with callipers every 3 days. For example, animals treated with compound 46 showed a 43% reduction in tumor sizes (105 mm$^3$) compared to animals treated with vehicle (185 mm$^3$).

As will be apparent to one of ordinary skill in the art from a reading of this disclosure, the disclosed subject matter can be embodied in forms other than those specifically disclosed above. The particular embodiments described above are, therefore, to be considered as illustrative and not restrictive. Those skilled in the art will recognize, or be able to ascertain, using no more than routine experimentation, numerous equivalents to the specific embodiments described herein. The scope of the invention is as set forth in the appended claims and equivalents thereof, rather than being limited to the examples contained in the foregoing description.

What is claimed is:

1. A compound of Formula II

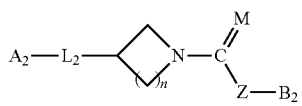

or a pharmaceutically acceptable salt thereof, wherein:
M=O;
Z=O or NH;
n=1;
$L_2$ is selected from

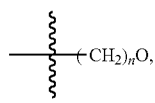

—CH=CH—, —CONH—,

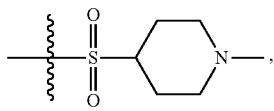

and —NH—, n=1;

$A_2$ is phenyl, which may be unsubstituted or substituted with one or two halogens; and $B_2$ is selected from phenyl, pyrrolyl, pyrazolyl, imidazolyl, pyridinyl, purinyl, benzimidazolyl, indolyl, quinolinyl or quinoxalinyl, and may be unsubstituted or substituted with one or two moieties selected from halogen, —CN, —CONH$_2$ and —CF$_3$, or $B_2$ is selected from:

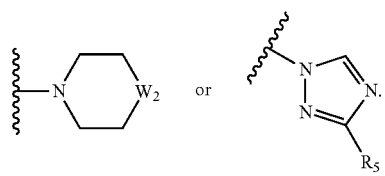

wherein:
$W_2$ is selected from CH$_2$, O, SO$_2$, CHAr and NAr;
Ar is aryl or heteroaryl containing 1 to 3 heteroatoms; and
$R_5$ is selected from —H, -Ph and —COOMe.

2. A compound selected from the group consisting of:
3-Cyanophenyl 3-(4-chlorobenzyloxy)azetidine-1-carboxylate,
3-(Trifluoromethyl)phenyl 3-(4-chlorobenzyloxy)azetidine-1-carboxylate,
3-Bromophenyl 3-(4-chlorobenzyloxy)azetidine-1-carboxylate,
3-Carbamoylphenyl 3-(4-chlorobenzyloxy)azetidine-1-carboxylate,
3-Methoxyphenyl 3-(4-Bromobenzyloxy)azetidine-1-carboxylate,
2,4-Dichlorophenyl 3-(4-chlorobenzyloxy)azetidine-1-carboxylate,
3-(Pyridin-3-yl)phenyl 3-(4-chlorobenzyloxy)azetidine-1-carboxylate,
1H-Benzo[d]imidazol-1-yl)(3-(4-phenylpiperidin-1-yl)azetidin-1-yl)methanone,
3-(4-Benzylpiperidine)azetidin-1-yl)(4-phenyl[1H]imizadol-1-yl)methanone,
4-Phenyl-1H-imidazol-1-yl)(3-(4-phenylpiperidin-1-yl)azetidin-1-yl)methanone,
3-(4-Bromobenzyloxy)azetidin-1-yl)(4-phenyl-1H-imidazol-1-yl)methanone, and
1H-Benzo[d]imidazol-1-yl)(3-(4-Bromobenzyloxy)azetidin-1-yl)methanone,
or a pharmaceutically acceptable salt of any of the foregoing.

3. A pharmaceutical composition comprising a pharmaceutically acceptable carrier and an effective amount of a compound of claim 1, or a pharmaceutically acceptable salt thereof.

4. The compound of claim 2, wherein the compound is 3-cyanophenyl 3-(4-chlorobenzyloxy)azetidine-1-carboxylate, or a pharmaceutically acceptable salt thereof.

5. The compound of claim 2, wherein the compound is 1H-benzo[d]imidazol-1-yl)(3-(4-bromobenzyloxy)azetidin-1-yl)methanone, or a pharmaceutically acceptable salt thereof.

6. A compound of Formula II

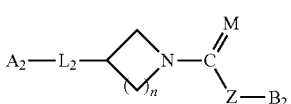

or a pharmaceutically acceptable salt thereof, wherein:
M=O;
Z=O, NH, or none; when Z=none, $B_2$ is directly attached to C=M;
n=1;

L₂ is selected from

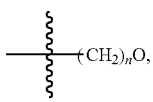

—CH=CH—, —CONH—,

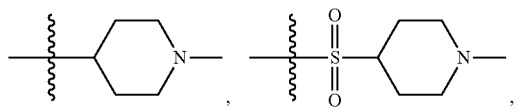

and —NH—, n=1;

A₂ is phenyl, which may be unsubstituted or substituted with one or two halogens; and B₂ is selected from pyrrolyl, pyrazolyl, imidazolyl, purinyl, benzimidazolyl or quinoxalinyl, and may be unsubstituted or substituted with one or two moieties selected from halogen, —CN, —CONH₂ and —CF₃, or B₂ is selected from:

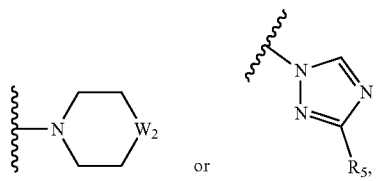

wherein:
W₂ is selected from CH₂, O, SO₂, CHAr and NAr;
Ar is aryl or heteroaryl containing 1 to 3 heteroatoms; and
R₅ is selected from —H, -Ph and —COOMe.

7. The compound of claim 1, wherein B₂ is selected from phenyl, pyrrolyl, pyrazolyl, imidazolyl, pyridinyl, purinyl, benzimidazolyl, indolyl, quinolinyl or quinoxalinyl, and may be unsubstituted or substituted with one or two moieties selected from halogen, —CN, —CONH₂ and —CF₃.

8. The compound of claim 6, wherein B₂ is selected from pyrrolyl, pyrazolyl, imidazolyl, purinyl, benzimidazolyl or quinoxalinyl, and may be unsubstituted or substituted with one or two moieties selected from halogen, —CN, —CONH₂ and —CF₃.

9. The compound of claim 1, wherein B₂ is selected from:

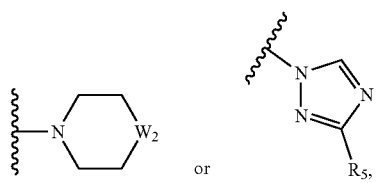

wherein:
W₂ is selected from CH₂, O, SO₂, CHAr and NAr;
Ar is aryl or heteroaryl containing 1 to 3 heteroatoms; and
R₅ is selected from —H, -Ph and —COOMe.

10. The compound of claim 6, wherein B₂ is selected from:

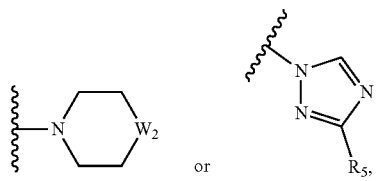

wherein:
W₂ is selected from CH₂, O, SO₂, CHAr and NAr;
Ar is aryl or heteroaryl containing 1 to 3 heteroatoms; and
R₅ is selected from —H, -Ph and —COOMe.

* * * * *